(12) United States Patent
Kriesel et al.

(10) Patent No.: US 8,292,848 B2
(45) Date of Patent: *Oct. 23, 2012

(54) FLUID DISPENSING DEVICE WITH ADDITIVE

(75) Inventors: Marshall S. Kriesel, Saint Paul, MN (US); Joshua W. Kriesel, San Francisco, CA (US)

(73) Assignee: Bio Quiddity, Inc., San Francisco, CA (US)

( * ) Notice: Subject to any disclaimer, the term of this patent is extended or adjusted under 35 U.S.C. 154(b) by 1173 days.

This patent is subject to a terminal disclaimer.

(21) Appl. No.: 11/823,084

(22) Filed: Jun. 25, 2007

(65) Prior Publication Data
US 2008/0027376 A1 Jan. 31, 2008

Related U.S. Application Data

(60) Provisional application No. 60/834,766, filed on Jul. 31, 2006.

(51) Int. Cl.
*A61M 37/00* (2006.01)
(52) U.S. Cl. ...................................................... 604/132
(58) Field of Classification Search .......... 604/131–151, 604/890.1, 891.1
See application file for complete search history.

(56) References Cited

U.S. PATENT DOCUMENTS

| 2,236,084 A | 3/1941 | Brown |
| RE27,155 E | 7/1971 | Hansen |
| 3,731,681 A | 5/1973 | Blackshear et al. |
| 3,884,228 A | 5/1975 | Hahn |
| 4,140,117 A * | 2/1979 | Buckles et al. ............... 604/132 |
| 4,381,006 A | 4/1983 | Genese |
| 4,525,165 A | 6/1985 | Fischell |
| 4,557,728 A | 12/1985 | Sealfon et al. |
| 4,608,042 A | 8/1986 | Vanderveen et al. |
| 4,681,566 A | 7/1987 | Fenton, Jr. et al. |
| 4,755,172 A | 7/1988 | Baldwin |
| 4,772,263 A | 9/1988 | Dorman et al. |
| 4,850,807 A | 7/1989 | Frantz |
| 4,863,429 A | 9/1989 | Baldwin |
| 5,007,556 A | 4/1991 | Lover |
| 5,014,750 A | 5/1991 | Winchell et al. |
| 5,098,377 A | 3/1992 | Borsanyi et al. |
| 5,100,389 A | 3/1992 | Vaillancourt |
| 5,176,641 A | 1/1993 | Idriss |
| 5,205,820 A | 4/1993 | Kriesel |
| 5,226,551 A | 7/1993 | Robbins, III |
| 5,236,418 A | 8/1993 | Kriesel |
| 5,290,259 A | 3/1994 | Fischer |
| 5,306,257 A | 4/1994 | Zdeb |
| 5,314,405 A | 5/1994 | Kriesel et al. |
| 5,333,761 A | 8/1994 | Davis et al. |
| 5,336,188 A | 8/1994 | Kriesel |
| 5,346,476 A | 9/1994 | Elson |
| 5,380,287 A | 1/1995 | Kikuchi et al. |
| 5,411,480 A | 5/1995 | Kriesel |
| 5,419,771 A | 5/1995 | Kriesel |

(Continued)

*Primary Examiner* — Matthew F Desanto
(74) *Attorney, Agent, or Firm* — James E. Brunton

(57) ABSTRACT

A dispensing device for dispensing medicaments to a patient which includes a supporting structure; a carriage assembly interconnected with the supporting structure for movement between a first position and a second position and a semi-rigid, collapsible reservoir carried by the carriage assembly. A stored energy source is operably associated with the carriage assembly for moving the carriage assembly between the first and second positions. The device also includes novel structure, including fill-vials, for adding medicaments to the fluid within the fluid reservoir.

11 Claims, 39 Drawing Sheets

U.S. PATENT DOCUMENTS

| | | |
|---|---|---|
| 5,484,410 A | 1/1996 | Kriesel |
| 5,499,968 A | 3/1996 | Milijasevic et al. |
| 5,514,090 A | 5/1996 | Kriesel et al. |
| 5,545,139 A | 8/1996 | Kriesel |
| 5,620,420 A | 4/1997 | Kriesel |
| 5,632,406 A | 5/1997 | Robbins, III |
| 5,693,018 A | 12/1997 | Kriesel et al. |
| 5,693,019 A | 12/1997 | Kriesel |
| 5,720,729 A | 2/1998 | Kriesel |
| 5,721,382 A | 2/1998 | Kriesel et al. |
| 5,735,818 A | 4/1998 | Kriesel et al. |
| 5,741,242 A | 4/1998 | Kriesel |
| 5,743,879 A | 4/1998 | Kriesel |
| 5,766,149 A | 6/1998 | Kriesel et al. |
| 5,779,676 A | 7/1998 | Kriesel et al. |
| 5,807,323 A | 9/1998 | Kriesel et al. |
| 5,836,484 A | 11/1998 | Gerber |
| 5,858,005 A | 1/1999 | Kriesel |
| 5,885,250 A | 3/1999 | Kriesel et al. |
| 5,897,530 A | 4/1999 | Jackson |
| 5,921,962 A | 7/1999 | Kriesel et al. |
| 5,925,017 A | 7/1999 | Kriesel et al. |
| 5,957,891 A | 9/1999 | Kriesel et al. |
| 5,993,425 A | 11/1999 | Kriesel |
| 6,010,482 A | 1/2000 | Kriesel et al. |
| 6,027,472 A | 2/2000 | Kriesel et al. |
| 6,030,363 A | 2/2000 | Kriesel |
| 6,045,533 A | 4/2000 | Kriesel et al. |
| 6,063,059 A | 5/2000 | Kriesel |
| 6,068,613 A | 5/2000 | Kriesel et al. |
| 6,068,614 A | 5/2000 | Kimber et al. |
| 6,086,561 A | 7/2000 | Kriesel et al. |
| 6,090,071 A | 7/2000 | Kriesel |
| 6,095,491 A | 8/2000 | Kriesel |
| 6,126,637 A | 10/2000 | Kriesel et al. |
| 6,126,642 A * | 10/2000 | Kriesel et al. ............. 604/207 |
| 6,152,898 A | 11/2000 | Olsen |
| 6,159,180 A | 12/2000 | Kriesel et al. |
| 6,176,845 B1 | 1/2001 | Kriesel et al. |
| 6,183,441 B1 | 2/2001 | Kriesel et al. |
| 6,190,359 B1 | 2/2001 | Heruth |
| 6,210,368 B1 | 4/2001 | Rogers |
| 6,236,624 B1 | 5/2001 | Kriesel et al. |
| 6,245,041 B1 | 6/2001 | Kriesel |
| 6,258,062 B1 | 7/2001 | Thielen et al. |
| 6,270,481 B1 | 8/2001 | Mason et al. |
| 6,273,133 B1 | 8/2001 | Williamson et al. |
| 6,277,095 B1 | 8/2001 | Kriesel et al. |
| 6,293,159 B1 | 9/2001 | Kriesel et al. |
| 6,319,235 B1 | 11/2001 | Yoshino |
| 6,355,019 B1 | 3/2002 | Kriesel et al. |
| 6,364,865 B1 * | 4/2002 | Lavi et al. ............. 604/411 |
| 6,391,006 B1 | 5/2002 | Kriesel et al. |
| 6,394,980 B2 | 5/2002 | Kriesel et al. |
| 6,398,760 B1 | 6/2002 | Danby |
| 6,485,461 B1 | 11/2002 | Mason et al. |
| 6,537,249 B2 | 3/2003 | Kriesel et al. |
| 6,542,350 B1 | 4/2003 | Rogers |
| 6,558,358 B2 * | 5/2003 | Rosoff et al. ............. 604/200 |
| 6,569,125 B2 | 5/2003 | Jepson et al. |
| 6,645,175 B2 | 11/2003 | Kriesel et al. |
| 6,669,668 B1 | 12/2003 | Kleeman et al. |
| 6,740,059 B2 * | 5/2004 | Flaherty ............. 604/67 |
| 7,029,455 B2 | 4/2006 | Flaherty |
| 7,220,245 B2 * | 5/2007 | Kriesel ............. 604/134 |

* cited by examiner

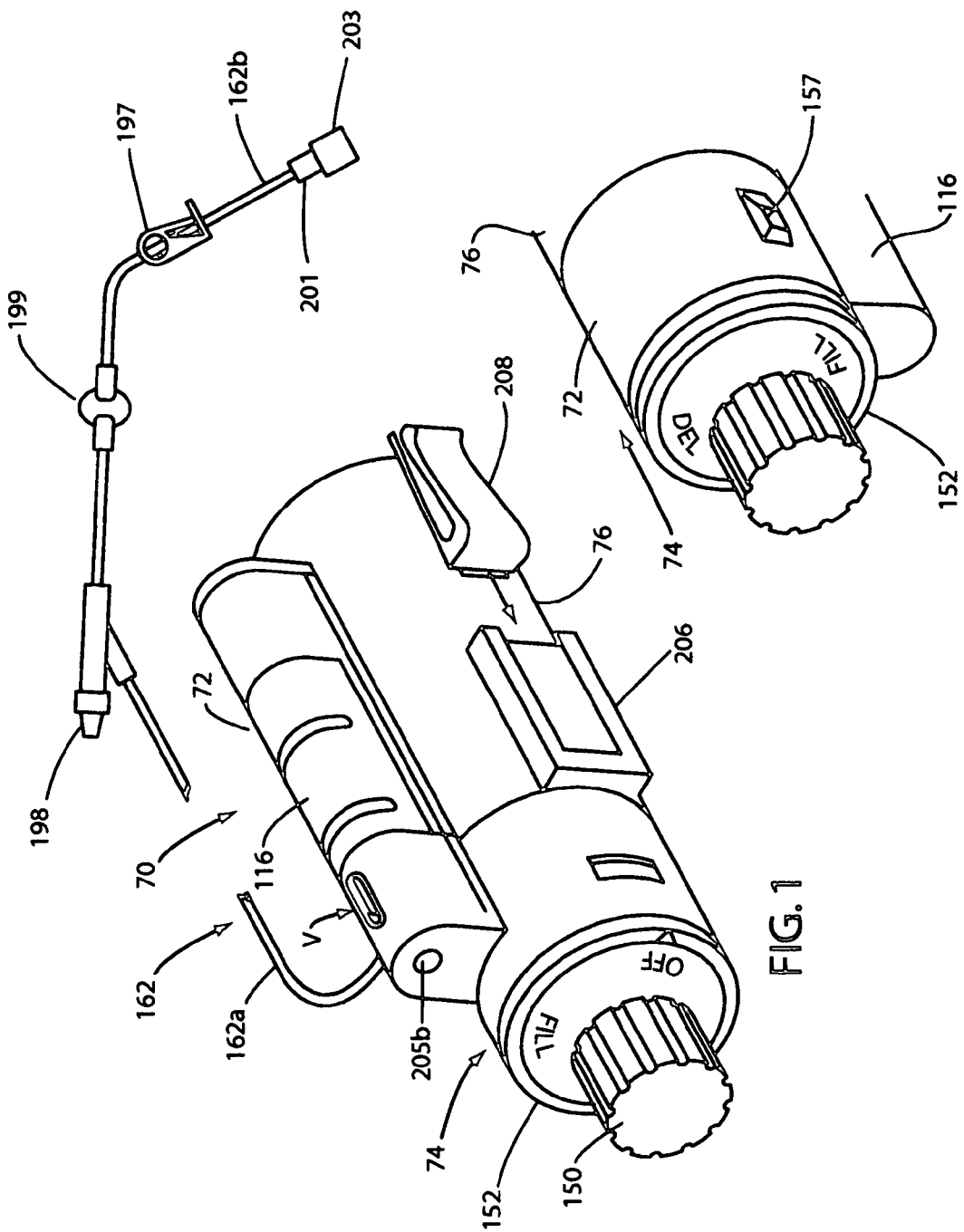

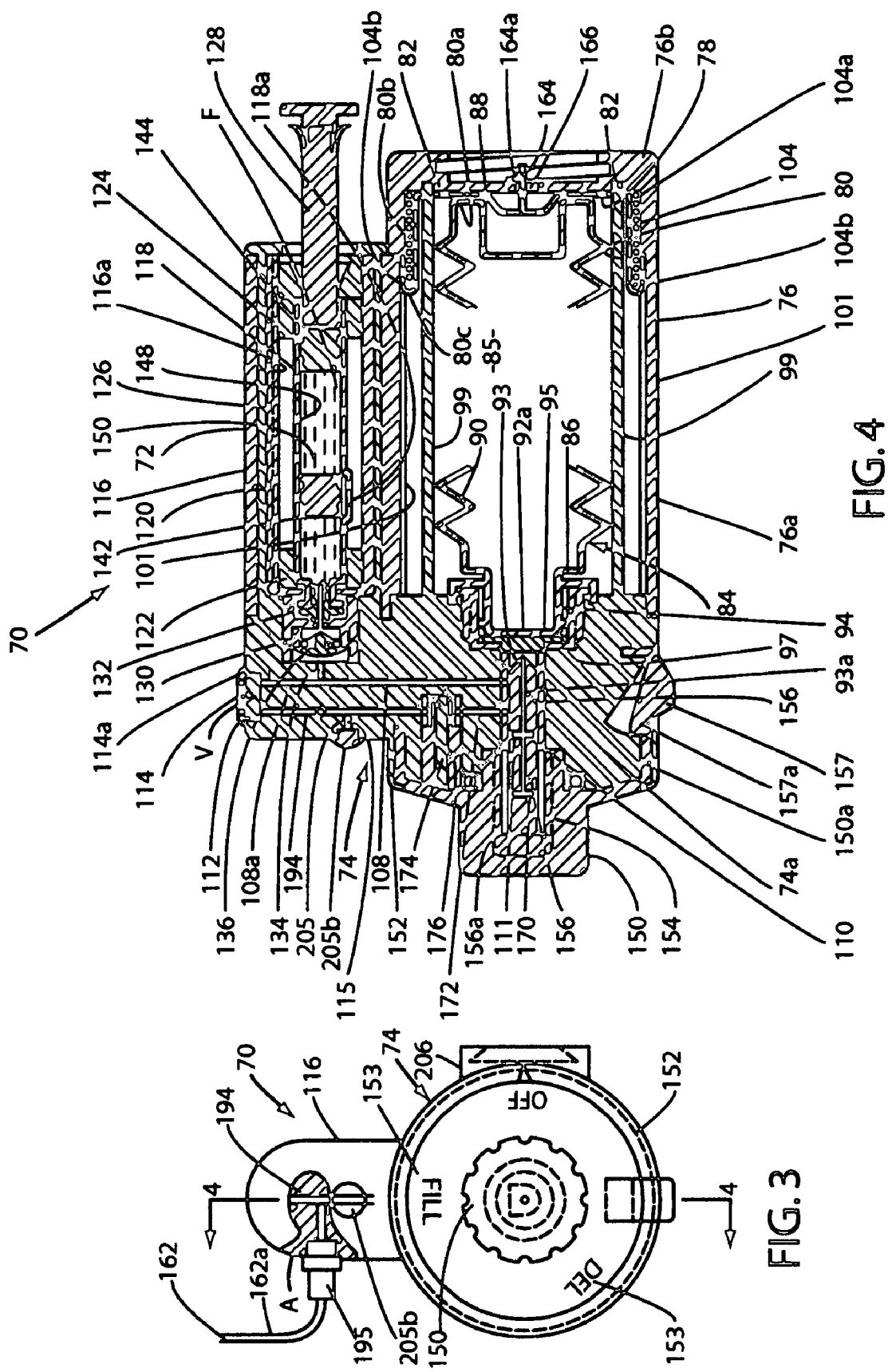

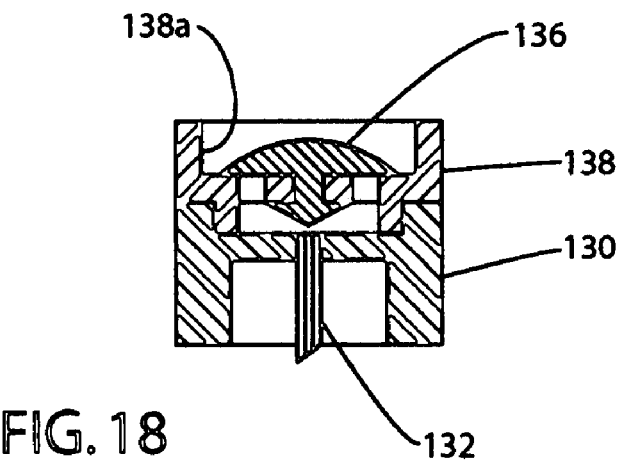
FIG. 18
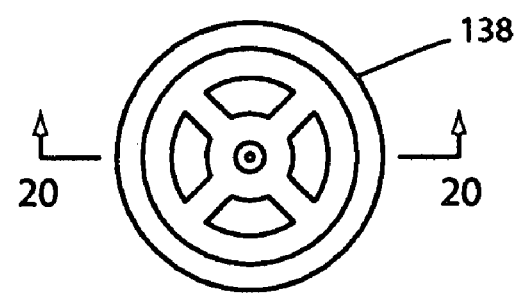
FIG. 19
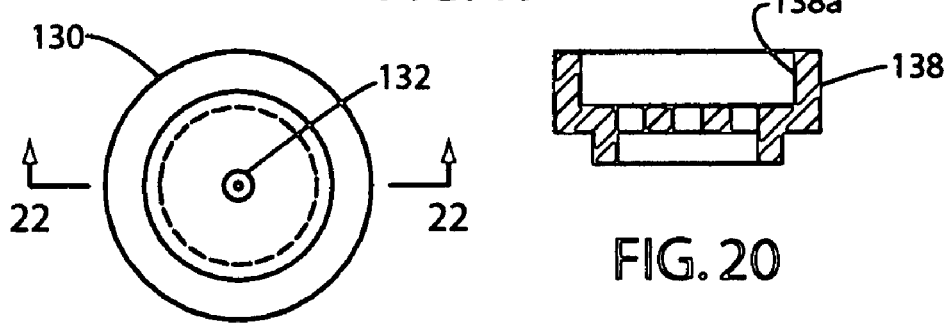
FIG. 20
FIG. 21
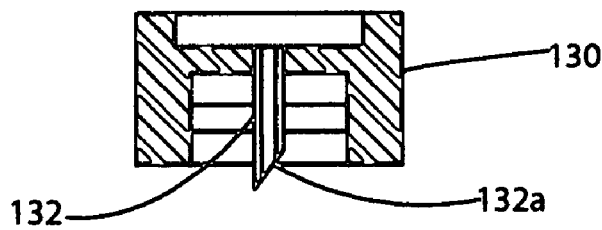
FIG. 22

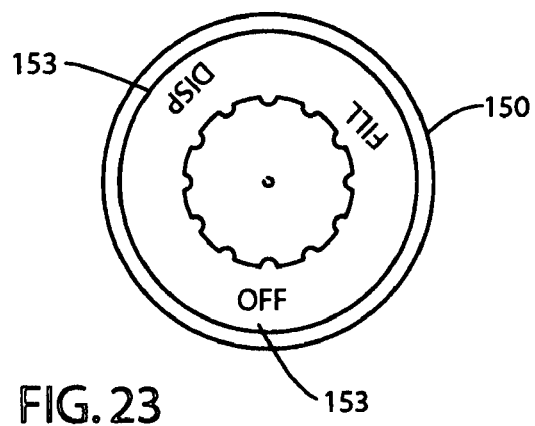
FIG. 23
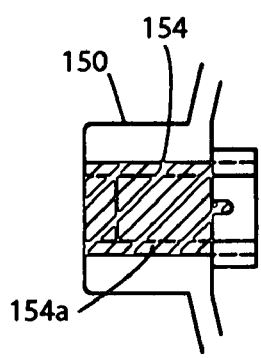
FIG. 26
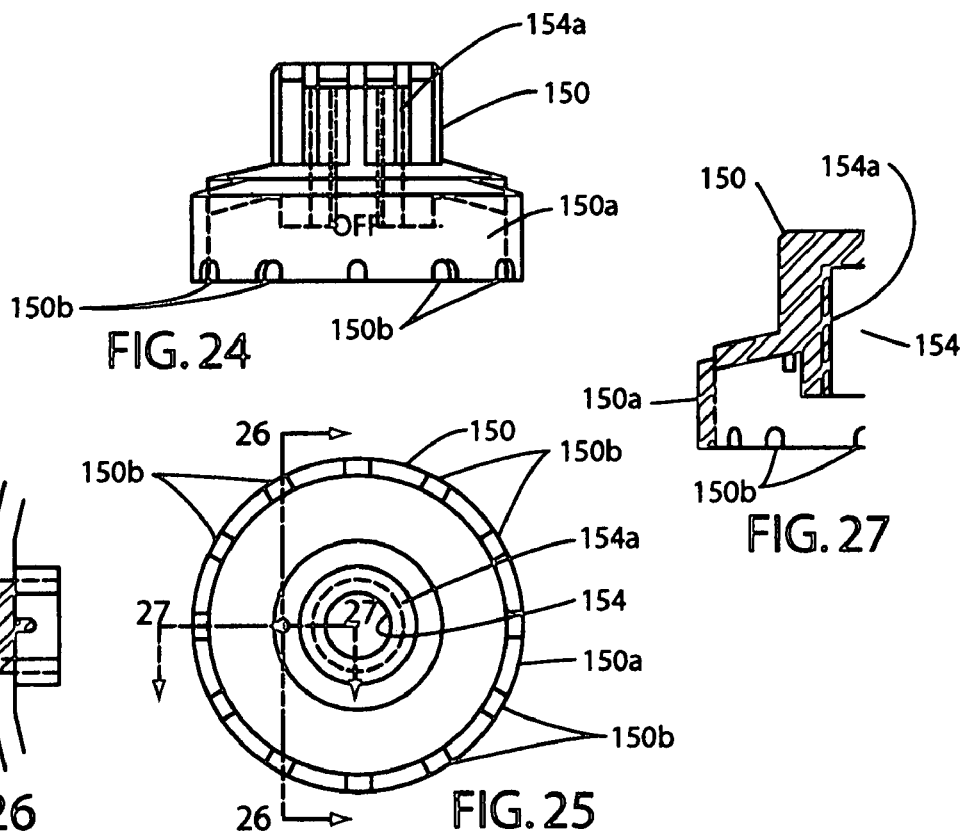
FIG. 24
FIG. 25
FIG. 27

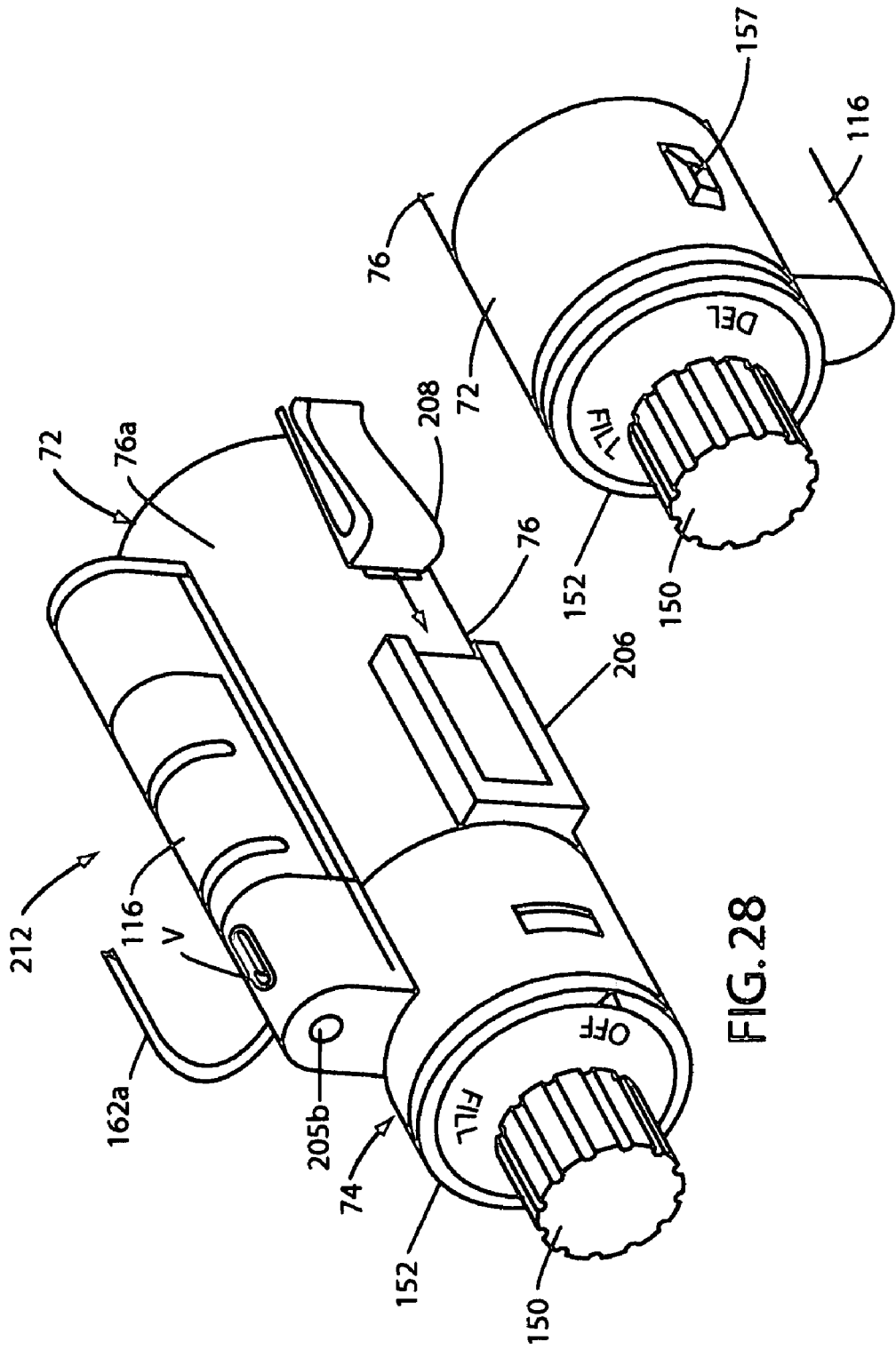

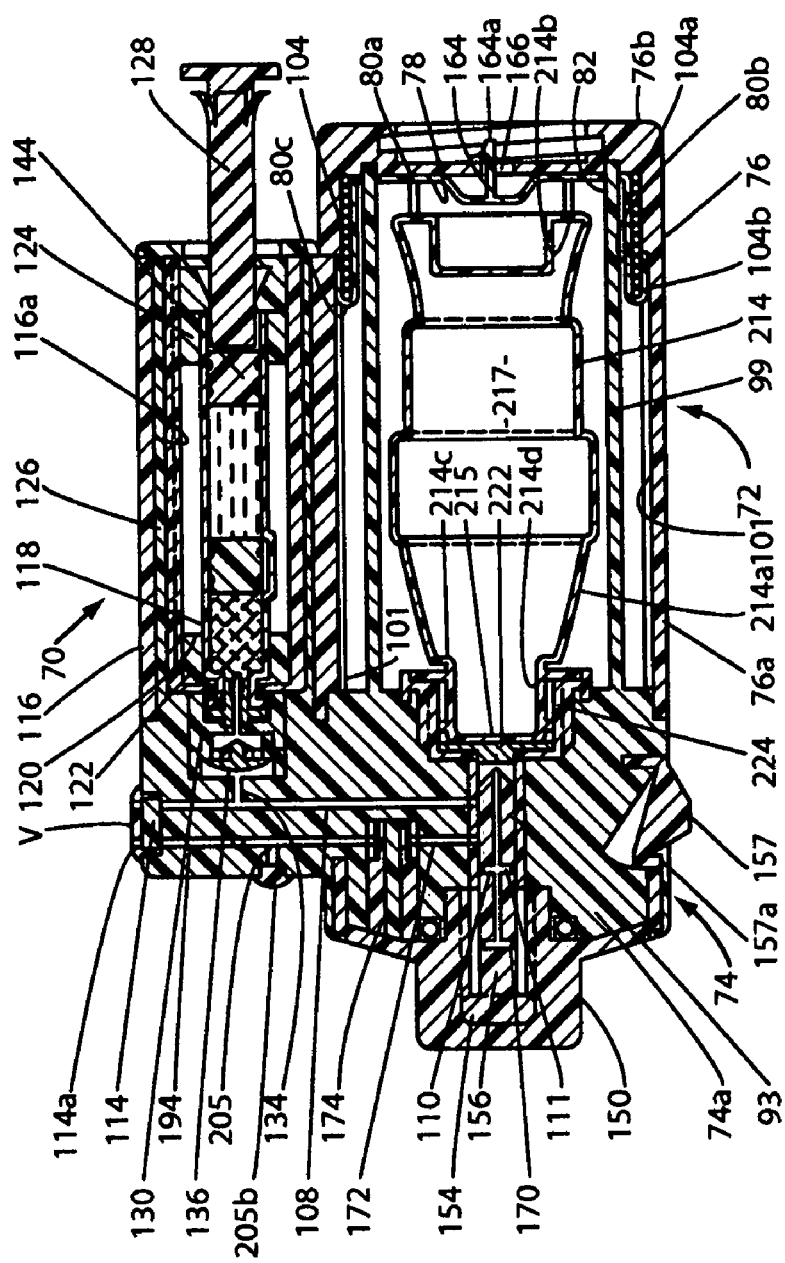
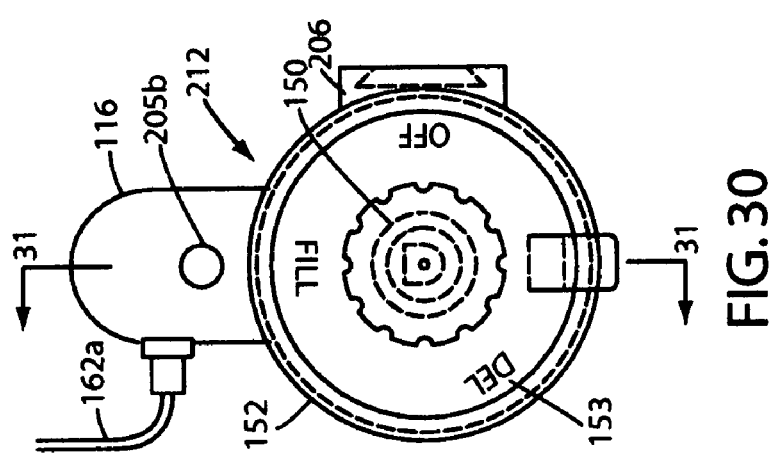
FIG. 31
FIG. 30

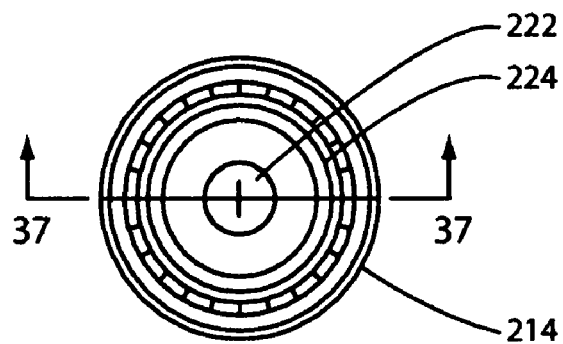
FIG. 36
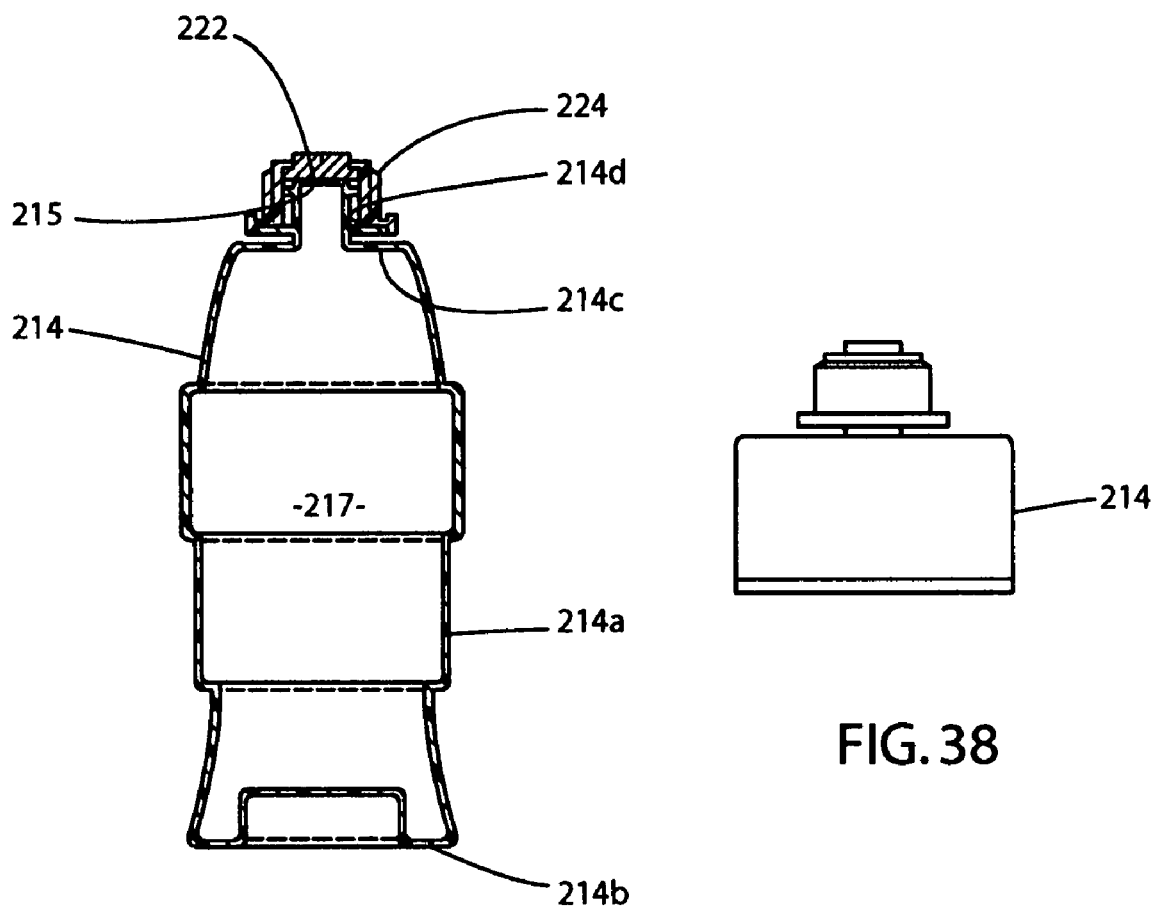
FIG. 37
FIG. 38

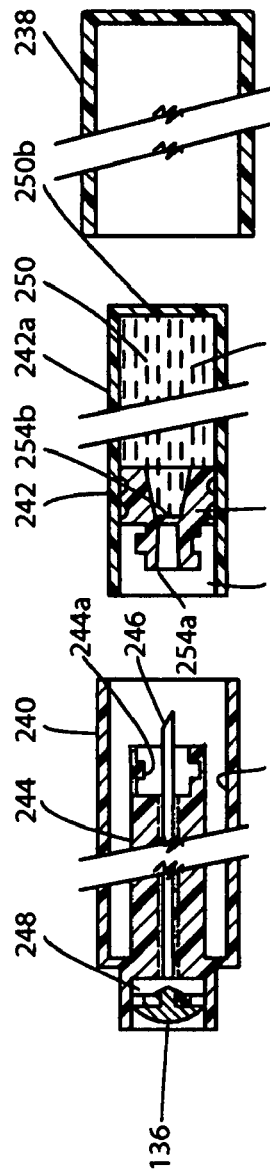
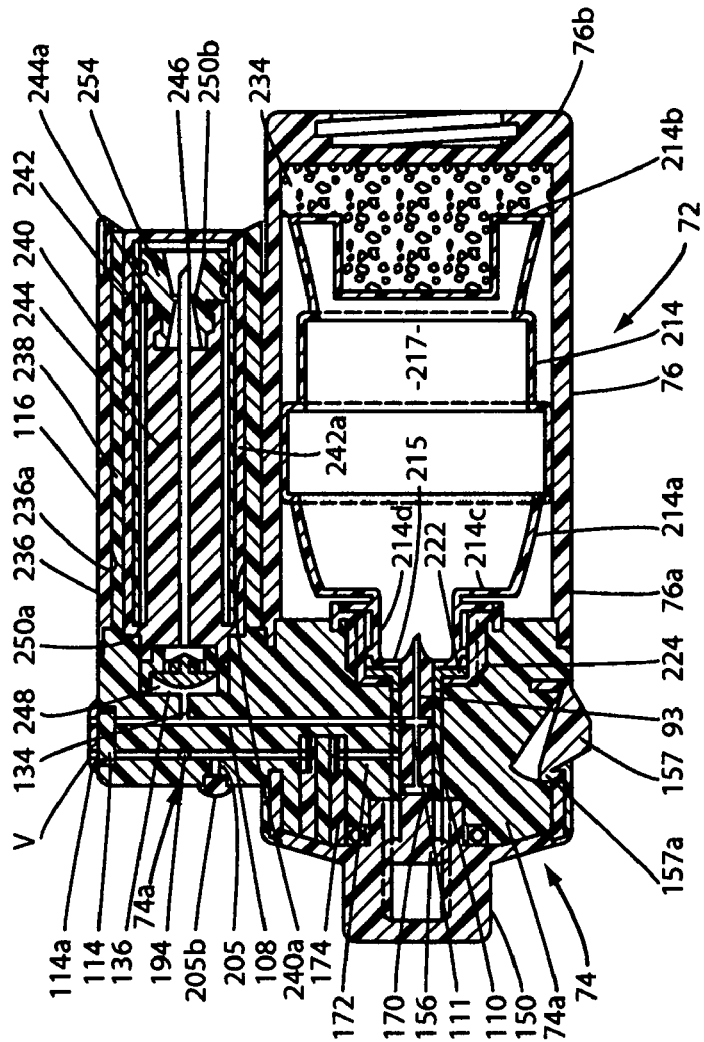
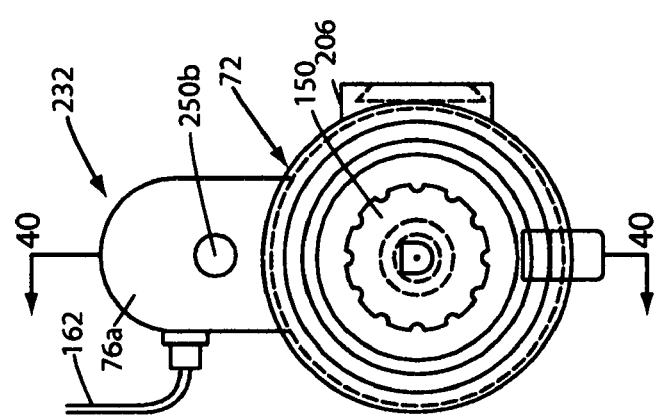
FIG. 41
FIG. 40
FIG. 39

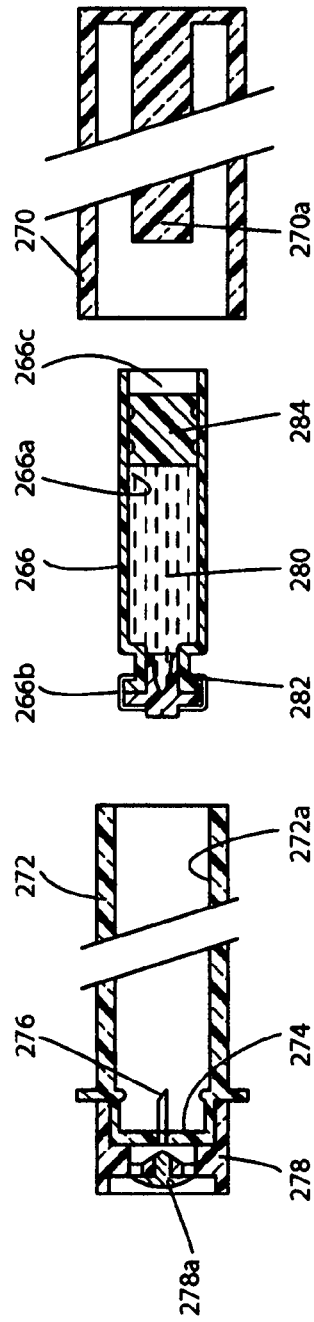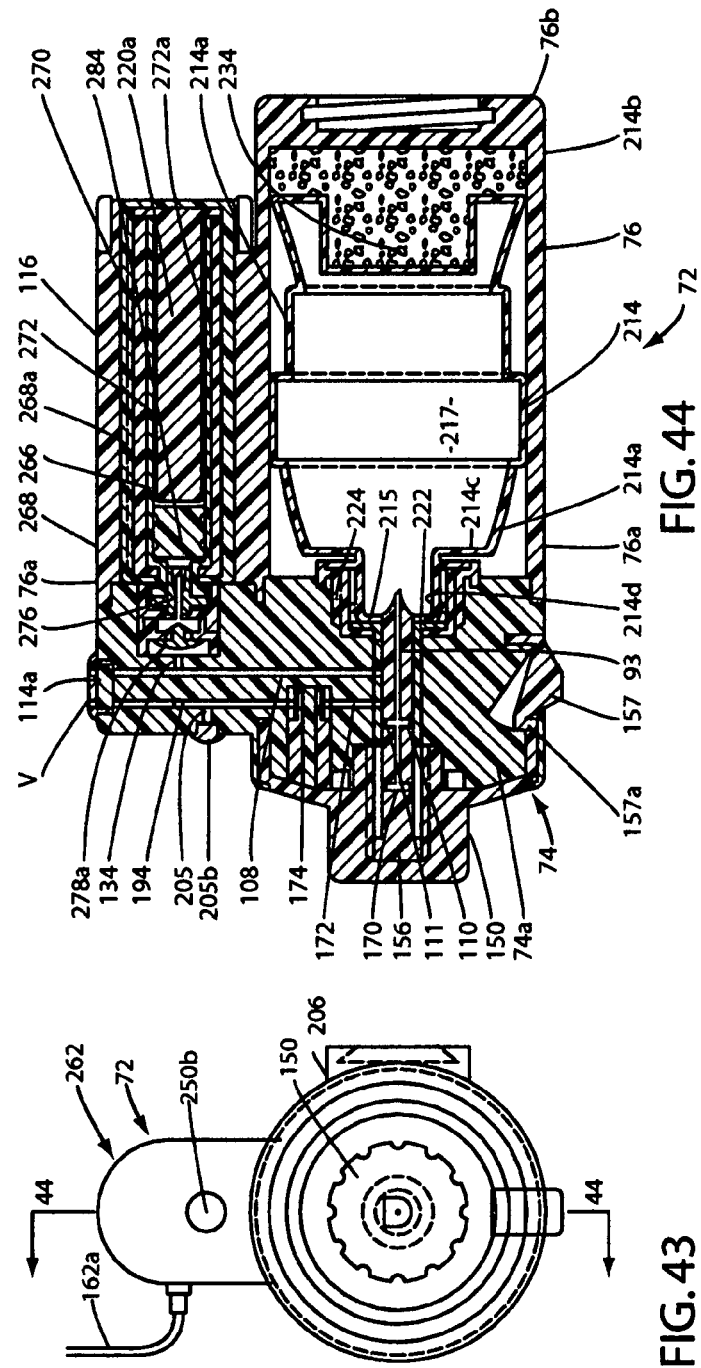

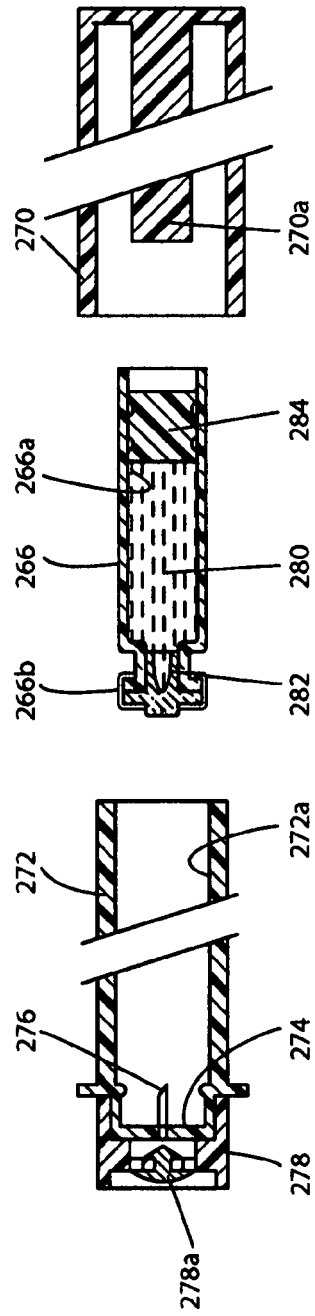
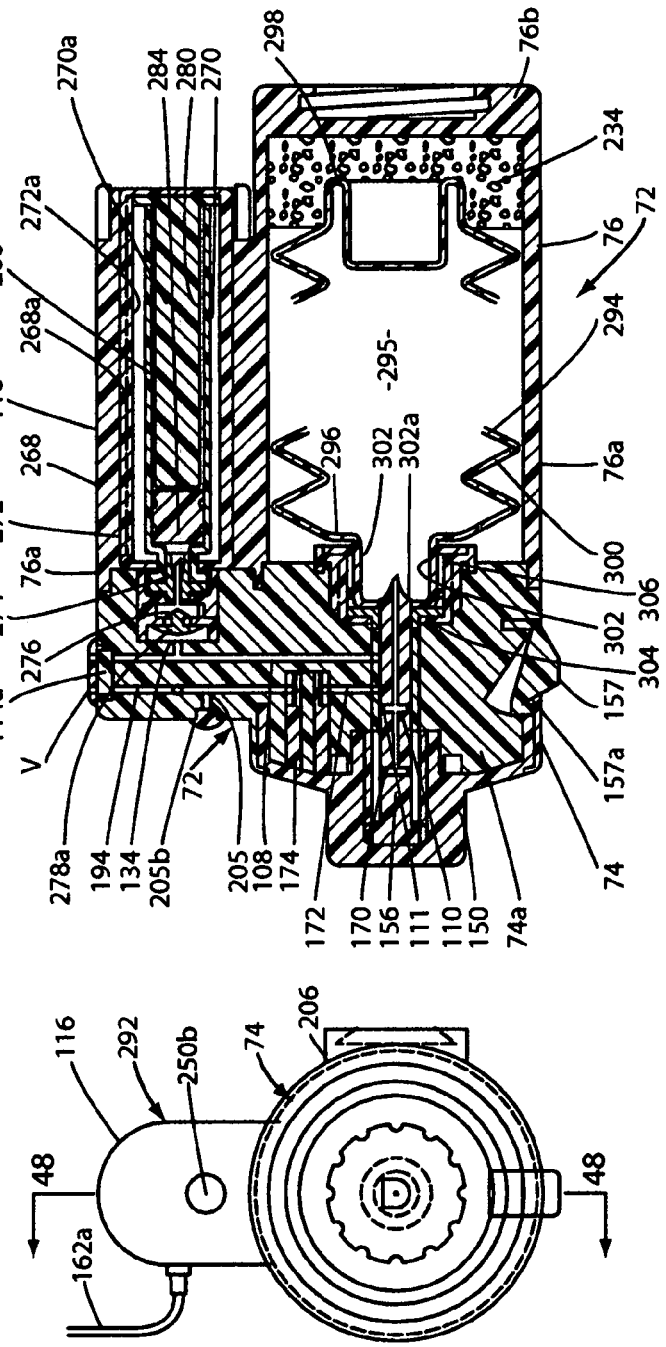

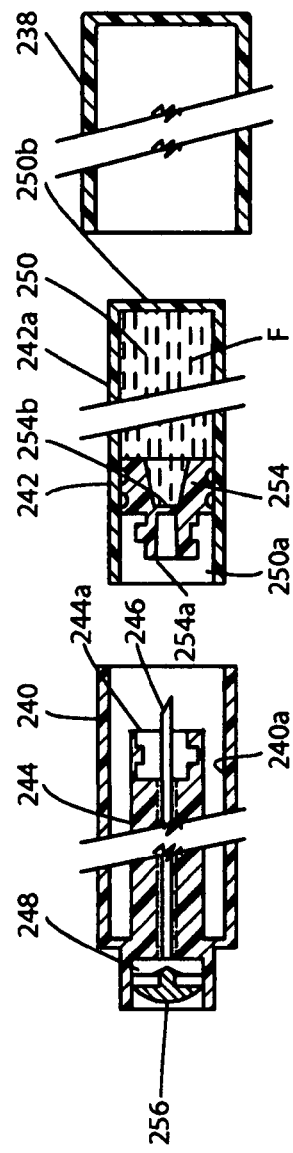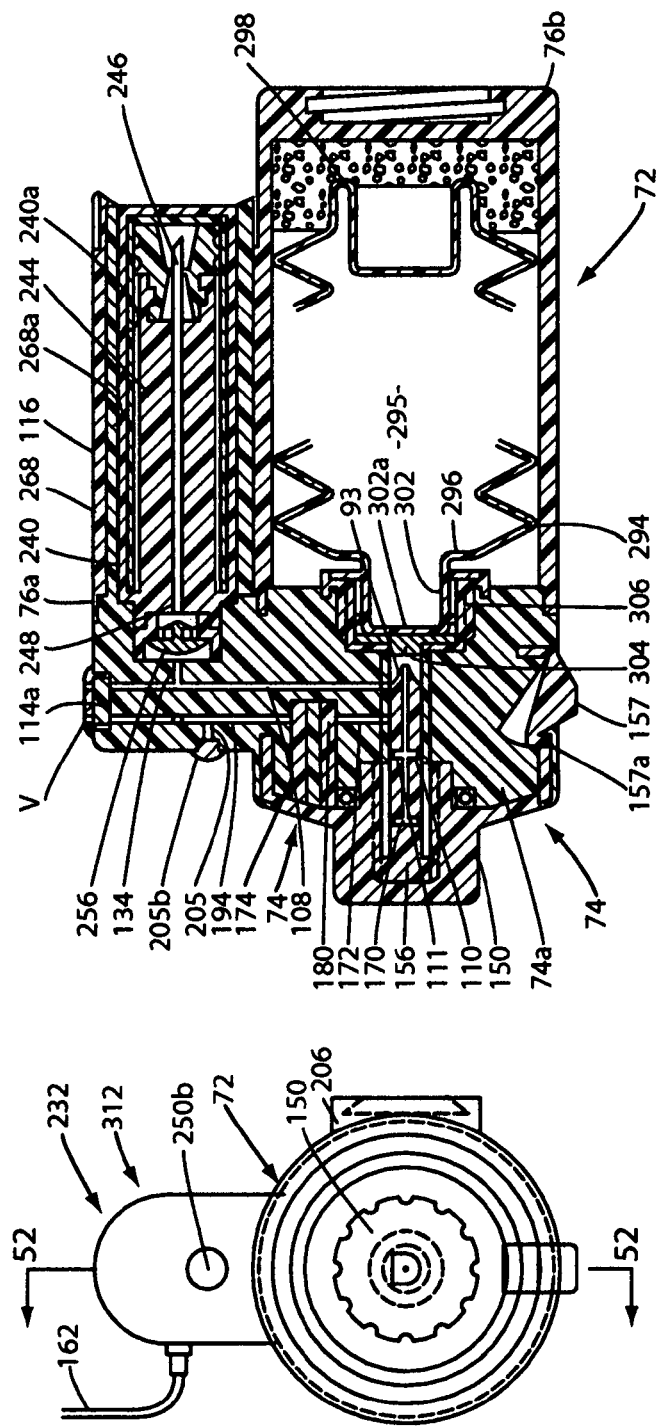

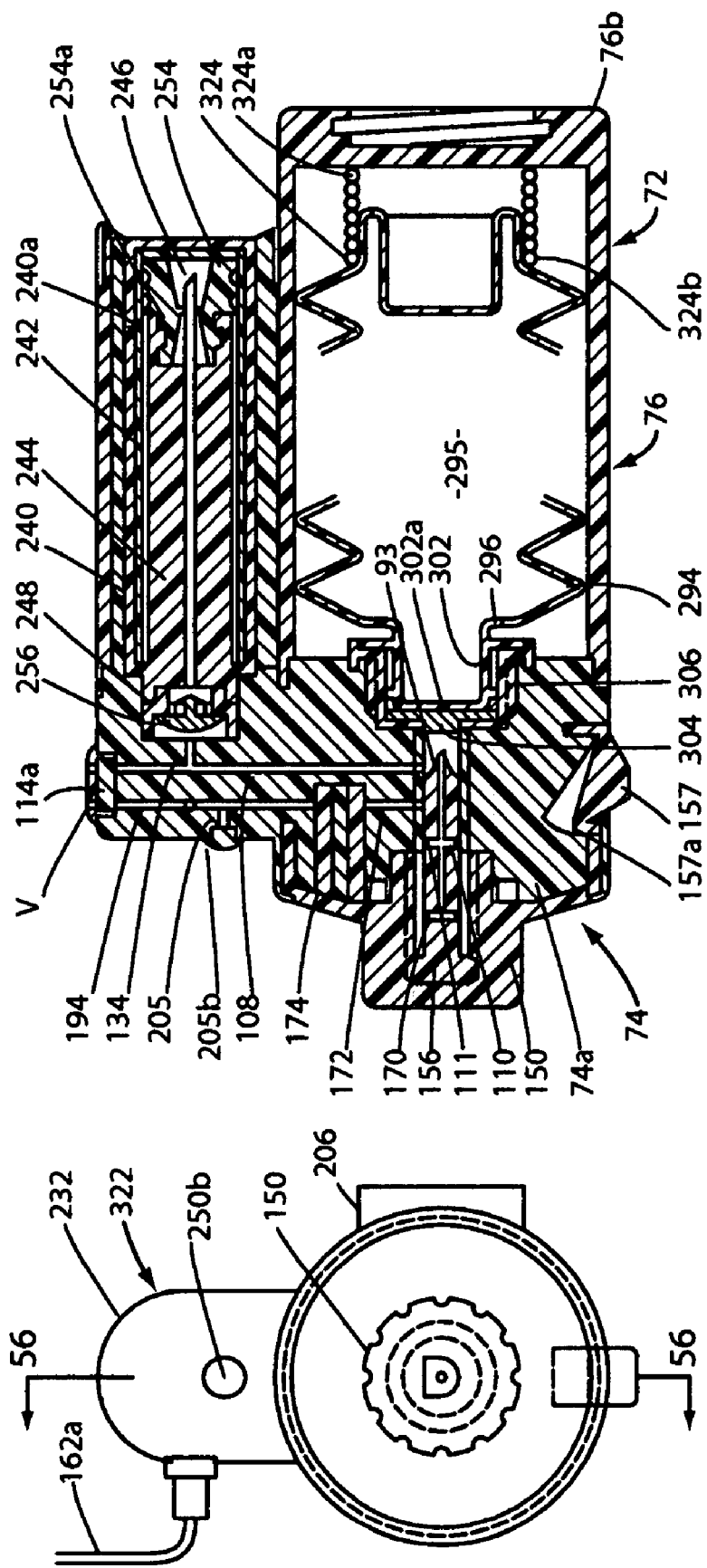

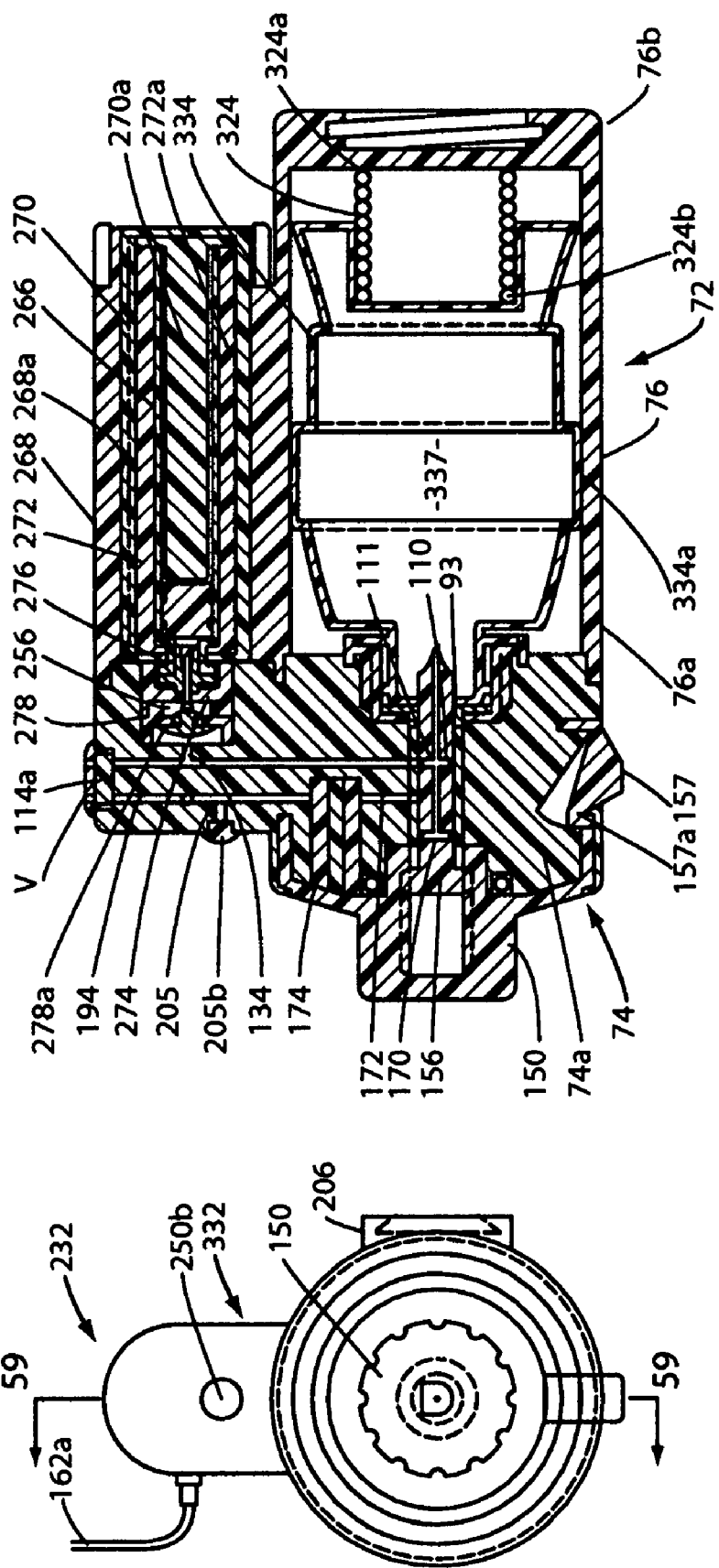

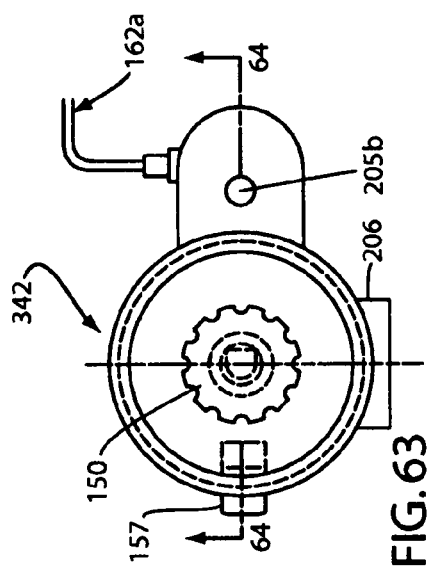
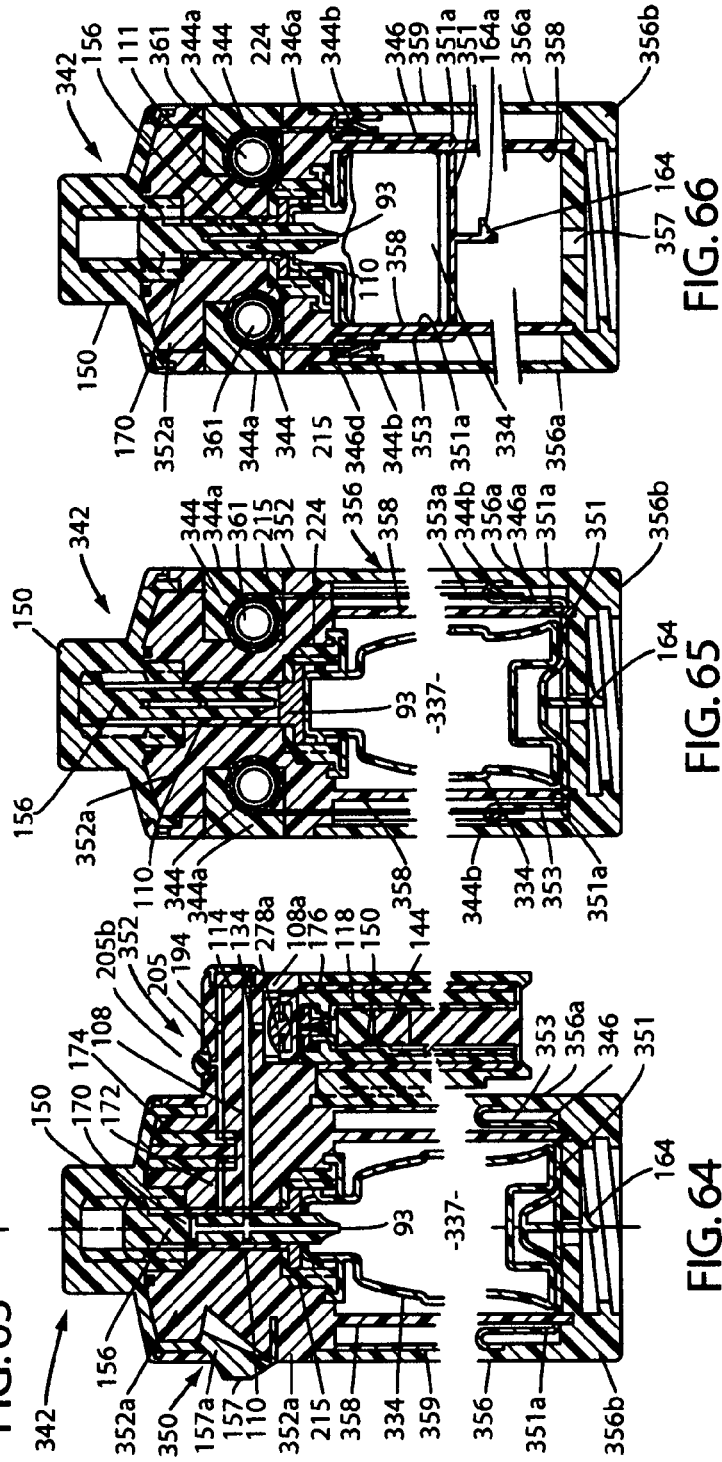
FIG. 63
FIG. 64
FIG. 65
FIG. 66

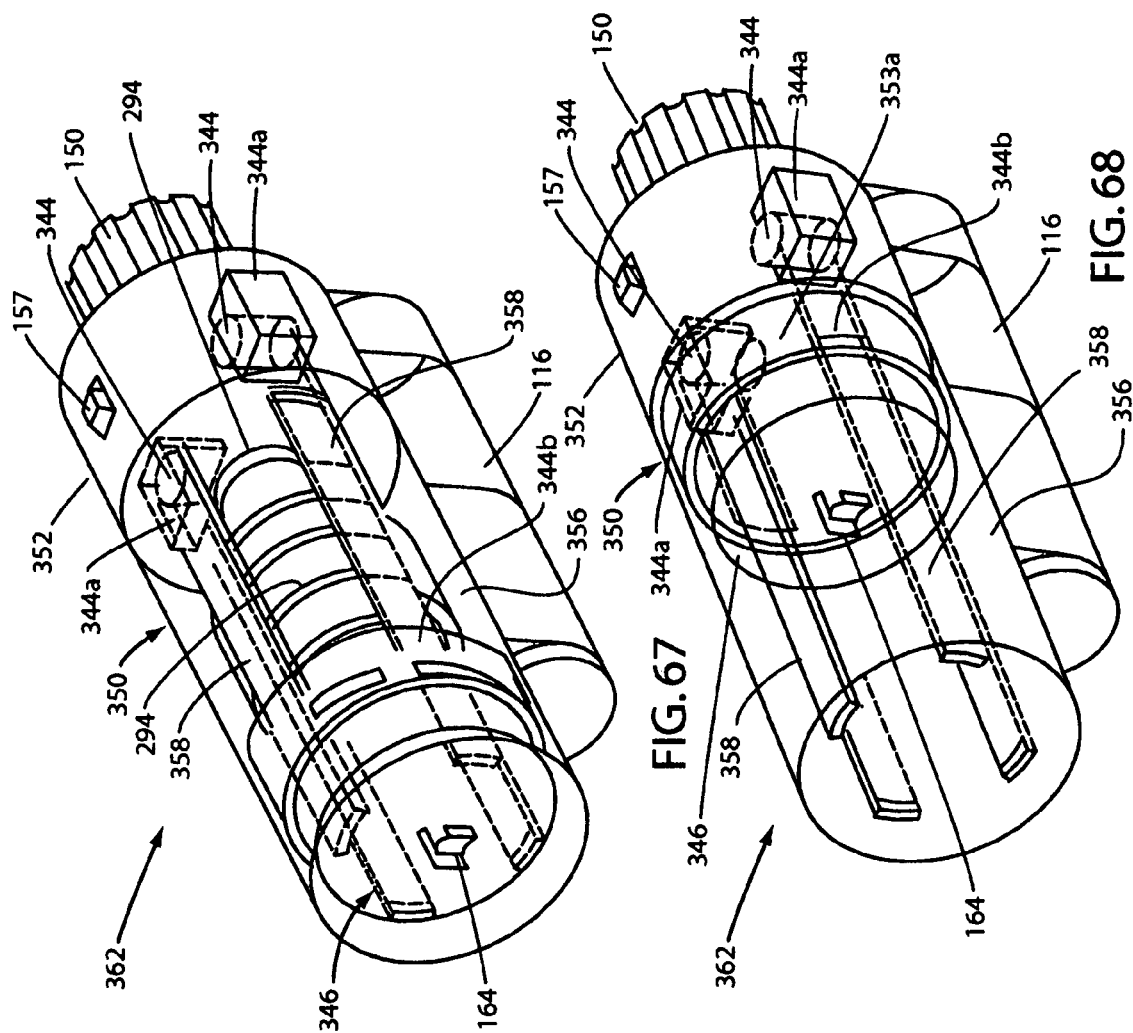

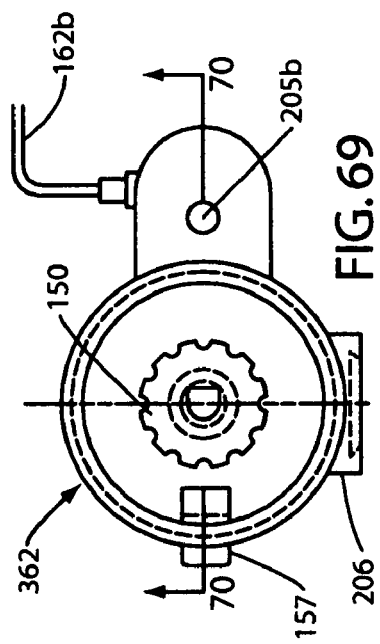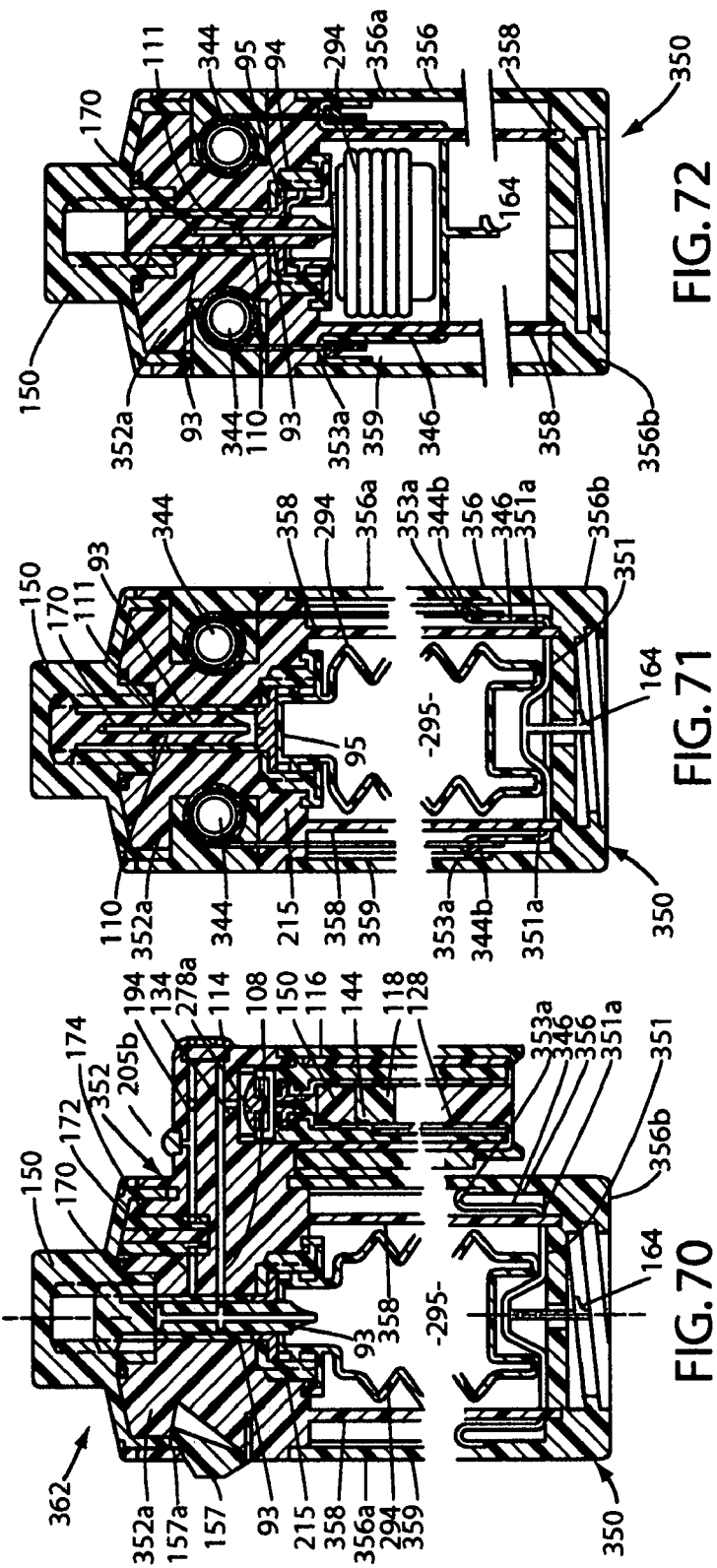

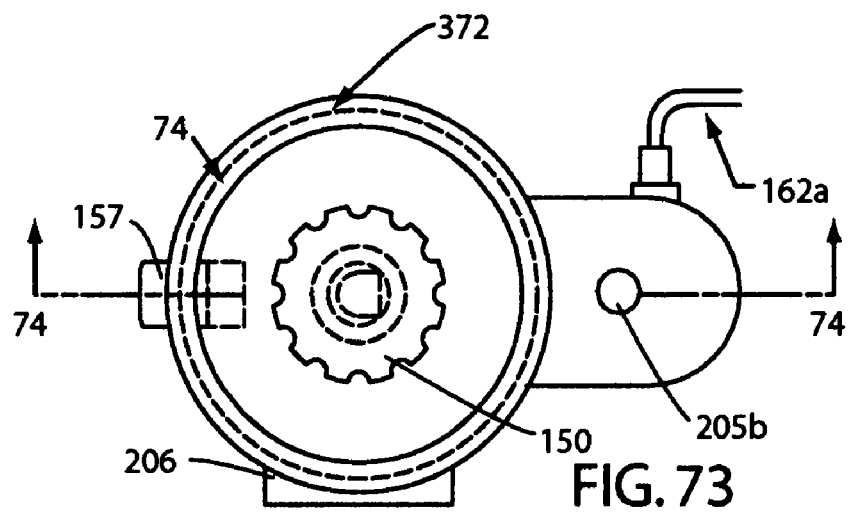
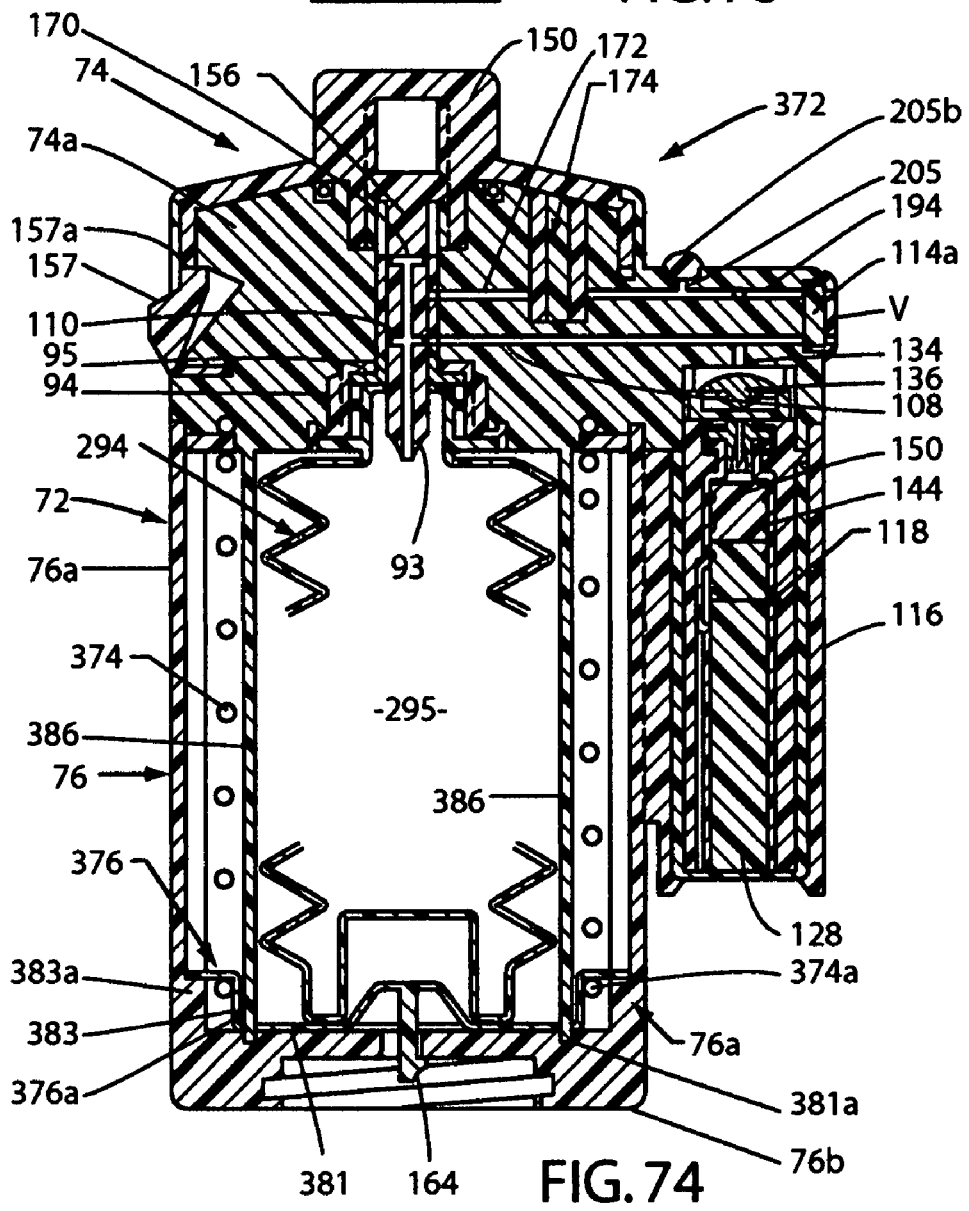

FLUID DISPENSING DEVICE WITH ADDITIVE

This is a Non-Provisional Application claiming the benefit of Provisional Application No. 60/834,766 filed Jul. 31, 2006.

FIELD OF THE INVENTION

The present invention relates generally to fluid dispensing devices. More particularly, the invention concerns medicament dispensers for dispensing medicinal fluids to ambulatory patients.

DESCRIPTION OF THE PRIOR ART

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravametric methods are cumbersome, imprecise and require bed confinement of the patient. Periodic monitoring of the apparatus by the nurse or doctor is required to detect malfunctions of the infusion apparatus. Accordingly, the prior art devices are not well suited for use in those instances where the patient must be transported to a remote facility for treatment.

As will be fully appreciated from the discussion that follows, the devices of the present invention are particularly useful in combat situations. The ability to quickly and efficaciously treat wounded soldiers, especially in unpredictable or remote care settings, can significantly improve chances for patient survival and recovery. Accurate intravenous (IV) drug and fluid delivery technologies for controlling pain, preventing infection, and providing a means for IV access for rapid infusions during patient transport are needed to treat almost all serious injuries.

It is imperative that battlefield medics begin administering life saving medications as soon as possible after a casualty occurs. The continuous maintenance of these treatments is vital until higher echelon medical facilities can be reached. A compact, portable and ready-to-use infusion device that could be easily brought into the battlefield would allow medics to begin drug infusions immediately. Additionally, it would free them to attend to other seriously wounded patients who may require more hands-on care in the trauma environment following triage. In most serious trauma situations on the battlefield, IV drug delivery is required to treat fluid resuscitation, as well as both pain and infection. Drug infusion devices currently available can impede the timely administration of IV infusions in remote care settings.

Expensive electronic infusion pumps are not a practical field solution because of their weight and cumbersome size. Moreover, today's procedures for starting IV infusions on the battlefield are often dangerous because the attending medic must complete several time consuming steps. The labor intensive nature of current gravity solution bag modalities can prevent medics from attending to other patients also suffering from life threatening injuries. In some cases, patients themselves have been forced to hold infusion bags elevated in order to receive the medication by gravity drip.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs biopharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

SUMMARY OF THE INVENTION

By way of brief summary, one form of the dispensing device of the present invention for dispensing medicaments to a patient comprises a supporting structure; a carriage assembly interconnected with the supporting structure for movement between a first position and a second position; a semi-rigid collapsible reservoir carried by the carriage assembly, the collapsible reservoir having an outlet port; guide means connected to the supporting structure for guiding travel of the carriage assembly between the first position and said second positions; a stored energy source operably associated with the carriage assembly for moving the carriage assembly between the first and second positions; adding means for adding medicaments to the fluid within the fluid reservoir and an administration set including an administration line interconnected with the outlet port of the reservoir.

With the forgoing in mind, it is an object of the present invention to provide a compact fluid dispenser for use in controllably dispensing fluid medicaments, such as, antibiotics, anesthetics, analgesics, and like medicinal agents from pre-filled dispenser at a uniform rate.

Another object of the invention is to provide a small, compact fluid dispenser of simple construction that can be used in the field with a minimum amount of training.

Another object of the invention is to allow infusion therapy to be initiated quickly, at will, at point of care on the battlefield so that the attending medic or medical professional can more efficiently deal with triage situations in austere environments.

Another object of the invention is to provide a dispenser in which a stored energy source is provided in the form of a compressible, expandable or retractable member of novel construction that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser of simple construction which includes a novel adding means for adding medicaments to the fluid contained within the fluid reservoir.

Another object of the invention is to provide a fluid dispenser as described in the preceding paragraph which embodies a semi-rigid collapsible container that includes a fluid reservoir that contains the beneficial agents to be delivered to the patient.

Another object of the invention is to provide a fluid dispenser of the class described which is compact and lightweight, is easy for ambulatory patients to use, is fully disposable and is extremely reliable in operation.

Another object of the invention is to provide a small, compact fluid dispenser that includes a housing to which vials can be connected for use in adding medicaments to the fluid within the fluid reservoir of the device.

Another object of the invention is to provide a fluid dispenser as described in the preceding paragraphs that is easy and inexpensive to manufacture in large quantities.

BRIEF DESCRIPTION OF THE DRAWINGS

FIG. 1 is a generally perspective top view of one form of the fluid dispensing device of the present invention for dispensing medicaments to a patient.

FIG. 2 is a fragmentary, generally perspective bottom view of the front portion of the fluid dispensing device shown in FIG. 1.

FIG. 3 is an enlarged front view of the fluid dispensing device shown in FIG. 1.

FIG. 4 is a cross-sectional view taken along lines 4-4 of FIG. 3.

FIG. 18 is an enlarged, cross-sectional view of the check valve, check valve housing and needle housing of the adding means of this latest form of the invention.

FIG. 19 is a top plan view of the check valve housing shown FIG. 20.

FIG. 20 is a cross-sectional view taken along lines 20-20 of FIG. 19.

FIG. 21 is a top plan view of the needle housing of one form of the adding means of the invention.

FIG. 22 is a cross-sectional view taken along lines 22-22 of FIG. 21.

FIG. 23 is a top plan view of the dispenser control knob of the fluid delivery device shown in FIG. 1.

FIG. 24 is a side-elevational view of the dispenser control knob shown in FIG. 23.

FIG. 25 is a bottom plan view of the dispenser control knob shown in FIG. 24.

FIG. 26 is a cross-sectional view taken along lines 26-26 of FIG. 25.

FIG. 27 is a cross-sectional view taken along lines 27-27 of FIG. 25.

FIG. 28 is a generally perspective top view of an alternate form of the fluid dispensing device of the present invention for dispensing medicaments to a patient.

FIG. 29 is a fragmentary, generally perspective bottom view of the front portion of the fluid dispensing device shown in FIG. 28.

FIG. 30 is an enlarged top view of the fluid dispensing device shown in FIG. 28.

FIG. 31 is a cross-sectional view taken along lines 31-31 of FIG. 30.

FIG. 36 is a top plan view of the fluid reservoir assembly of this latest form of the invention.

FIG. 37 is a cross-sectional view taken along lines 37-37 of FIG. 36.

FIG. 38 is a side-elevational view illustrating the appearance of the fluid reservoir in a collapsed configuration.

FIG. 39 is a top view of still another alternate form of the fluid dispensing device of the present invention for dispensing medicaments to a patient.

FIG. 40 is a cross-sectional view taken along lines 40-40 of FIG. 39.

FIG. 41 is a cross-sectional, exploded view of a portion of the adding means of this latest form of the invention.

FIG. 43 is a front view of yet another alternate form of the fluid dispensing device of the present invention for dispensing medicaments to a patient.

FIG. 44 is a cross-sectional view taken along lines 44-44 of FIG. 43.

FIG. 45 is a cross-sectional, exploded view of a portion of the adding means of the form of the invention shown in FIG. 44.

FIG. 47 is a front view of still another alternate form of the fluid dispensing device of the present invention for dispensing medicaments to a patient.

FIG. 48 is a cross-sectional view taken along lines 48-48 of FIG. 47.

FIG. 49 is a cross-sectional, exploded view of a portion of the adding means of the form of the invention shown in FIG. 48.

FIG. 51 is a front view of yet another alternate form of the fluid dispensing device of the present invention for dispensing medicaments to a patient.

FIG. 52 is a cross-sectional view taken along lines 52-52 of FIG. 51.

FIG. 53 is a cross-sectional, exploded view of a portion of the adding means of the form of the invention shown in FIG. 52.

FIG. 55 is a front view of yet another alternate form of the fluid dispensing device of the present invention for dispensing medicaments to a patient.

FIG. 56 is a cross-sectional view taken along lines 56-56 of FIG. 55.

FIG. 58 is a front view of yet another alternate form of the fluid dispensing device of the present invention for dispensing medicaments to a patient.

FIG. 59 is a cross-sectional view taken along lines 59-59 of FIG. 58.

FIG. 63 is a front view the fluid dispensing device shown in FIG. 61.

FIG. 64 is a cross-sectional view taken along lines 64-64 of FIG. 63.

FIG. 65 is a cross-sectional view similar to FIG. 64 showing the device in a starting configuration.

FIG. 66 is a view, similar to FIG. 64 illustrating the appearance of the fluid dispensing device following the fluid delivery step.

FIG. 67 is a generally perspective view, partly broken away to show internal construction, of still another alternate form of the fluid dispensing device of the present invention for dispensing medicaments to a patient.

FIG. 68 is a generally perspective view, similar to FIG. 61 illustrating the appearance of the fluid dispensing device following the fluid delivery step.

FIG. 69 is a front view the fluid dispensing device shown in FIG. 67.

FIG. 70 is a cross-sectional view taken along lines 70-70 of FIG. 69.

FIG. 71 is a cross-sectional view similar to FIG. 70 showing the device in a starting configuration.

FIG. 72 is a view, similar to FIG. 70, illustrating the appearance of the fluid dispensing device following the fluid delivery step.

FIG. 73 is a front view of still another form of the fluid dispensing device of the invention.

FIG. 74 is a cross-sectional view taken along lines 74-74 of FIG. 73.

DESCRIPTION OF THE INVENTION

Figure 4A:
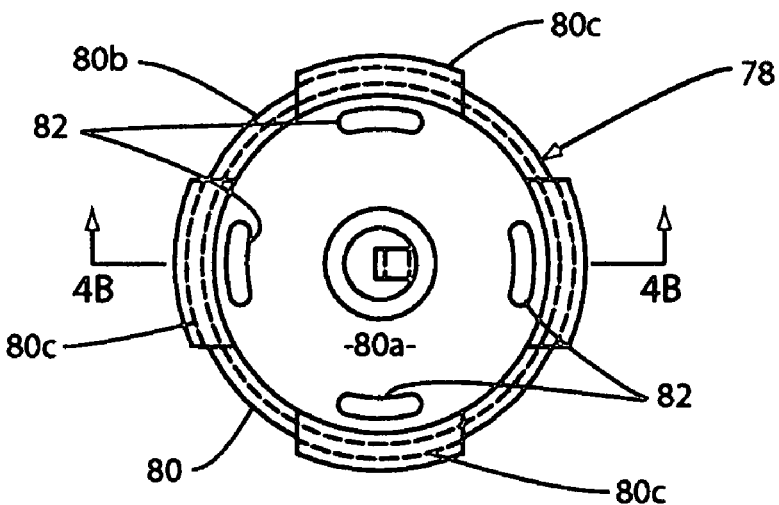
FIG. 4A is a top plan view of the carriage assembly of the fluid delivery device of the invention.

Referring to the drawings and particularly to FIGS. 1 through 5, one form of the dispensing device of the present invention for dispensing medicaments to a patient is there shown and generally designated by the numeral 70. The dispensing device here includes a housing 72 which includes a control portion 74 and a generally cylindrically shaped reservoir housing 76 that is interconnected with the control portion 74 in the manner best seen in FIG. 4 of the drawings. Housing 72 can be constructed from metal, plastic or any suitable material. Reservoir housing 76 includes a generally cylindrically shaped wall portion 76a and a base portion 76b.

Figure 9:
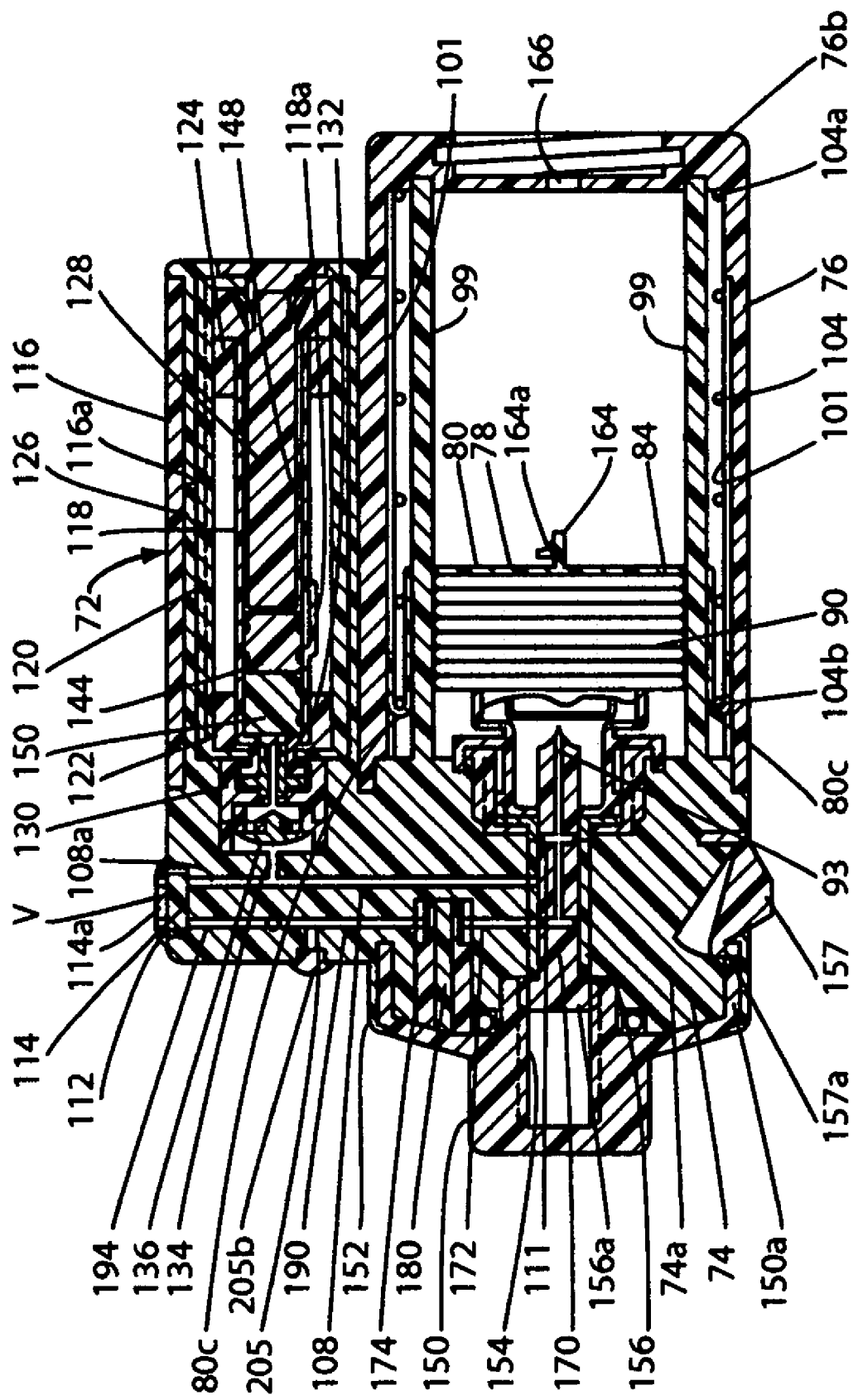
FIG. 9 is a cross-sectional view similar to FIG. 8, but illustrating the fluid delivery step wherein the fluid reservoir is collapsed by the stored energy means and the fluid is caused to flow toward the patient.
Figure 9A:
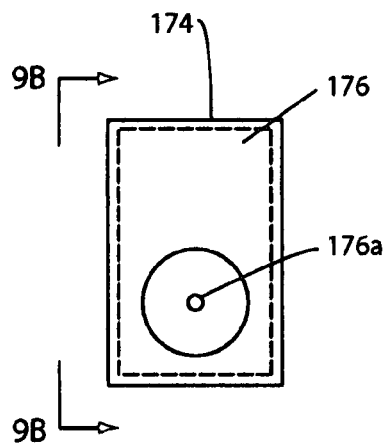
FIG. 9A is a side-elevational view of the rate control assembly of the present invention.
Figure 9B:
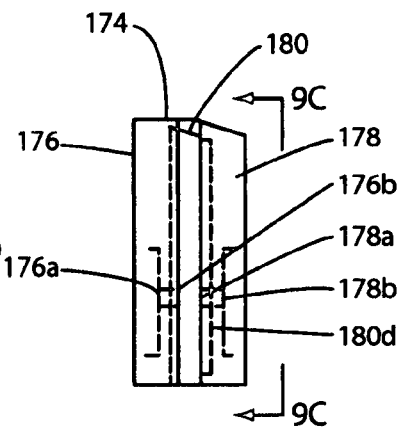
FIG. 9B is a view taken along lines 9B-9B of FIG. 9A.
Figure 9C:
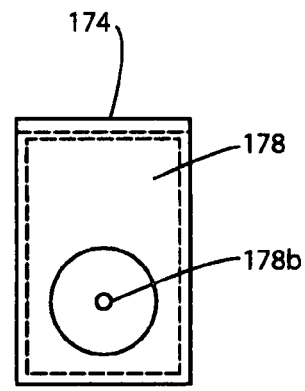
FIG. 9C is a view taken along lines 9C-9C of FIG. 9B.
Figure 9E:
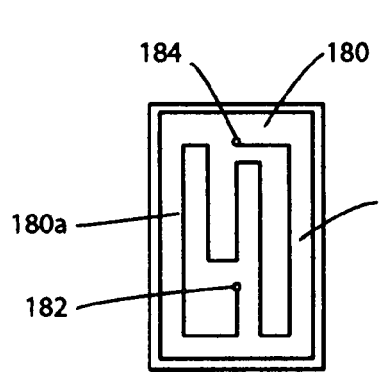
FIG. 9E is a view taken along 9E-9E of FIG. 9D.
Figure 9D:
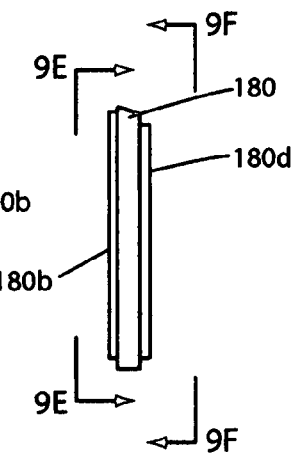
FIG. 9D is an end view of the rate control chip of the rate control assembly shown in FIG. 9B.
Figure 9F:
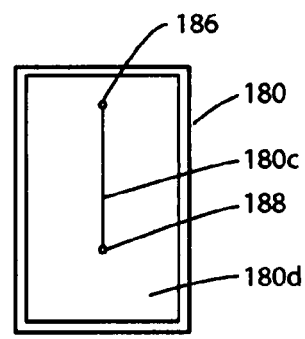
FIG. 9F is a view taken along 9F-9F of FIG. 9D.
Figure 10:
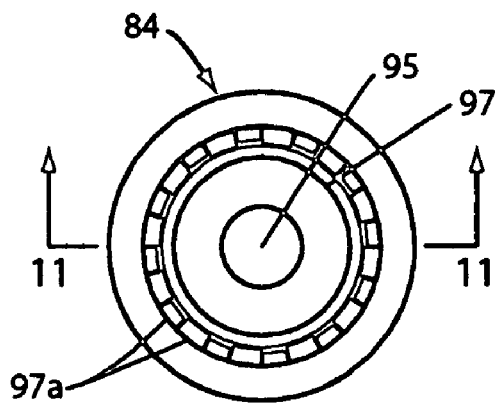
FIG. 10 is a top plan view of one form of the fluid reservoir assembly of the invention.

Disposed within wall portion 76a is a carriage assembly 78 which is movable between a first position shown in FIG. 4 and a second position shown in FIG. 9. As best seen by referring to FIGS. 4, 4A and 5, carriage assembly 78 comprises a carriage 80 having a carriage base 80a that is provided with a plurality of circumferentially spaced openings 82 and a generally cylindrically shaped sidewall 80b which terminates in circumferentially spaced, radially outwardly extending flanges 80c. Carriage assembly 78 is releasably locked in its first position by a novel locking means the character of which will presently be described.

Figure 11:
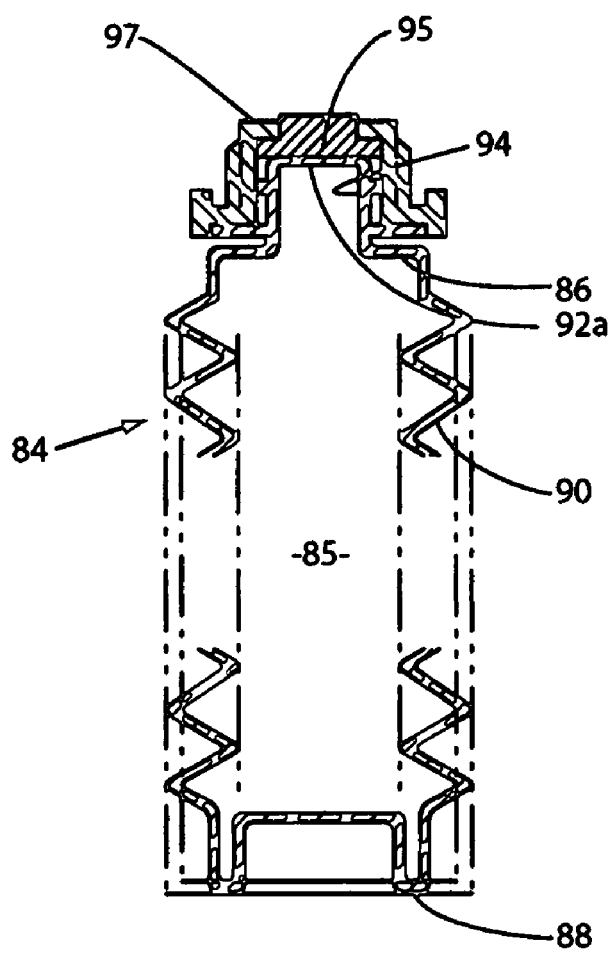
FIG. 11 is a foreshortened, cross-sectional view taken along lines 11-11 of FIG. 10.

Carried by carriage assembly 78 is a semi-rigid reservoir defining assembly 84 that defines a fluid reservoir 85. As indicated in FIGS. 4 and 11, reservoir defining assembly 84 comprises a top wall 86, a bottom wall 88 and an accordion-like side wall 90. Connected to top wall 86 is a neck portion 94 that is sealed by a closure wall 92a.

In the preferred form of the invention reservoir defining assembly 84 is formed in accordance with an aseptic blow-fill seal manufacturing technique which is of a character well understood by those skilled in the art. This technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding the molded container. Further details concerning the technique are available from Rommelag GMBH of Stuttgart, Germany and Weiler Engineering of Elgin, Ill.

In a manner presently to be described, a collapsible container is accessible via a penetrating member 93 that is adapted to pierce closure wall 92a as well as a pierceable membrane 95 which is positioned over closure wall 92a by means of a closure cap 97 which is affixed to the neck portion 94 of container assembly 84 (FIG. 11). As previously described, the basic container 84 is formed using the earlier described aseptic blow-fill technique and the reservoir portion of the container is sealed by the thin closure wall 92a. The pierceable membrane 95 is then positioned over the closure wall and the closure cap 97 is positioned over the pierceable septal membrane and secured to neck portion 94 by any suitable means such as adhesive bonding, sonic or heat welding.

Figure 4B:
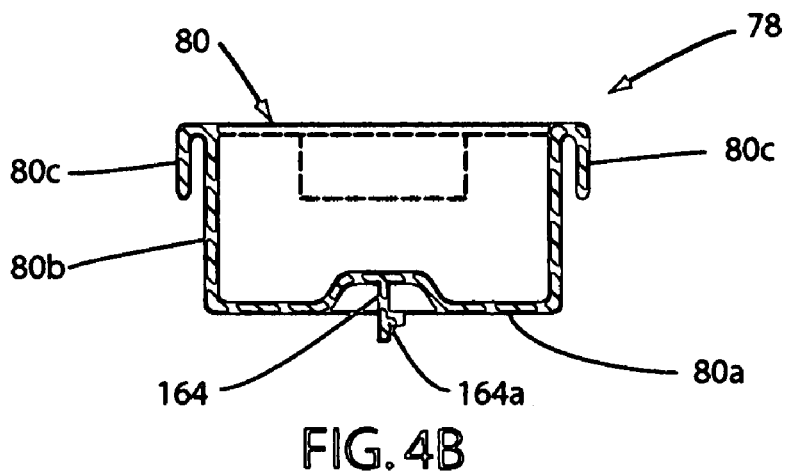
FIG. 4B is a cross-sectional view taken along 4B-4B of FIG. 4A.
Figure 4C:
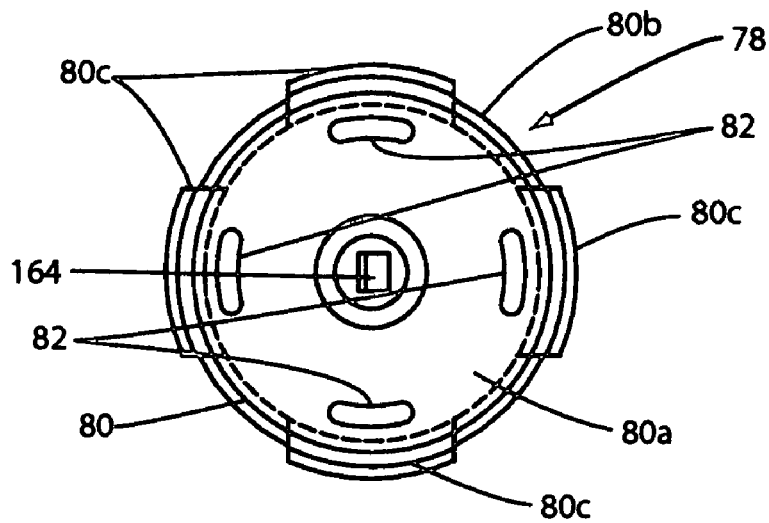
FIG. 4C is a bottom plan view of the carriage assembly shown in FIG. 4B.
Figure 5:
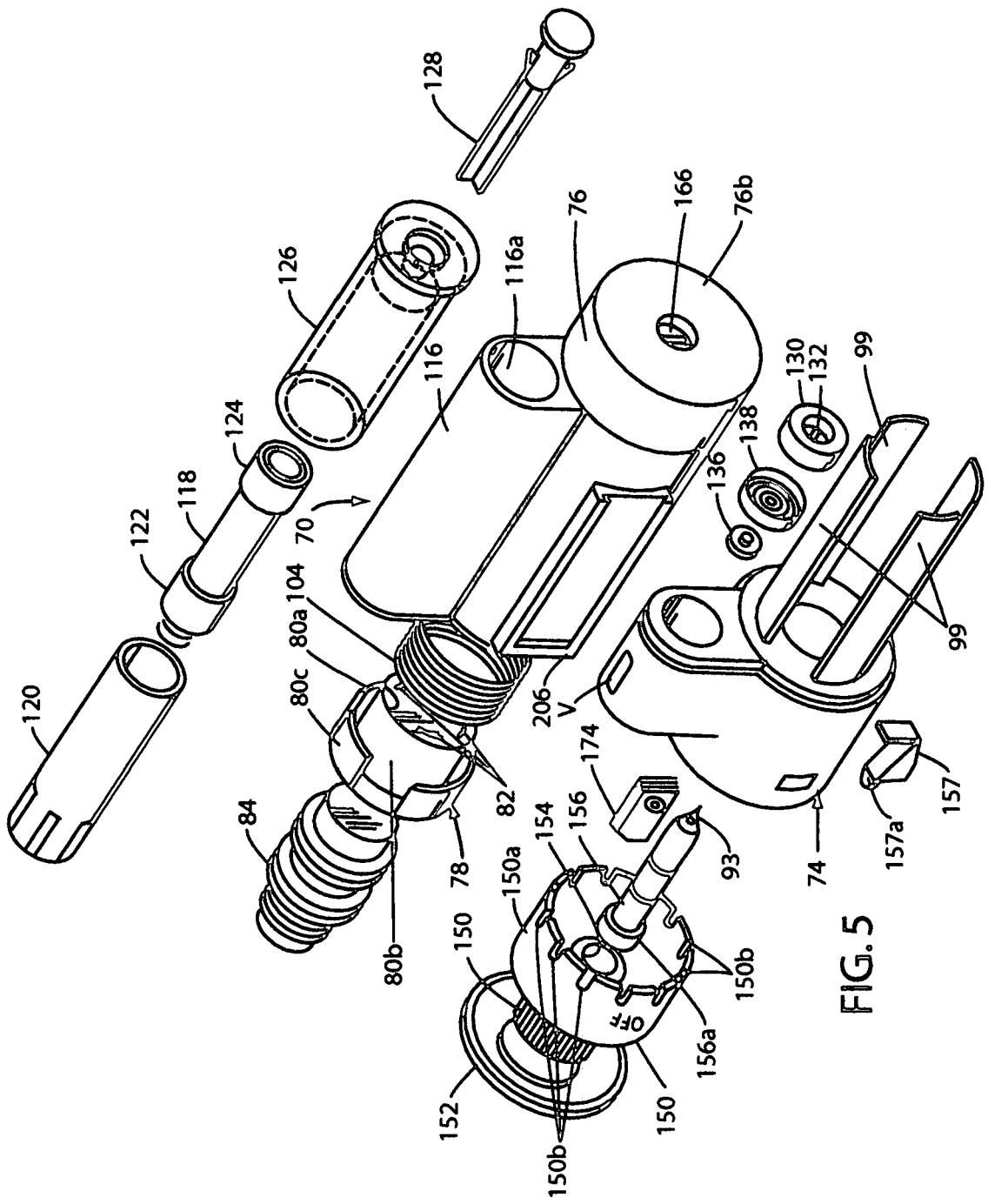
FIG. 5 is a generally perspective, exploded view of the fluid delivery device illustrated in FIG. 4.
Figures 14, 15, 16:
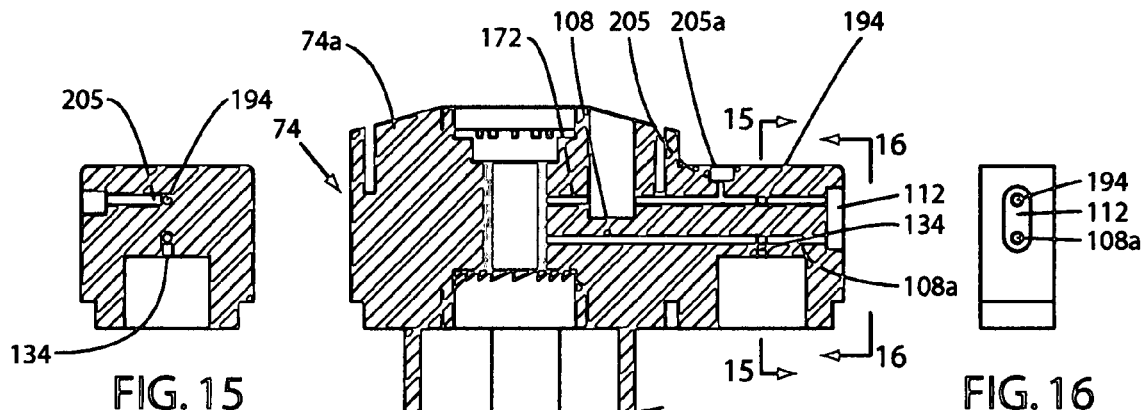
FIG. 14 is a cross-sectional view taken along lines 14-14 of FIG. 13.
FIG. 15 is a cross-sectional view taken along lines 15-15 of FIG. 14.
FIG. 16 is a view taken along lines 16-16 of FIG. 14.
Figure 17:
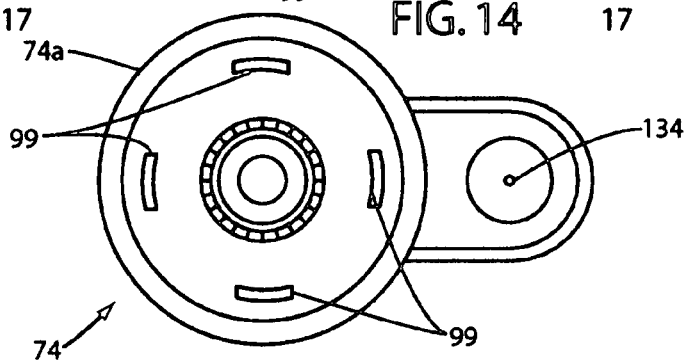
FIG. 17 is a view taken along lines 17-17 of FIG. 14.
Figure 32:
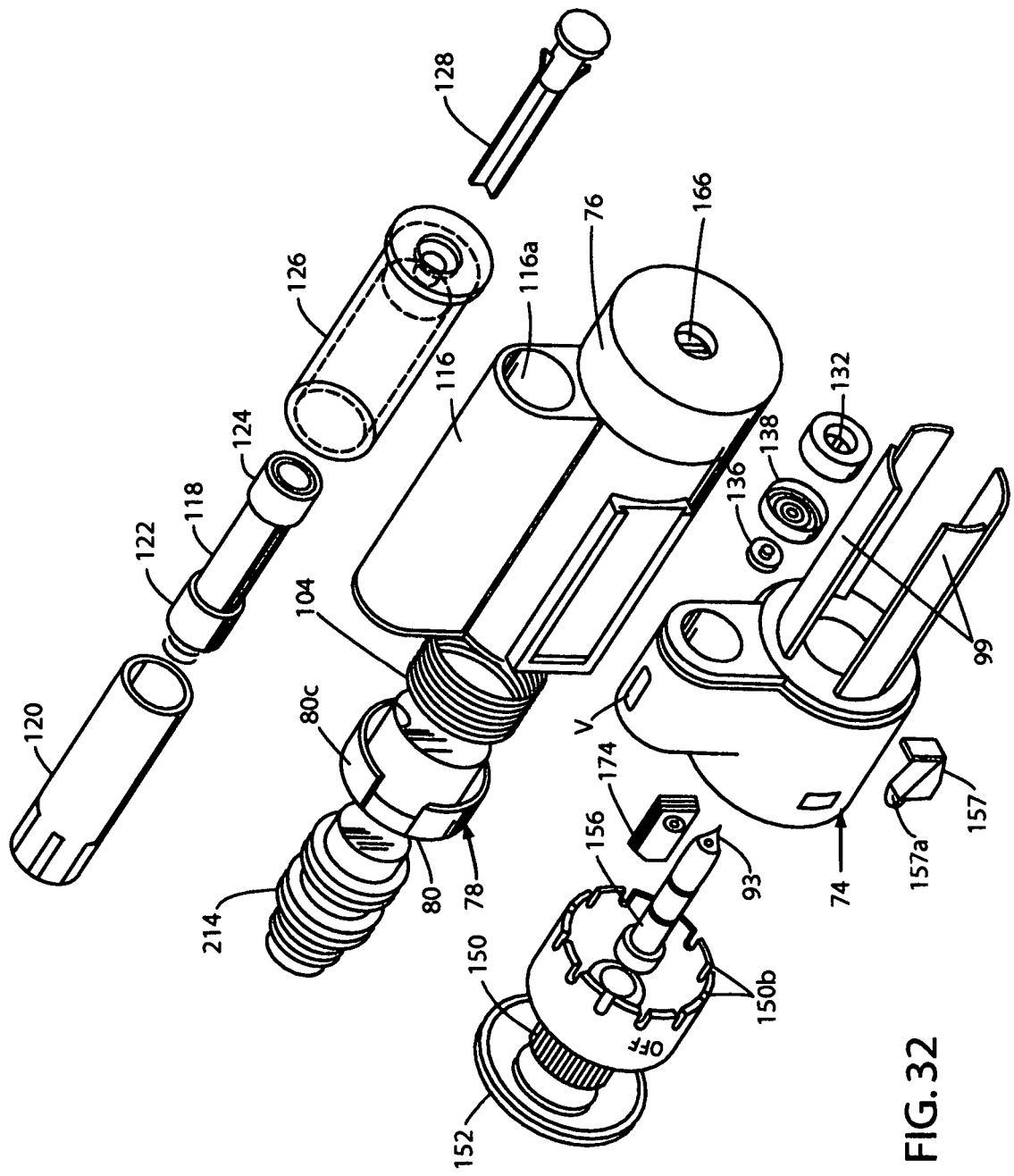
FIG. 32 is a generally perspective, exploded view of the fluid delivery device illustrated in FIG. 31.
Figure 33:
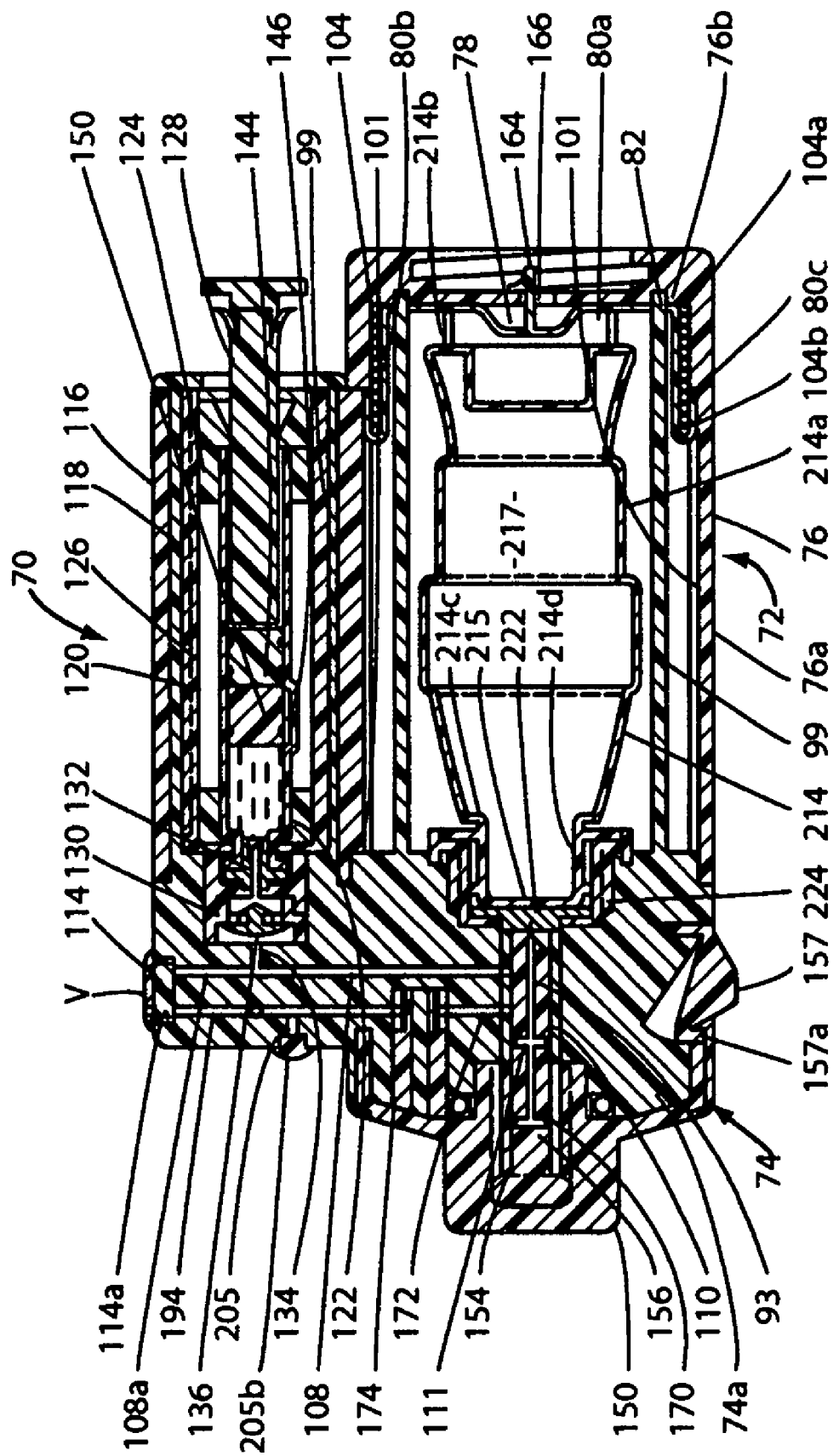
FIG. 33 is a cross-sectional view similar to FIG. 31, but showing the partial filling of the fluid reservoir of the device using one form of the adding means of the invention.
Figure 34:
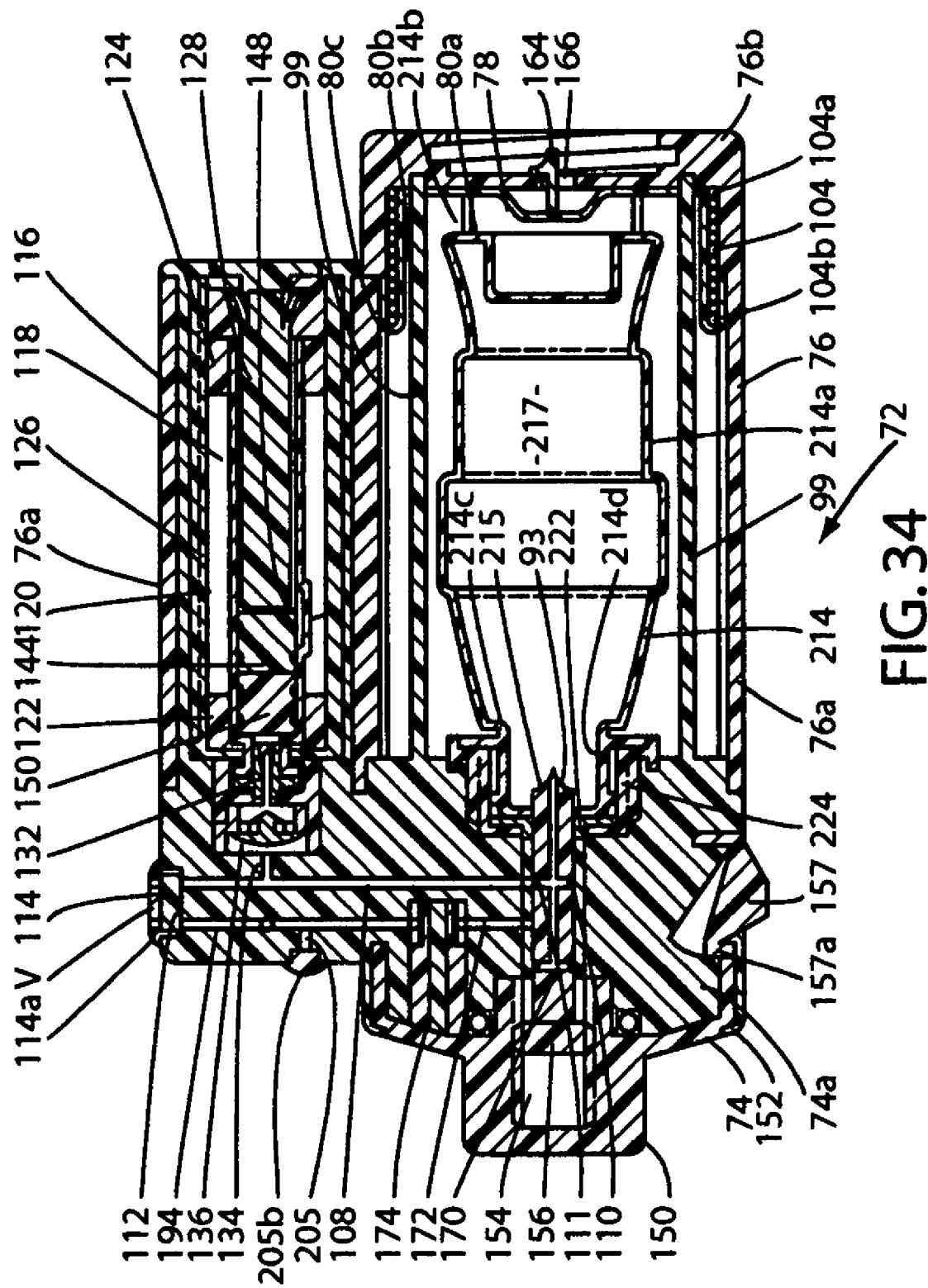
FIG. 34 is a cross-sectional view similar to FIG. 33 but showing the complete filling of the fluid reservoir of the device using one form of the adding means.

An important feature of the invention resides in the provision of novel guide means for guiding travel of carriage assembly 78 between the first position shown in FIG. 4 and the second position shown in FIG. 9. In the present form of the invention this important guide means comprises a plurality of circumferentially spaced guide members 99 which are connected to and extend outwardly from body 74a of control portion 74 (FIGS. 4, 5 and 14). As indicated in the drawings, guide members 99 are slidably received within openings 82 provided in carriage base 80a (FIG. 4) so that, as the carriage assembly travels from its first position toward its second position, guide members 99 precisely guide its travel. Also forming a part of the guide means of the apparatus of the present invention are a plurality of circumferentially spaced guide grooves 101 that are formed on the inner wall of outer housing 76 (FIG. 4).

Figure 12:
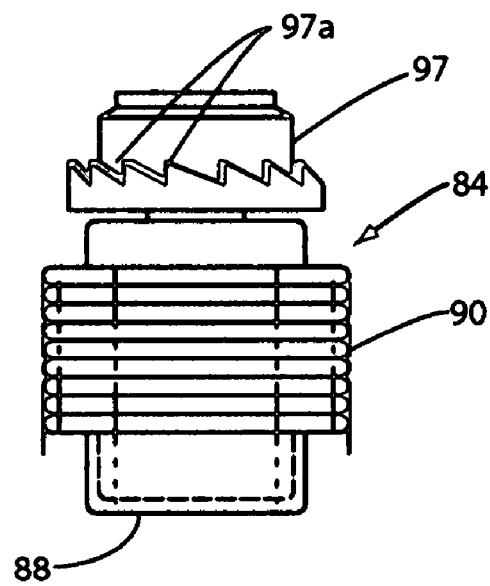
FIG. 12 is a side-elevational view illustrating the appearance of the fluid reservoir in a collapsed configuration.
Figure 13:
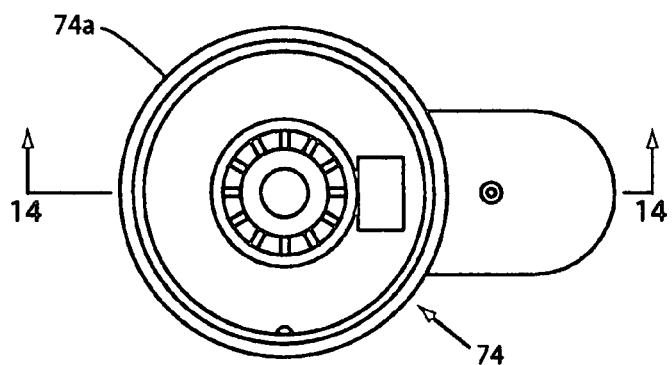
FIG. 13 is an enlarged top plan view of the fluid dispensing device shown in FIG. 1.

To controllably move the carriage assembly from its first position to its second position, novel stored energy means are provided. This novel stored energy means, which is operably associated with carriage assembly 78, is here provided in the form of a coiled spring 104. As illustrated in FIGS. 4 and 9, one end 104a of the coil spring 104 is disposed in engagement with the threaded base portion 76b of reservoir housing 76 and the other end 104b thereof is disposed in engagement with radially outwardly extending flange segments 80c of carriage 80. With this construction, following penetration of the reservoir septum, and when the locking means of the invention is manipulated in a manner to unlock the carriage assembly from base portion 76b of the outer housing, spring 104 will move from its retracted position shown in FIG. 4 to its expanded position shown in FIG. 9, and in so doing will controllably move the carriage assembly from its starting position shown in FIG. 4 to its fully deployed or extended position shown in FIG. 9. As will be described more fully in the paragraphs which follow, as the carriage assembly moves toward its deployed position, the accordion-like side wall 90 of the reservoir defining container will move into the collapsed configuration shown in FIGS. 9 and 12 and in so doing will cause the medicinal fluid contained within the container to be controllably expelled therefrom.

Forming an important aspect of the apparatus of the present invention is adding means carried by portion 76 of housing 72 for adding injectable medicaments to the fluid within the fluid reservoir 85. The details of construction and operation of this important adding means will presently be discussed. As best seen in FIG. 4, body 74a of control portion 74 includes a fluid passageway 108 that is in communication with the fluid passageway of penetrating member 93 via passageways 110 and 111. Proximate its outer extremity 108a, fluid passageway 108 communicates with a cavity 112 formed within control portion 74 (See FIG. 9). Disposed within cavity 112 is a porous filter 114 which comprises a part of the vent means "V" of this latest form of the invention for venting to atmosphere any gasses that would otherwise be trapped within the fluid passageways of the device during the medicament adding step (see also FIGS. 13 through 17). Filter 114, which is of a conventional construction such as a hydrophobic treated, sintered metal or porous membrane, is held in position by a retainer 114a.

Control portion 74 of housing 72 also includes a vial housing 116 having a chamber 116a for telescopically receiving a medicament containing reconstitution-type fill-vial 118. An elongated vial 120, which is disposed within chamber 116a, along with first and second spacers 122 and 124, function to hold vial 118 in a proper position within chamber 116a (See FIG. 5). Vial 120 is telescopically receivable within a vial tube 126, which in turn carries a pusher member 128, the purpose of which will presently be described. Also carried by control portion 74 in close proximity with vial 120 is a needle holding component 130. As shown in FIGS. 4, 21 and 22, needle holding component 130 carries a longitudinally extending, elongated hollow needle 132 having a flow passageway 132a that communicates with fluid passageway 108 via a stub passageway 134 and a conventional check valve 136 which is carried by a check valve housing 138 (FIGS. 5 and 18-20). Vial 118, vial 120, vial tube 126, needle holding component 130 and hollow needle 132 together comprise one form of the adding means of the device of the present invention. The method of operation of this important adding means will presently be described.

Figure 6:
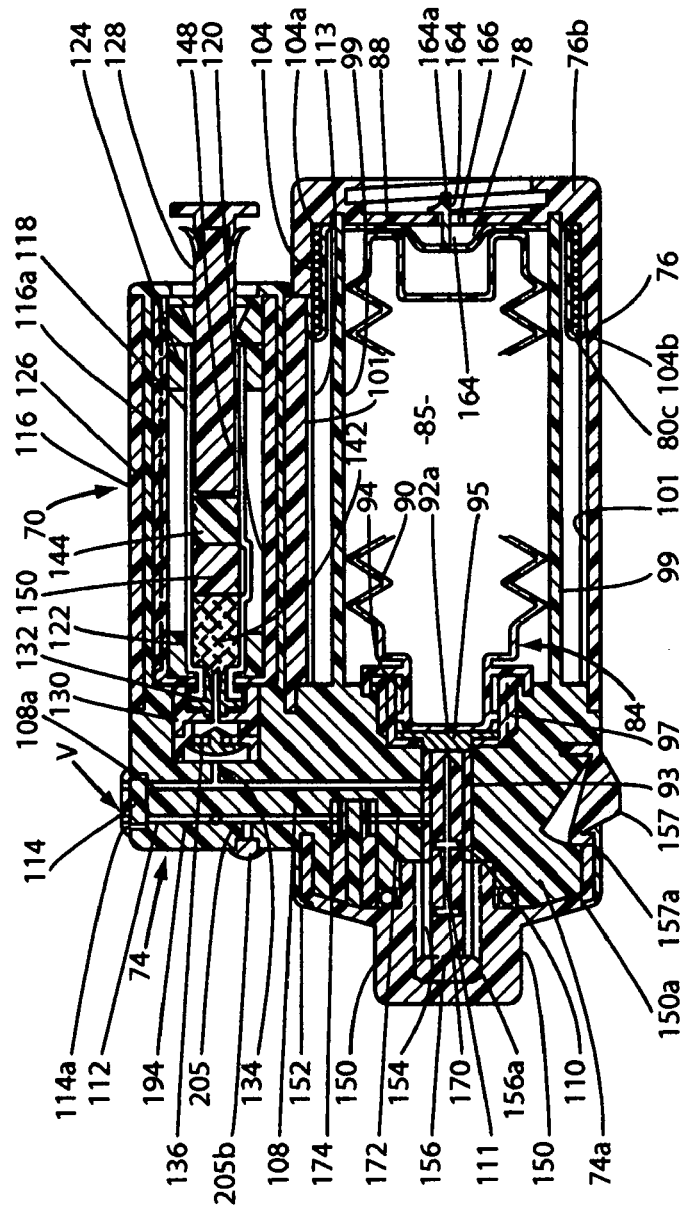
FIG. 6 is a cross-sectional view similar to FIG. 4, but showing the partial filling of the fluid reservoir of the device using one form of the adding means of the invention.
Figure 7:
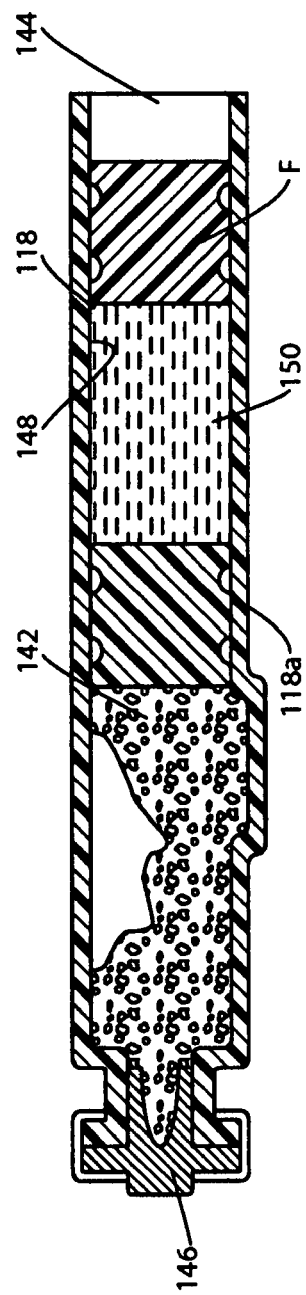
FIG. 7 is an enlarged, cross sectional view of one form of the fill-vial of the adding means.

Referring particularly to FIG. 7, the medicament containing fill-vial 118 comprises a container of special design that uniquely contains a lyophilized drug 142. Vial 118 is sealed at one end by a slidable elastomeric plunger 144 and at the other end by a pierceable septum 146. Formed intermediate the ends of the vial is a raised outer wall by-pass portion 118a, which permits the fluid "F" that is contained within a chamber 148 to bypass a barrier stopper 150 as the barrier stopper is urged inwardly of the container by pressure exerted thereon by the fluid, which is being pushed by plunger 144 resulting from force exerted on pusher element member 128 (see FIG. 6).

A continued inward pressure exerted on plunger 144 will cause fluid "F" to flow past barrier member 150 via the internal passageway defined wall portion 118a so as to reconstitute the lyophilized drug 142. A continued pressure exerted on plunger 144 by the pusher member will cause the reconstituted drug formed by the fluid "F" which has been intermixed with drug to flow through hollow needle 132, into a chamber 138a formed in check valve housing 138 (FIG. 20), past check valve 136, into a stub passageway 134, then into passageway 108 and finally into the device reservoir 85.

Device reservoir 85 and reconstitution medicament containing fill-vial 118 can be of various volumes ranging from about 5 ml to about 50 ml.

To control the flow of medicinal fluid from the adding means into the reservoir 85 and then, during the fluid dispensing step, out of reservoir 85 toward the administration set 162 of the invention, novel flow control means are provided. This novel fluid flow control means, which is housed within the control portion 74 of the device, here comprises two cooperating components, namely a rate control means for controlling the rate of fluid flow from the semi-rigid collapsible reservoir toward the administration set and an operating means for controlling fluid flow from the adding means into the reservoir 85 and then, after the reservoir has been filled, out of reservoir 85 toward the rate control means.

Figure 8:
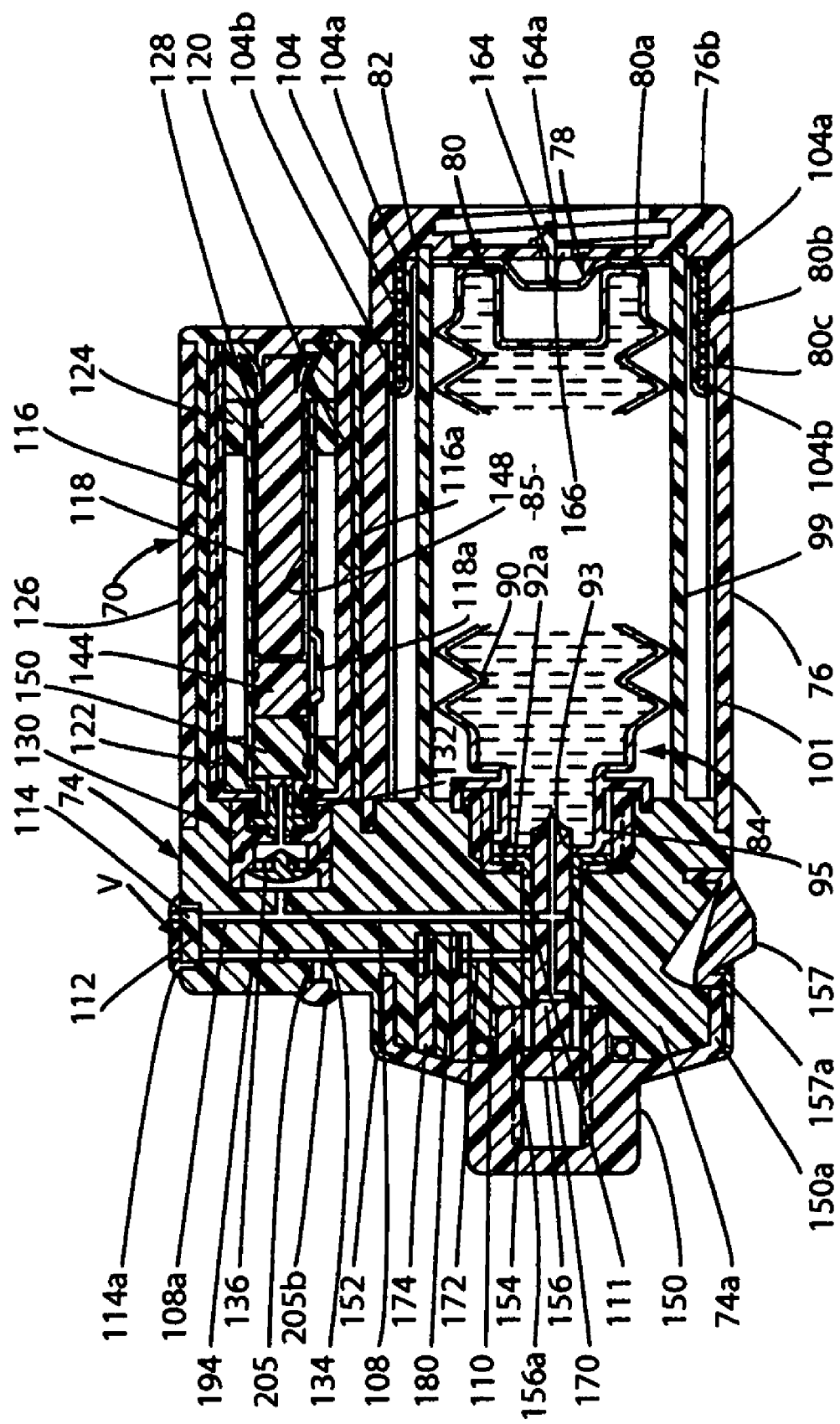
FIG. 8 is a cross-sectional view similar to FIG. 6, but showing the complete filling of the fluid reservoir of the device using one form of the adding means.

Considering first the operating means of the invention, this important means, which first controls fluid flow from the adding means toward the reservoir 85 and subsequently controls fluid flow between collapsible reservoir 85 and the rate control means, here comprises a control knob 150 (FIGS. 23-26) that is rotatably mounted on body 74*a* of control portion 74. As best seen in FIGS. 4 and 5, control knob 150 is held in position on body 74*a* by a knob retaining ring 152. Control knob 150, which is provided with control indicia 153 (FIGS. 3 and 23), has an axial bore 154 having threads 154*a* (See FIGS. 24 through 26) that threadably receive the head portion 156*a* of an elongated needle housing 156 that carries penetrating member 93 (FIGS. 4 and 8). With this construction, an initial rotation of knob 150 will cause the needle housing 156 to controllably move from the position shown in FIG. 4 to the fill position shown in FIG. 8, wherein fluid passageway 111 aligns with fill passageway 108 formed in control body portion 74*a*. As indicated in FIG. 8, this initial rotation of control knob 150 will also cause penetrating member 93 to pierce both septal membrane 95 as well as closure wall 92*a* of the reservoir container. This movement of the housing 156 and the penetrating member 93 opens fluid communication between the fill-vial 118 and the fluid reservoir 85 via penetrating needle 93, the opened check valve 136, stub passageway 134, fill passageway 108, stub passageway 111 and the internal fluid flow passageway of penetrating member 93. In the manner previously discussed, an inward force exerted on pusher member 128 will cause the fluid "F" to flow past barrier member 150 via the internal by-pass passageway defined by wall portion 118*a* so as to reconstitute the lyophilized drug 142. A continued pressure exerted on plunger 144 by the pusher member will cause the reconstituted drug formed by the fluid "F", which has been intermixed with the drug, to flow through penetrating needle 132 and then on to the fluid reservoir 85. After the reservoir is filled, check valve 136 will return to its initial closed position shown in FIGS. 4 and 18 blocking reverse fluid flow from collapsible reservoir 85 toward fill-vial 118.

To prevent accidental rotation of control knob 150, the operating means further includes indexing means, here provided in the form of an indexing button 157. This important indexing means functions to prevent rotation of the control knob until the indexing button, which is pivotally mounted on the side of the control portion of the device (FIG. 4), is pivoted inwardly. As illustrated in FIGS. 5, 24 and 25 of the drawings, the skirt portion 150*a* of the control knob is provided with a plurality of circumferentially spaced notches 150*b* that closely receive a locking tab 157*a* (FIG. 5) formed on indexing button 157 when the button is biased toward its outward locking position. To accomplish the initial rotational step, described in the preceding paragraph, the indexing button 157 is pushed inwardly to move the locking tab 157*a* out of engagement with the notch within which it resides and the control knob is rotated from the "OFF" position (FIG. 3) to the "FILL" position. Release of the indexing button will then cause the outwardly biased locking tab 157*a* to move into engagement with an appropriate locking notch so as to lock the control knob in the "FILL" position.

After the diluent reservoir-filling step has been completed in the manner previously described, the fluid contained within the field reservoir can be dispensed to the patient by once again pivoting the indexing button 157 inwardly to move the locking tab 157*a* out of engagement with the notch within which it resides. This done, the control knob can be further rotated to the "DISP." position thereby causing the needle housing 156 to controllably move from the position shown in FIG. 8 to the fluid delivery position shown in FIG. 9. In this position fluid passageway 170 aligns with dispensing passageway 172 formed in control body portion 74*a* so that fluid can flow from reservoir 85 toward the administration set 162 via the flow rate control means of the invention the character of which will presently be described.

To cause the fluid to flow from reservoir 85 toward the flow rate control means, the locking means of the invention must be manipulated in a manner to release the carriage assembly from base wall 76*b* of reservoir housing 76. In this regard, as best seen in FIGS. 4B and 4C, the carriage locking means includes a locking member 164 having a yieldably deformable locking tab 164*a* which extends through a strategically shaped opening 166 provided in the base wall 76*b* of reservoir housing 76 (see FIGS. 4 and 5). With this construction, an inward force exerted on the locking member will deform the locking tab 164 in a manner to permit it to pass through the opening 166 and in so doing release the carriage from the base wall 76*b*. Release of the carriage will permit the stored energy means, or coiled spring 104, to move the carriage from a position shown in FIG. 4 into the position shown in FIG. 9. As the semi-rigid accordion-like side wall of the container collapses due to the urging of the coiled spring, the medicinal fluid contained within the container will be controllably expelled therefrom and will flow toward the fluid passageway of penetrating member 93 which has now moved into the position shown in FIG. 9 of the drawings. From the fluid passageway of penetrating member 93, fluid will flow into a stub passageway 170 formed in needle housing 156. As illustrated in FIG. 9, stub passageway 170 is now aligned with a passageway 172 which forms the inlet to the fluid rate control means of the invention.

The important fluid rate control means of the invention, which is illustrated in FIGS. 9A through 9F of the drawings, comprises a rate control housing 174, which includes a front cover 176 having an inlet 176*a* and an outlet 176*b*. Rate control housing 174 also includes a back cover 178 having an inlet 178*a* and an outlet 178*b*. Disposed between the front and back cover is a novel rate control plate 180 having a uniquely configured, circuitous fluid flow channel 180*a* formed on the first surface 180*b* thereof and a substantially linear fluid flow channel 180*c* formed on the second surface 180*d* thereof.

With the construction described in the preceding paragraphs, as the accordion-like side wall of the fluid container collapses in a controlled manner, fluid will flow from reservoir 85 into the flow passageway of penetrating member 93, into stub passageway 170 and then into the inlet passageway 176*a* of the rate control means. From passageway 172, the fluid will flow into the inlet 176*a* of front cover 176 and then into inlet 182 of rate control plate 180. The fluid will then flow through the rate control channel 180*a*, out the outlet 184 of the rate control channel and into the inlet 186 of flow control channel 180*c*. Next, the fluid will flow through flow control channel 180*c* and outwardly thereof through outlet 188. From outlet 188 the fluid will flow into inlet 178*a* of back cover 178, outwardly through outlet 178*b* thereof and then into an elongated passageway 194 formed in body 74*a* of control portion 74. From the elongated channel 194 the fluid will flow onward to the administration set 162 and then to the patient. It is apparent that by varying the geometry, including the length, width and depth of the flow control channel 180*c*, the rate of fluid flow to the administration set and to the patient can be readily varied.

As best seen in FIG. 3, administration set 162 is sealably connected to the control portion 74 by a connector 195 so that the proximal end 162*a* of administration line 162 of the administration set is in communication with an outlet fluid passageway 194. Disposed between the proximal end 162a and the distal end 162b of the administration line are a conventional clamp 197, a conventional gas vent and a conventional filter 199 and an injector site 198. Provided at the distal end 162b of the administration line is a luer connector 201 and luer cap 203 of conventional construction (See FIG. 1).

To accomplish residual drug recovery from reservoir 85 as may be required, recovery means are provided. In this regard, as best seen in FIGS. 4 and 14 a stub passageway 205 formed in body 74a also communicates with fluid passageway 194. Stub passageway 205 also communicates with a cavity 205a formed in body 74a (FIG. 14). Sealably mounted within cavity 205a is a non-coring pierceable septum 205b (FIG. 4) which is pierceable by the needle of a conventional syringe which can be used to accomplish residual drug recovery from reservoir 85.

As illustrated in FIG. 1, housing 76 is provided with a belt clip receiving member 206 to which a belt clip 208 can be slidably interconnected. When the belt clip 208 is connected with receiving member 206 the device can be conveniently carried on the user's belt during the medicament dispensing step.

Referring to FIGS. 28 through 38, an alternate form of the dispensing device of the present invention for dispensing medicaments to a patient is there shown and generally designated by the numeral 212. This alternate form of dispensing device is similar in most respects to that shown in FIGS. 1 through 27 and like numerals are used in FIGS. 28 through 38 to identify like components. The major difference between this latest embodiment of the invention and that shown in FIGS. 1 through 27 resides in the differently configured reservoir defining container 214. As shown in FIGS. 31 and 37 container 214, rather than being in the nature of the collapsible container having a bellows-like sidewall, comprises a collapsible, bottle-like container having a collapsible side wall 214a that is movable from the expanded, starting configuration shown in FIG. 31 to the collapsed configuration shown in FIGS. 35 and 38. This important reservoir defining container here includes, in addition to sidewall 214a, an interconnected bottom wall 214b, an interconnected top wall 214c and an interconnected neck portion 214d which is sealed at the time of manufacture by a thin closure wall 215. Neck portion 214d forms a part of the novel reservoir access means of the invention. Collapsible container 214 defines a fluid reservoir 217 that, in a manner presently to be described, is accessible via a penetrating member 93 that is adapted to pierce closure wall 215 as well as a pierceable membrane 222 which is positioned over closure wall 215 by means of a closure cap 224 which is affixed to the neck portion 214d of container assembly (see also FIG. 37).

As best seen in FIGS. 28 through 31 of the drawings, this alternate form of the dispensing device of the invention comprises a housing 72, that is substantially identical to that shown in FIG. 1 and includes a control portion 74 and a reservoir housing 76 having a generally cylindrically shaped wall portion 76a and a base portion 76b.

Disposed within wall portion 76a is the carriage assembly 78 which is of identical construction and operation to that previously described and is releasably locked in its first position by locking means also identical in construction and operation to the locking means previously described herein. Carried by carriage assembly 78 is the previously described reservoir defining container 214.

As in the last described embodiment of the invention, the basic container 214 is formed using the earlier described aseptic blow-fill seal technique and the reservoir portion of the container is sealed by the thin closure wall 215. The pierceable membrane 222 is then positioned over the closure wall 215 and the cap 224 is positioned over the pierceable membrane and secured to neck portion by any suitable means such as adhesive bonding or sonic welding.

Figure 35:
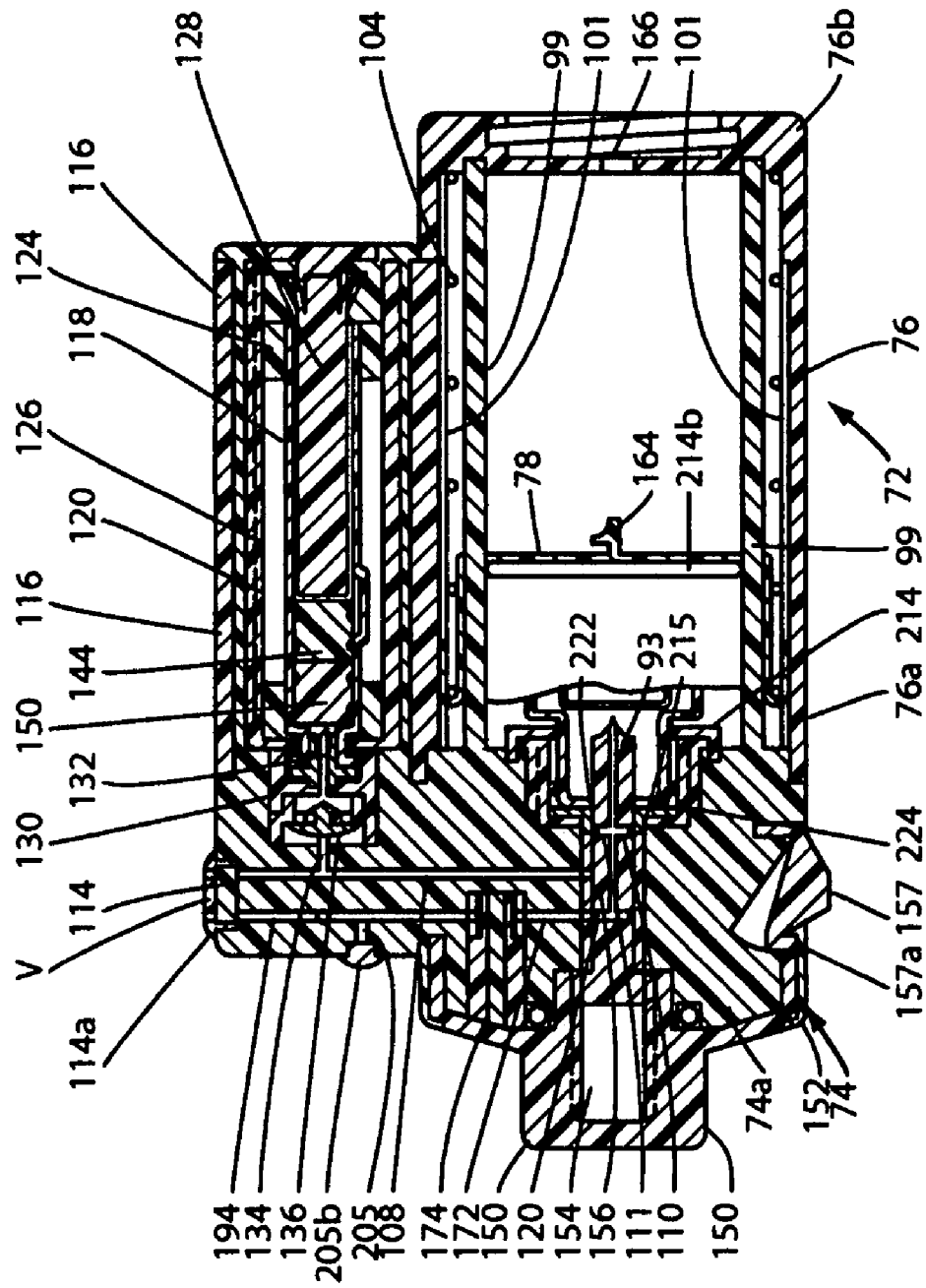
FIG. 35 is a cross-sectional view similar to FIG. 34, but illustrating the fluid delivery step wherein the fluid reservoir of this latest form of the invention is collapsed by the stored energy means and the fluid is caused to flow toward the patient.
Figure 42:
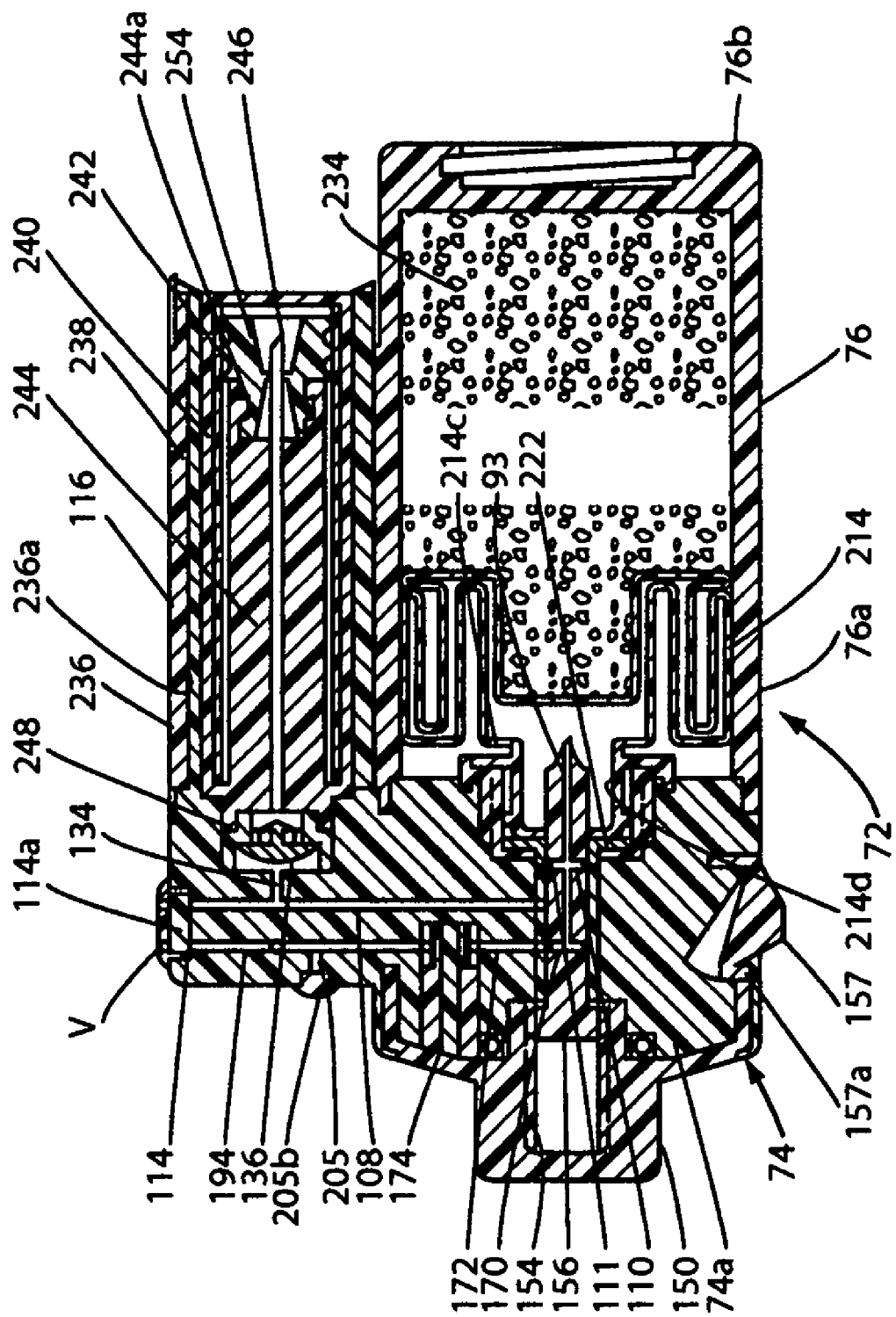
FIG. 42 is a cross-sectional view similar to FIG. 40 illustrating the appearance of the fluid reservoir of the fluid dispensing device in a collapsed configuration.

As before, novel guide means are provided for guiding travel of carriage assembly 78 between the first position shown in FIG. 31 and the second position shown in FIG. 35. This important guide means is of identical construction and operation to that previously described herein.

Once again, in order to controllably move the carriage assembly from its first position to its second position, novel stored energy means are provided. This novel stored energy means, which is operably associated with carriage assembly 78, is here provided in the form of a coiled spring 104, which is also identical construction and operation to that previously described.

As in the earlier described embodiment of the invention, the adding means of the invention which is carried by portion 76a of housing 72 functions to controllably add selected medicaments to the fluid contained within the fluid reservoir 217. The adding means of this latest embodiment of the invention is also identical in construction and operation to that previously described. Following filling of the reservoir in the manner previously described and the piercing of closure wall 215 and pierceable membrane 222 by the penetrating member 93, the locking means of the invention can be manipulated in a manner to unlock the carriage assembly from base portion 76b of portion 76a of housing 72. When this is done, spring 104 will move from its retracted position shown in FIG. 31 to its expanded position shown in FIG. 35 and in so doing will controllably move the carriage assembly from its starting position to the position shown in FIG. 35. As the container collapses, the medicinal fluid contained within the container will be controllably expelled therefrom.

To further control the flow of medicinal fluid from reservoir 217 toward the administration set 162 of the invention and then on to the patient, flow control means are provided. These important flow rate control means are identical to those previously described in connection with the embodiment of FIGS. 1 through 27 and will not here be further discussed.

From the flow rate control means the fluid will flow into elongated passageway 194 formed in body 74a of control portion 74 and from there will flow onward to the administration set 162 and then to the patient. As before, by varying the geometry, including the length, width and depth of the flow rate control channel 180c of the flow rate control means, the rate of fluid flow to the patient can be readily varied.

Referring to FIGS. 39 through 42, an alternate form of the dispensing device of the present invention for dispensing medicaments to a patient is there shown and generally designated by the numeral 232. This alternate form of dispensing device is similar in most respects to that shown in FIGS. 28 through 38 and like numerals are used in FIGS. 39 through 42 to identify like components. The major differences between this latest embodiment of the invention and that shown in FIGS. 28 through 38 resides in the differently configured adding means and the totally different stored energy means for controllably expelling the medicinal fluid contained within the container of dispensing device.

More particularly, rather than being of a mechanical spring, the novel stored energy means of this latest form of the invention comprises a compressible, expandable sponge-like configuration, which is generally designated in the drawings by the 234. This unique stored energy source can, by way of non-limiting example, comprise a microporous, mesoporous, macroporous, ordered structure and can be constructed from Silicone foam (SI), Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluoroethylene (PTFE) and porous cellulose acetate. The stored energy source can also be constructed from various metallized, porous, sponge-like materials.

As in the last described embodiment of the invention, the basic container 214 is formed using the earlier described aseptic blow-fill seal technique and the reservoir portion of the container is sealed by the thin closure wall 215. The pierceable membrane 222 is then positioned over the closure wall 215 and the cap 224 is positioned over the pierceable membrane and secured to neck portion by any suitable means such as adhesive bonding or sonic welding.

Collapsible container 214 includes a side wall 214a, a bottom wall 214b and a top wall 214c to which the neck portion 214d is secured by any suitable means such as adhesive bonding, sonic or heat welding.

As before, to control the flow of medicinal fluid from the adding means of the invention into the reservoir 217 and then, during the fluid dispensing step, out of reservoir 214 toward the administration set 162 of the invention, novel flow control means are provided. This novel fluid flow control means, which is housed within the control portion 74 of the device, is substantially identical in construction and operation to that previously described and includes operating means for controlling fluid flow from the adding means into the fluid reservoir.

The adding means, of the invention, which is carried by portion 76a of housing 72, is of a different construction and operation to that previously described. More particularly, as illustrated in FIG. 40, control portion 74 of housing 72 includes a housing 236 having a chamber 236a. A pusher member 238, the purpose of which will presently be described, is telescopically receivable over an elongated vial 240, which is also disposed within chamber 236a. Telescopically receivable within vial 240 is an injectable medicament containing fill-vial 242 (see also FIG. 41). Vial 240 includes an elongated support 244, which is disposed within vial chamber 240a (FIG. 41). Support 244, includes a threaded end portion 244a and carries a longitudinally extending, elongated hollow needle 246 having a flow passageway that communicates with a check valve housing 248 formed proximate one end of the vial. The method of operation of this alternate form of adding means will presently be described.

Referring particularly to FIG. 41, the medicament containing fill-vial 242 includes a body portion 242a, having a fluid chamber 250 for containing the injectable fluid medicament "F". Chamber 250 is provided with a first open end 250a and second closed end 250b. First open end 250a is sealably closed by closure means here provided in the form of an externally threaded elastomeric plunger 254, which is telescopically movable within the vial from a first location, where the plunger is disposed proximate first open end 250a to a second, device-fill location where the plunger is disposed proximate second closed end 250b.

In carrying out the reservoir-fill step, vial 242 is first inserted into chamber 240a of the vial 240 and the threaded end 254a of plunger 254 is threadably interconnected with threaded end 244a of support 244. As the components are thusly interconnected, the sharp end of the elongated needle 246 will pierce the central wall 254b of the elastomeric plunger. A continuous pushing movement of the vial 242 into chamber 240a by means of the pusher member 238 will cause the support 244 to move the elastomeric plunger inwardly of the vial chamber in a direction toward the second, or closed, end 250b of the vial chamber. As the plunger is moved inwardly of the vial, the fluid "F" contained within the vial chamber will be expelled therefrom into the hollow elongated needle 246. As best seen in FIG. 40, the fluid will then flow past conventional elastomeric umbrella-type check valve 136, which is mounted within check valve housing 248 of the vial. Next, the fluid will flow into stub passageway 134 and thence into passageway 108. Umbrella-type check valve 136 functions in a conventional manner to control fluid flow from the elongated hollow needle 246 toward fluid passageway 108. From passageway 108, the fluid will flow into inlet passageway 111 and then into reservoir 217 of the container.

Following filling of the reservoir in the manner previously described, the operating means is used to control the fluid flow from the collapsible reservoir toward the rate control means and then onward toward the administration set. More particularly, following the piercing of closure wall 215 and pierceable membrane 222 by the penetrating member 93, the compressible, expandable sponge 234 will move from its compressed position shown in FIG. 40 to its expanded position shown in FIG. 42 and in so doing will controllably collapse the container 214. As the container collapses, the medicinal fluid contained within the container will be controllably expelled therefrom.

To further control the flow of medicinal fluid from reservoir 214 toward the administration set 162 of the invention and then on to the patient, flow rate control means are provided. These important flow rate control means, which comprise a part of the operating means, are identical to those previously described in connection with the embodiment of FIGS. 28 through 38 and will not here be further discussed.

From the flow rate control means of the flow control means, the fluid will flow into elongated passageway 194 formed in body 74a of control portion 74 and from there will flow onward to the administration set 162 and then to the patient. As before, by varying the geometry, including the length, width and depth of the flow rate control channel 180c of the flow rate control means, the rate of fluid flow to the patient can be readily varied.

Referring to FIGS. 43 through 46, still another form of the dispensing device of the present invention for dispensing medicaments to a patient is there shown and generally designated by the numeral 262. This alternate form of dispensing device is similar in many respects to that shown in FIGS. 39 through 42 and like numerals are used in FIGS. 43 through 46 to identify like components. The major difference between this latest embodiment of the invention and that shown in FIGS. 39 through 42 resides in the differently configured reservoir-adding means.

As shown in FIGS. 44 and 46, once again collapsible container 214 has a sidewall 214a that is movable from the expanded, starting configuration shown in FIG. 44 to the collapsed configuration shown in FIG. 46. This important reservoir defining container here includes, in addition to sidewall 214a, an interconnected bottom wall 214b, an interconnected top wall 214c and an interconnected neck portion 214d which is sealed at the time of manufacture by a thin closure wall 215. Neck portion 214d forms a part of the novel reservoir access means of the invention. Collapsible container 214 defines a fluid reservoir 217 that, in the manner previously described, is accessible via a penetrating member 93 that is adapted to pierce closure wall 215 as well as a pierceable membrane 222 which is positioned over closure wall 215 of by means of a closure cap 224 which is affixed to the neck portion 214d of the container assembly.

Figure 46:
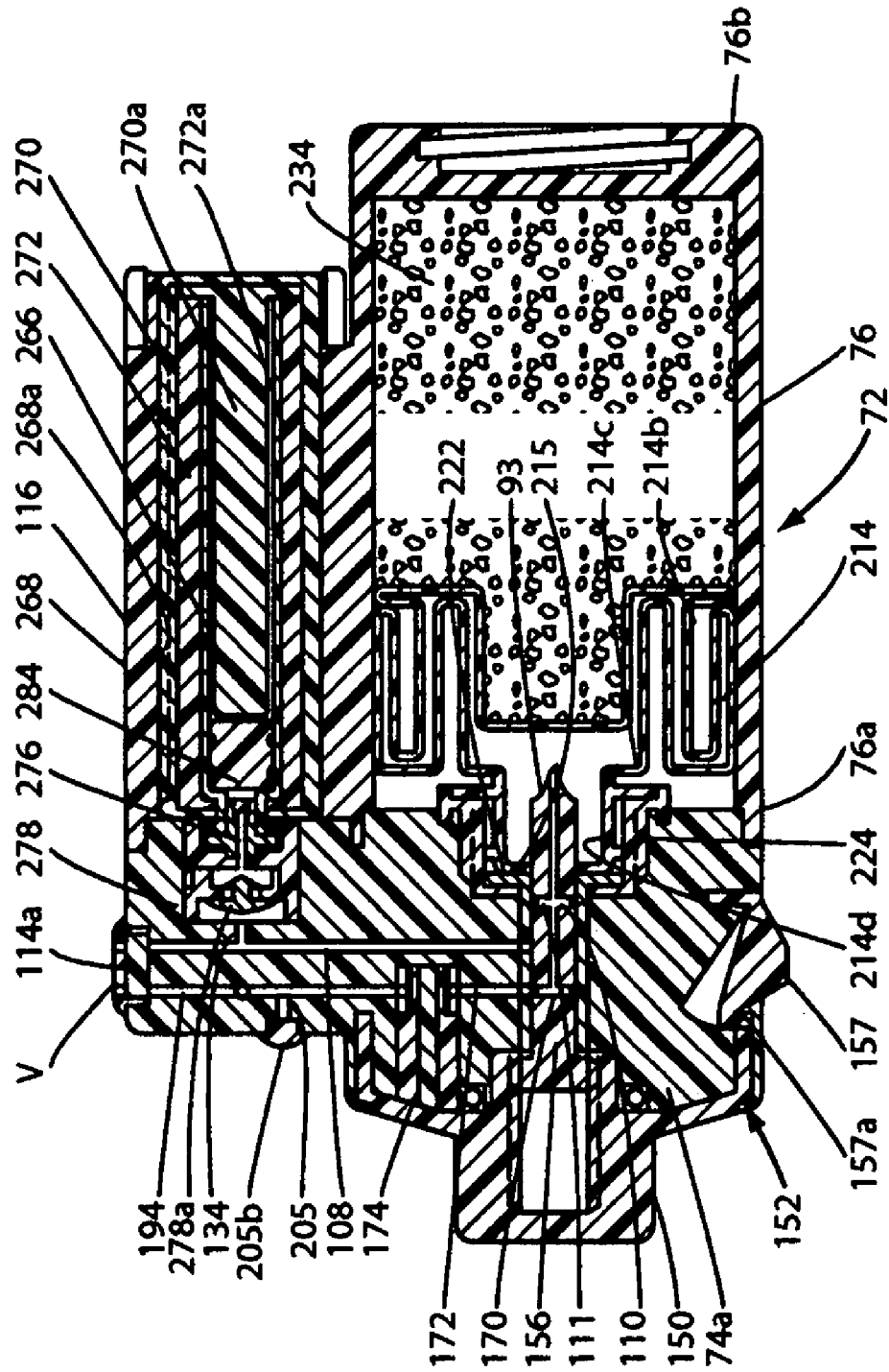
FIG. 46 is a cross-sectional view similar to FIG. 44 illustrating the appearance of the fluid reservoir of the fluid dispensing device in a collapsed configuration.

As best seen in FIGS. 44 and 46 of the drawings, this alternate form of the dispensing device of the invention comprises a housing 72, that is substantially identical to that shown in FIG. 40 and includes a control portion 74 and a reservoir housing 76 having a generally cylindrically shaped wall portion 76a and a base portion 76b.

As in the last described embodiment of the invention, the stored energy means here comprises a compressible, expandable sponge-like configuration, which is of substantially identical construction to that described in connection with the embodiment of FIGS. 40 and 41, is generally designated in the drawings by the numeral 234. As before stored energy source 234 can comprise a microporous, mesoporous, macroporous, ordered structure and can be constructed from metal, Silicone (SI), Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluoroethylene (PTFE) and porous cellulose acetate or other metallic or sponge materials, including open cell and closed cell sponge materials.

As in the last described embodiment of the invention, the reservoir defining assembly 236 here comprises a semi-rigid collapsible container 214, which is of similar construction to that previously described and is carried within portion 76a of housing 76 in the manner illustrated in FIG. 44. Collapsible container 214, which is formed using the earlier described aseptic blow-fill seal technique, includes a top wall 214c, a bottom wall 214b and a collapsible side wall 214a, which cooperate to define a fluid reservoir 217. Connected to top wall 214c is a neck portion 214d that is sealed by a closure wall 215. A pierceable membrane 222 is positioned over the closure wall 215 and a cap 224 is positioned over the pierceable membrane and is secured to neck portion by any suitable means such as adhesive bonding or sonic welding.

As before, to control the flow of injectable medicinal fluid from the adding means of the invention into the reservoir 217 and then, during the fluid dispensing step, out of reservoir 217 toward the administration set 162 of the invention, novel flow control means are provided. This novel fluid flow control means, which is housed within the control portion 74 of the device, is substantially identical in construction and operation to that previously described and includes operating means for controlling fluid flow from the adding means into the reservoir 217.

The adding means, of this latest form of the invention, which is carried by portion 76a of housing 72, rather than being in the nature of a shell-vial, here comprises a generally conventional cartridge-vial 266 (FIG. 45).

As illustrated in FIG. 44, the control portion 74 of housing 72 includes a housing 268 having a chamber 268a. A pusher member 270, the purpose of which will presently be described, is telescopically receivable over an elongated vial 272, which is also disposed within chamber 268a. Telescopically receivable within chamber 272a of a vial 272 is the previously mentioned cartridge-vial 266 (see also FIG. 45). Disposed within vial chamber 272a is a support 274, which carries a longitudinally extending, hollow needle 276 having a flow passageway that communicates with a check valve housing 278a formed proximate one end of the vial. The method of operation of this alternate form of adding means will presently be described.

As best seen in FIG. 45, cartridge fill-vial 266 comprises a hollow glass or plastic body portion 266a that defines a fluid chamber 280. Vial 266 has an open first end 266c and a second end 266b that is closed by a pierceable, elastomeric septum 282. An elastomeric plunger 284 is reciprocally movable within fluid chamber 280. During the reservoir-fill step, hollow needle 276 is adapted to pierce septum 282 when the fill-vial 266 is inserted into chamber 272a and pushed into the position shown in FIG. 44.

With the cartridge-vial 266 positioned within chamber 272a, a continuous pushing movement of the pusher member 270 into housing chamber 268a will cause pusher 270a of the pusher member 270 to move the elastomeric plunger 284 inwardly of the fluid chamber 280 in a direction toward the second, or closed end 266b of the vial. As the plunger is moved inwardly of the fluid chamber 280, the fluid "F" contained within the fluid chamber will be expelled therefrom into the hollow needle 276. As best seen in FIG. 46, the fluid will then flow past conventional elastomeric umbrella-type check valve 278a, which is mounted within check valve housing 278 of the vial. Next, the fluid will flow into stub passageway 134 and thence into passageway 108. Umbrella-type check valve 278a functions in a conventional manner to control fluid flow from the hollow needle 276 toward fluid passageway 108. From passageway 108, the fluid will flow into inlet passageway 111 and then into reservoir 217 of the container.

Following filling of the reservoir in the manner previously described, the operating means is used to control the fluid flow from the collapsible reservoir toward the rate control means and then onward toward the administration set. More particularly, following the piercing of closure wall 215 and pierceable membrane 222 by the penetrating member 93, the compressible, expandable sponge 234 will move from its compressed position shown in FIG. 44 to its expanded position shown in FIG. 46 and in so doing will controllably collapse the container 214. As the container collapses in a uniformly controlled manner, the medicinal fluid contained within the container will be controllably expelled therefrom.

To further control the flow of medicinal fluid from reservoir 214 toward the administration set 162 of the invention and then on to the patient, flow rate control means are provided. These important flow rate control means, which comprise a part of the operating means, are identical to those previously described in connection with the embodiment of FIGS. 28 through 38 and will not here be further discussed.

From the flow rate control means of the flow control means, the fluid will flow into elongated passageway 194 formed in body 74a of control portion 74 and from there will flow onward to the administration set 162 and then to the patient. As before, by varying the geometry, including the length, depth and width of the flow control channel 180c of the flow rate control means, the rate of fluid flow to the patient can be readily varied.

Referring to FIGS. 47 through 50, still another form of the dispensing device of the present invention for dispensing medicaments to a patient is there shown and generally designated by the numeral 292. This alternate form of dispensing device is similar in many respects to that shown in FIGS. 43 through 46 and like numerals are used in FIGS. 47 through 50 to identify like components. The major difference between this latest embodiment of the invention and that shown in FIGS. 43 through 46 resides in the differently configured reservoir defining assembly 294 for containing the fluid to be dispensed to the patient.

As illustrated in FIG. 48, control portion 74 of housing 72 includes a vial housing 268 having a chamber 268a for telescopically receiving a medicament containing fill-vial 266, which is identical to the cartridge-vial previously described.

Reservoir defining assembly 294 that defines fluid reservoir 295 here comprises a top wall 296, a bottom wall 298 and an accordion-like side wall 300. Connected to top wall 296 is a neck portion 302 that is sealed by a closure wall 302a. A pierceable membrane 304 is positioned over the closure wall 302a and a cap 306 is positioned over the pierceable membrane and is secured to neck portion by any suitable means such as adhesive bonding or sonic welding.

In the preferred form of the invention, reservoir defining assembly 294 is formed in accordance with an aseptic blow-fill-seal technique which is of a character well understood by those skilled in the art.

Figure 50:
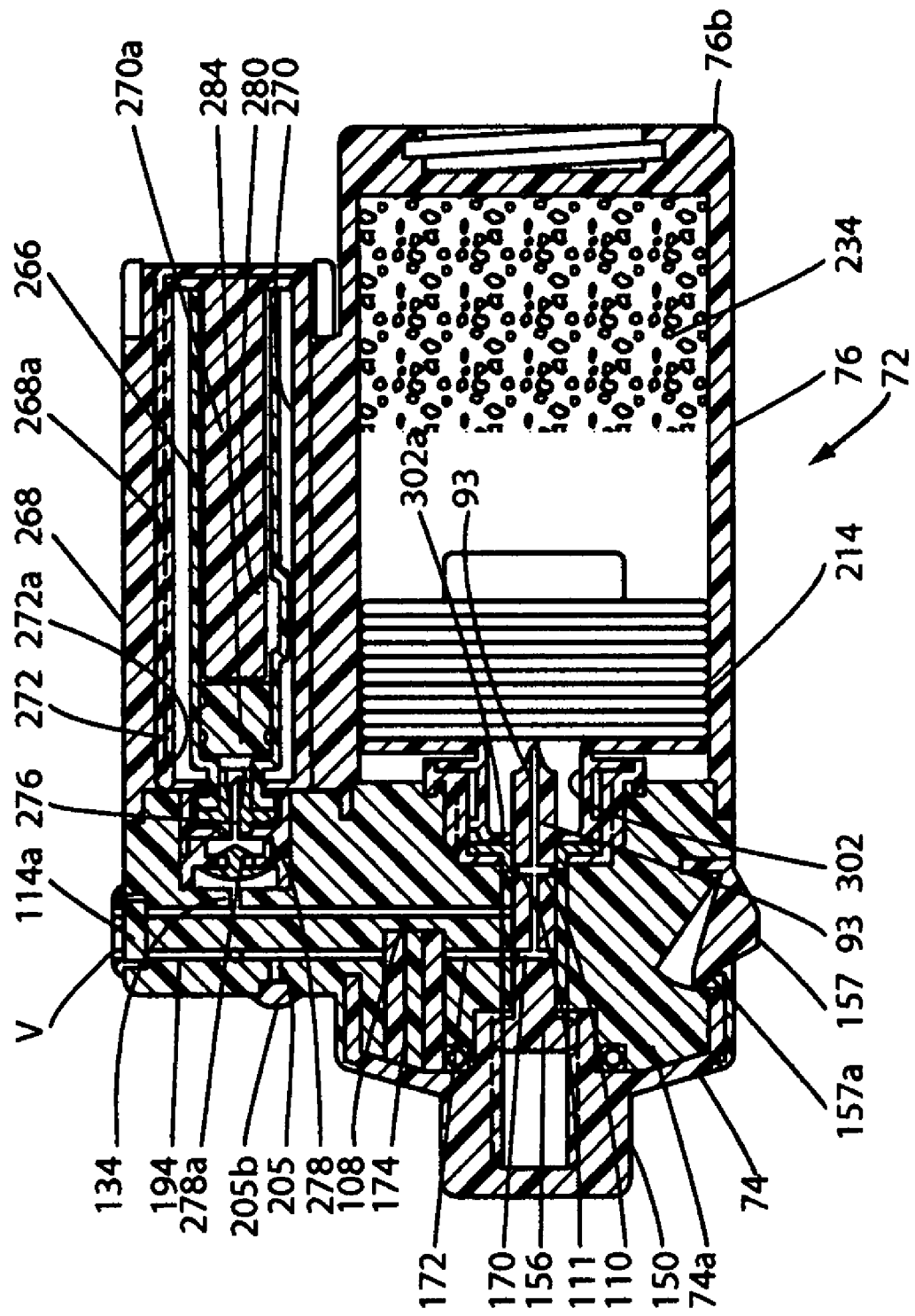
FIG. 50 is a cross-sectional view similar to FIG. 48 illustrating the appearance of the fluid reservoir of the fluid dispensing device in a collapsed configuration.
Figure 54:
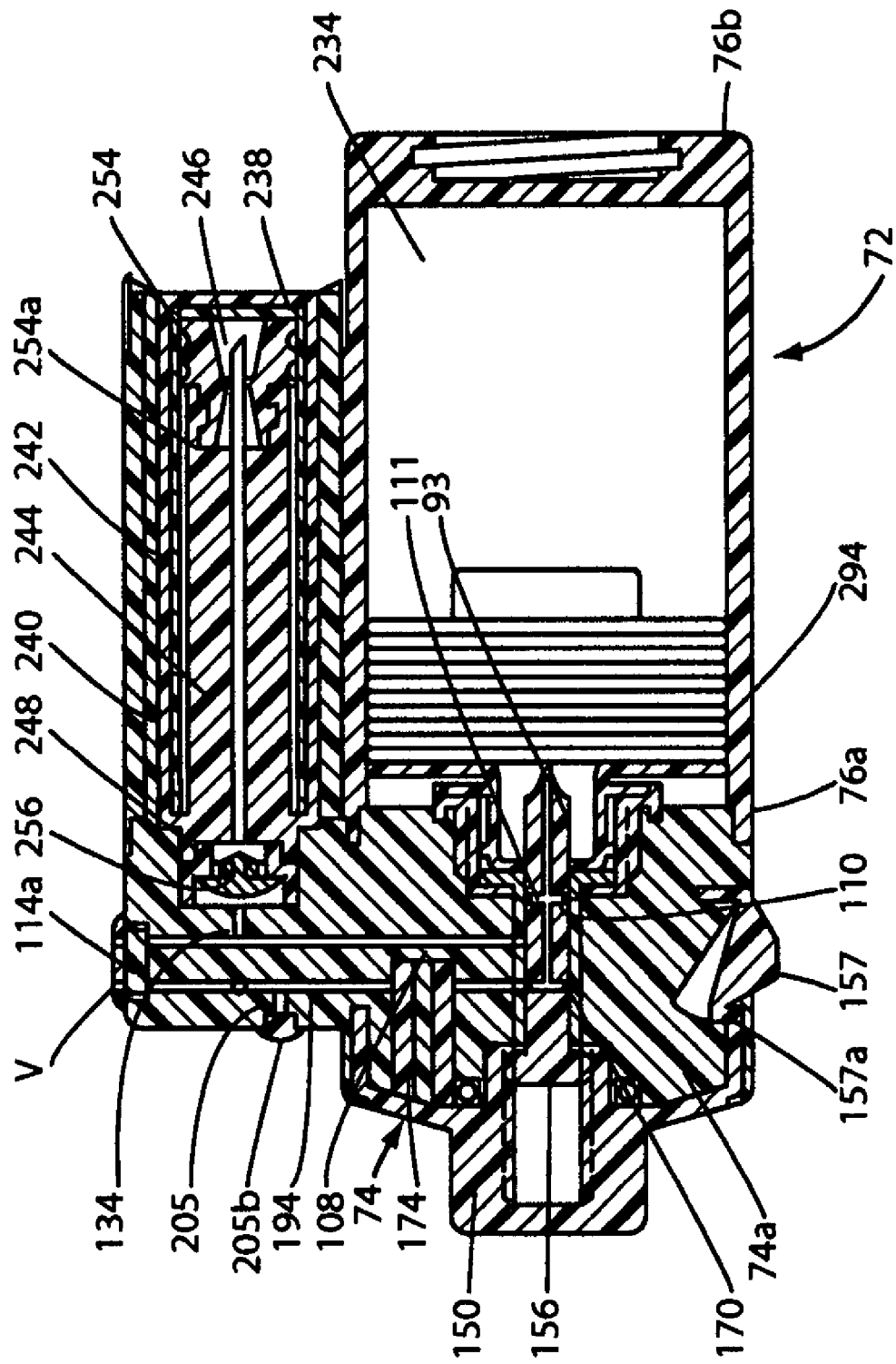
FIG. 54 is a cross-sectional view similar to FIG. 52 illustrating the appearance of the fluid reservoir of the fluid dispensing device in a collapsed configuration.

As in the earlier described embodiment, a pusher member 270 is telescopically receivable into housing chamber 268a and a vial 272 telescopically receives the previously mentioned cartridge-vial 266 (see also FIG. 50). Disposed within vial chamber 272a is a support 274, which carries a longitudinally extending, hollow needle 276 having a flow passageway that communicates with a check valve housing 278 formed proximate one end of the vial.

With the cartridge-vial 266 positioned within chamber 272a, a continuous pushing movement of the pusher member 270 into housing chamber 268a will cause pusher 270a of the pusher member 270 to move the elastomeric plunger 284 inwardly of the fluid chamber 280 in a direction toward the second, or closed end 266b of the vial. As the plunger is moved inwardly of the fluid chamber 280, the fluid "F" contained within the fluid chamber will be expelled therefrom into the hollow needle 276. As before, the fluid will then flow past conventional elastomeric umbrella-type check valve 278a, which is mounted within check valve housing 278 of the vial. Next, the fluid will flow into stub passageway 134 and thence into passageway 108.

Following filling of the reservoir in the manner previously described, the operating means is used to control the fluid flow from the collapsible reservoir toward the rate control means and then onward toward the administration set. More particularly, following the piercing of closure wall 302a and pierceable membrane 304 by the penetrating member 93, the compressible, expandable sponge 234 will move from its compressed position shown in FIG. 48 to its expanded position shown in FIG. 50 and in so doing will controllably collapse the container 300. As the container collapses, the medicinal fluid contained within the container will be controllably expelled therefrom.

To further control the flow of medicinal fluid from reservoir 295 toward the administration set 162 of the invention and then on to the patient, flow rate control means are provided. These important flow rate control means, which comprise a part of the operating means, are identical to those previously described in connection with the embodiment of FIGS. 28 through 38 and will not here be further discussed.

From the flow rate control means of the flow control means, the fluid will flow into elongated passageway 194 formed in body 74a of control portion 74 and from there will flow onward to the administration set 162 and then to the patient. As before, by varying the geometry, including the length, depth and width of the flow control channel 180c of the flow rate control means, the rate of fluid flow to the patient can be readily varied.

Referring to FIGS. 51 through 54, yet another form of the dispensing device of the present invention for dispensing medicaments to a patient is there shown and generally designated by the numeral 312. This alternate form of dispensing device is similar in many respects to that shown in FIGS. 47 through 50 and like numerals are used in FIGS. 51 through 54 to identify like components. The major differences between this latest embodiment of the invention and that shown in FIGS. 47 through 50 resides in the differently configured adding means for adding medicaments to the fluid contained within the fluid. More particularly, rather than being a cartridge-type fill-vial, the fill-vial of the adding means of this latest form of the invention comprises a shell-vial of the type described in connection with the embodiment of the invention shown in FIGS. 39 through 42.

Referring particularly to FIG. 52, the medicament containing fill-vial, or shell-vial 242 includes a body portion 242a, having a fluid chamber 250 for containing the injectable fluid medicament "F". Chamber 250 is provided with a first open end 250a and second closed end 250b. First open end 250a is sealably closed by closure means here provided in the form of an externally threaded elastomeric plunger 254, which is telescopically movable within the vial from a first location, where the plunger is disposed proximate first open end 250a to a second, device-fill location where the plunger is disposed proximate second closed end 250b.

In carrying out the reservoir-fill, or medicament adding step, vial 242 is first inserted into chamber 240a of the vial 240, which is identical in construction to the vial shown in FIGS. 49 and 41, and the threaded end 254a of plunger 254 is threadably interconnected with threaded end 244a of support 244. (see FIGS. 52 and 53) As the components are thusly interconnected, the sharp end of the elongated needle 246 will pierce the central wall 254b of the elastomeric plunger. In the manner previously described, a continuous pushing movement of the vial 242 into chamber 240a by means of the pusher member 238 will cause the support 244 to move the elastomeric plunger inwardly of the vial chamber in a direction toward the second, or closed end 250b of the vial chamber. As the plunger is moved inwardly of the vial, the fluid "F" contained within the vial chamber will be expelled therefrom into the hollow elongated needle 246. As best seen in FIG. 53, the fluid will then flow past conventional elastomeric umbrella-type check valve 256, which is mounted within check valve housing 248 of the vial. Next, the fluid will flow into stub passageway 134 and thence into passageway 108. Umbrella-type check valve 256 functions in a conventional manner to control fluid flow from the elongated hollow needle 246 toward fluid passageway 108. From passageway 108, the fluid will flow into inlet passageway 111 and then into reservoir 295 of the container 294, which is identical in construction to the container of FIG. 48.

Following the filling and medicament adding step in the manner previously described, the operating means is used to control the fluid flow from the collapsible reservoir 295 toward the rate control means and then onward toward the administration set.

To further control the flow of medicinal fluid from reservoir 295 toward the administration set 162 of the invention and then on to the patient, flow rate control means are provided. These important flow rate control means, which comprise a part of the operating means, are identical to those previously described in connection with the embodiment of FIGS. 28 through 38 and will not here be further discussed.

From the flow rate control means of the flow control means, the fluid will flow into elongated passageway 194 formed in body 74a of control portion 74 and from there will flow onward to the administration set 162 and then to the patient.

Figure 57:
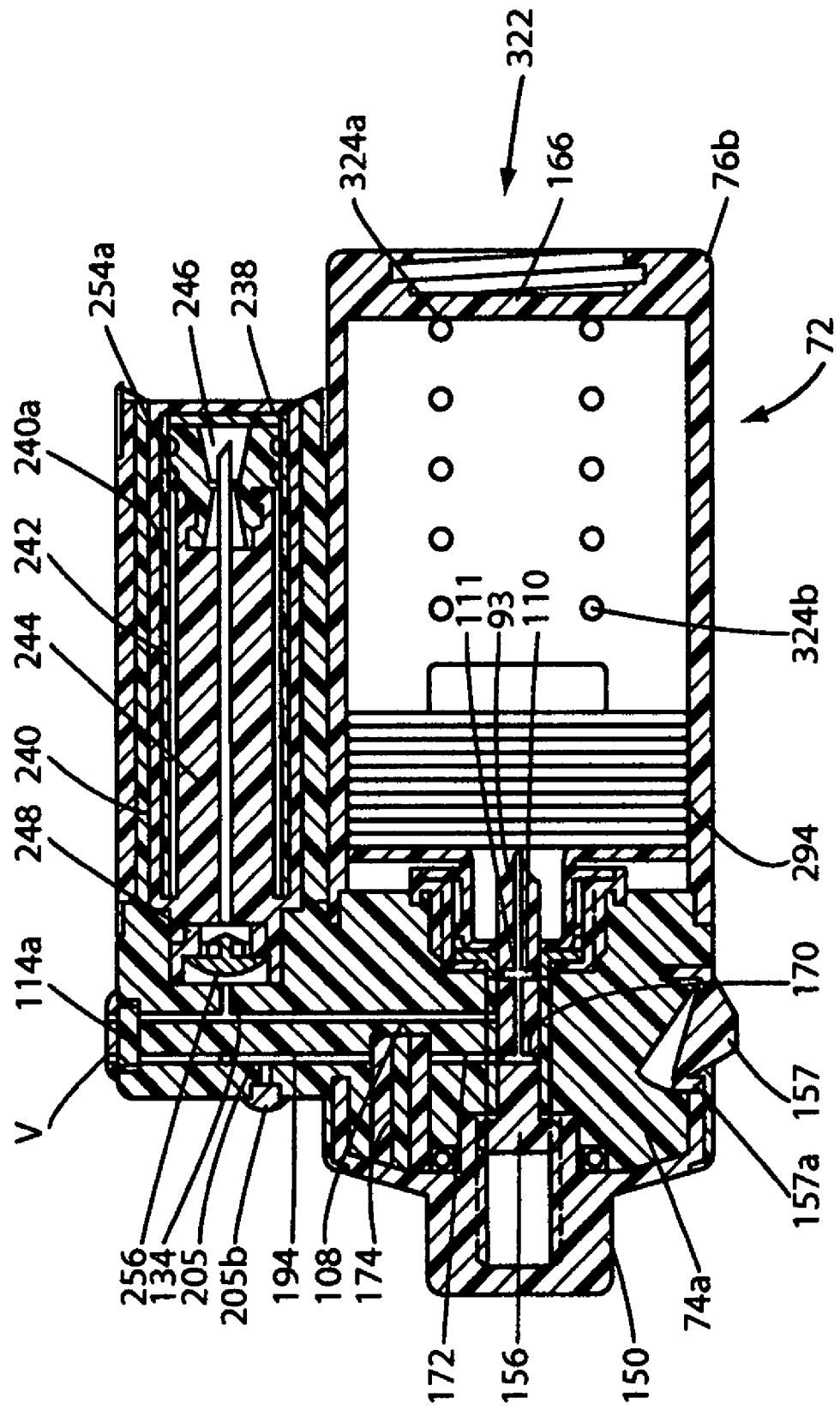
FIG. 57 is a cross-sectional view similar to FIG. 56 but showing the device following delivery of the fluid from the fluid reservoir.

Referring to FIGS. 55 through 57, still another form of the dispensing device of the present invention for dispensing medicaments to a patient is there shown and generally designated by the numeral 322. This alternate form of dispensing device is similar in many respects to that shown in FIGS. 51 through 55 and like numerals are used in FIGS. 55 through 57 to identify like components. The major differences between this latest embodiment of the invention and that shown in FIGS. 47 through 50 resides in the totally differently configured stored energy means of the invention. As illustrated in FIG. 56, the housing 72, the collapsible container 294 and the adding means for adding medicaments to the fluid contained within the fluid reservoir are substantially identical in construction and operation to those previously described. However, the stored energy means, rather than being in the nature of a compressible sponge, comprises a coil spring 324 that is carried within housing 72 and acts directly on the collapsible container 294 to expel the fluid therefrom. As illustrated in FIGS. 56 and 57, one end 324a of the coil spring 324 is disposed in engagement with the threaded base portion 76b of reservoir housing 76 and the other end 324b thereof is disposed in direct engagement with the bottom portion of the collapsible container 294.

Following the reservoir-fill step in the manner previously described, the operating means is used to control the fluid flow from the collapsible reservoir 295 toward the rate control means and then onward toward the administration set. More particularly, after the reservoir-filling step has been completed the fluid contained within the fluid reservoir can be dispensed to the patient by pivoting the indexing button 157 inwardly to move the locking tab 157a out of engagement with the notch within which it resides. This done, the control knob can be further rotated to the "DISP." position thereby causing the needle housing 156 to controllably move to the fluid delivery position shown in FIG. 57. In this position fluid passageway 170 aligns with dispensing passageway 172 formed in control body portion 74a so that fluid can flow from reservoir 295 toward the administration set 162 due to the urging of spring 324.

As the accordion-like side wall of the container collapses due to the urging of the coiled spring, the medicinal fluid contained within the container will be controllably expelled therefrom and will flow toward the fluid passageway of penetrating member 93. From the fluid passageway of penetrating member 93, fluid will flow into a stub passageway 170 formed in needle housing 156. As illustrated in FIG. 57, stub passageway 170 is now aligned with a passageway 172 which forms the inlet to the fluid rate control means of the invention.

From the flow rate control means of the flow control means, the fluid will flow into elongated passageway 194 formed in body 74a of control portion 74 and from there will flow onward to the administration set 162 and then to the patient. As before, by varying the geometry, including the length of the flow control channel 180c of the flow rate control means, the rate of fluid flow to the patient can be readily varied.

Figure 60:
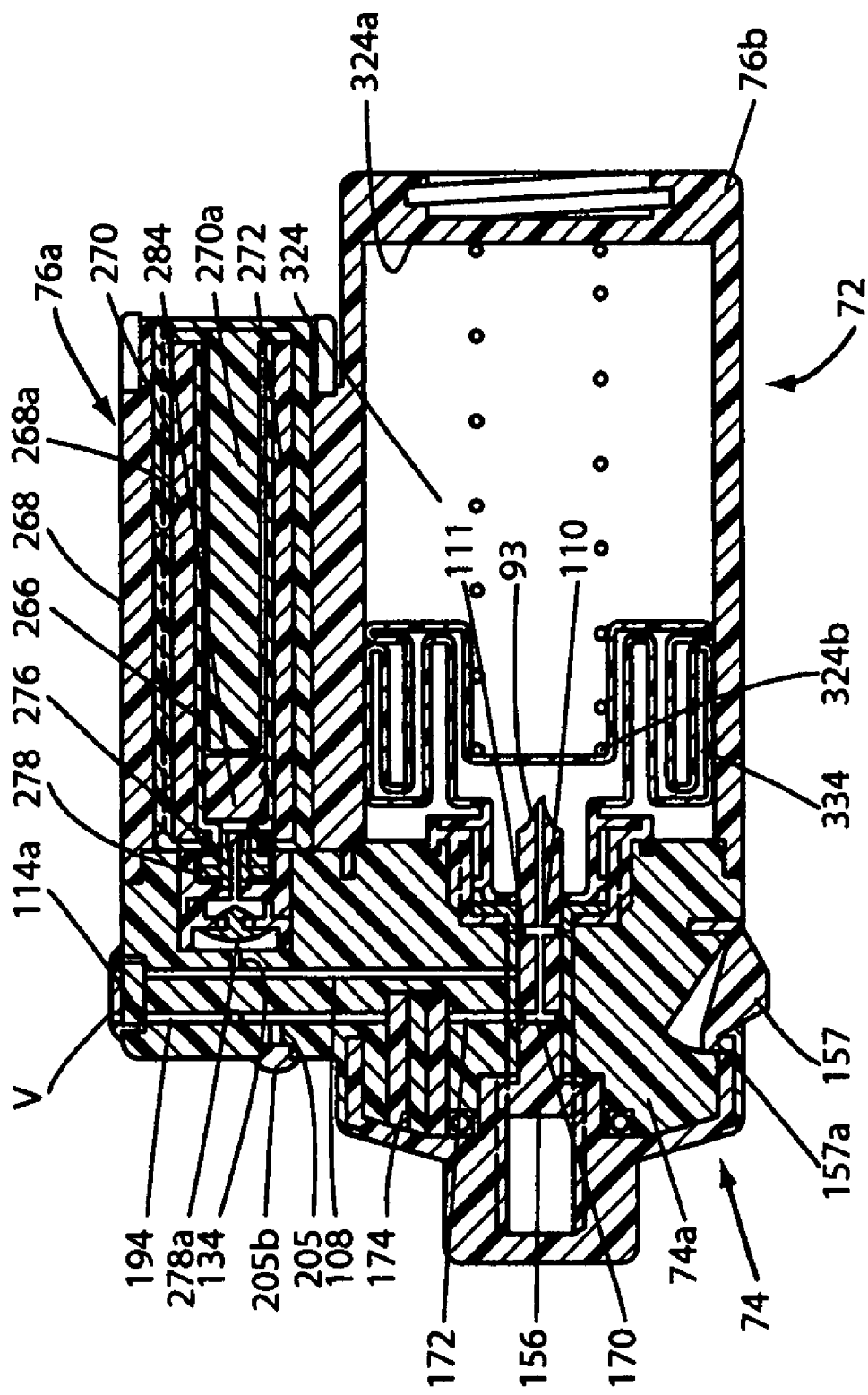
FIG. 60 is a cross-sectional view, similar to FIG. 59, illustrating the appearance of the fluid reservoir of the fluid dispensing device in a collapsed configuration.

Referring to FIGS. 58 through 60, yet another form of the dispensing device of the present invention for dispensing medicaments to a patient is there shown and generally designated by the numeral 332. This alternate form of dispensing device is similar in many respects to that shown in FIGS. 55 through 57 and like numerals are used in FIGS. 58 through 60 to identify like components. The major differences between this latest embodiment of the invention and that shown in FIGS. 47 through 50 resides in the totally differently configured semi-rigid collapsible container 334 and the differently configured adding means.

As shown in FIGS. 59 and 60, container 334, rather than being in the nature of the collapsible container having a bellows-like sidewall, comprises a collapsible, bottle-like container of the character illustrated in FIG. 59. More particularly, container 334 has a collapsible side wall 334a that is movable from the expanded, starting configuration shown in FIG. 59 to the collapsed configuration shown in FIG. 60. As before, collapsible container 334 defines a fluid reservoir 337. As before, device of the invention comprises a housing 72, that is substantially identical to that shown in FIG. 1 and includes a control portion 74 and a reservoir housing 76 having a generally cylindrically shaped wall portion 76a and a base portion 76b.

The adding means, of this latest form of the invention, which is carried by portion 76a of housing 72, rather than being in the nature of a shell-vial, here comprises a generally conventional cartridge-vial 266, which is identical in construction and operation to that of the embodiment of FIG. 45.

As illustrated in FIG. 59, the control portion 74 of housing 72 includes a housing 268 having a chamber 268a. A pusher member 270 is telescopically receivable over an elongated vial 272, which is also disposed within chamber 268a. Telescopically receivable within chamber 272a of a vial 272 is the cartridge-vial 266. Disposed within vial chamber 272a is a support 274, which carries a longitudinally extending, hollow needle 276 having a flow passageway that communicates with a check valve housing 278 formed proximate one end of the vial.

The stored energy means of this latest form of the invention is substantially identical in construction and operation to that of the embodiment of FIGS. 56 and 57 and comprises a coil spring 324 that is carried within housing 72. Spring 324 acts directly on the collapsible container 334 to expel the fluid therefrom. As illustrated in FIGS. 59 and 60, one end 324a of the coil spring 324 is disposed in engagement with the threaded base portion 76b of reservoir housing 76 and the other end 324b thereof is disposed in direct engagement with the bottom portion of the collapsible container 334.

Following the reservoir-fill and medicament adding step in the manner previously described, the operating means is used to control the fluid flow from the collapsible reservoir 337 toward the rate control means and then onward toward the administration set. More particularly, after the reservoir-filling step has been completed the fluid contained within the fluid reservoir can be dispensed to the patient by pivoting the indexing button 157 inwardly to move the locking tab 157a out of engagement with the notch within which it resides. This done, the control knob can be further rotated to the "DISP." position thereby causing the needle housing 156 to controllably move to the fluid delivery position. In this position fluid passageway 170 aligns with dispensing passageway 172 formed in control body portion 74a so that fluid can flow from reservoir 337 toward the administration set 162 due to the urging of spring 324.

As the container collapses due to the urging of the coiled spring, the medicinal fluid contained within the container will be controllably expelled therefrom and will flow toward the fluid passageway of penetrating member 93. From the fluid passageway of penetrating member 93, fluid will flow into a stub passageway 170 formed in needle housing 156. As illustrated in FIG. 60, stub passageway 170 is now aligned with a passageway 172 which forms the inlet to the fluid rate control means of the invention.

From the flow rate control means of the flow control means, the fluid will flow into elongated passageway 194 formed in body 74a of control portion 74 and from there will flow onward to the administration set 162 and then to the patient. As before, by varying the geometry, including the length, width and depth of the flow control channel 180c of the flow rate control means, the rate of fluid flow to the patient can be readily varied.

Referring to FIGS. 61 through 66, still another form of the dispensing device of the present invention for dispensing medicaments to a patient is there shown and generally designated by the numeral 342. This alternate form of dispensing device is similar in many respects to that shown in FIGS. 58 through 60 and like numerals are used in FIGS. 61 through 66 to identify like components. The major differences between this latest embodiment of the invention and that shown in FIGS. 58 through 60 resides in the totally differently configured stored energy means of the invention. As best seen in FIGS. 64 through 66, the collapsible container 334 and the reservoir adding means for adding medicaments to the fluid contained within the reservoir of the filled container and the operating means are substantially identical in construction and operation to those previously described. However, the stored energy means, rather than being in the nature of a coil spring, here comprises a plurality of cooperating, circumferentially spaced, constant force negator springs 344 that are carried within the control portion of the outer housing.

Constant force springs 344, which are a special variety of extension spring, are readily commercially available from several sources including Barnes Group Inc. of Bristol, Conn., Stock Drive Products/Sterling Instrument of Hyde Park, N.Y. and Walker Corporation of Ontario, Canada. These novel springs are basically high stress, long deflection devices that offer great advantages when used in applications where very low or zero gradient is desired, where space is a factor and where very high reliability is required. Constant force springs, such as springs 344, provide markedly superior constant force loading when compared to conventional helical extension or like springs. Springs 344, after being expanded, tend to uniformly retract and in so doing exert a constant force on a carriage assembly 346 that is mounted within housing 350. Following release of carriage 346 of the carriage assembly, in a manner presently to be described, the carriage will urge the semi-rigid collapsible container 334 to move from the expanded configuration shown in FIG. 65 to the collapsed position shown in FIG. 66. As the container 334 collapses the fluid contained within the fluid reservoir 337 will be caused to flow outwardly through an inlet formed in penetrating member 93 and toward the flow rate control means of the invention at a substantially constant rate.

Figure 61:
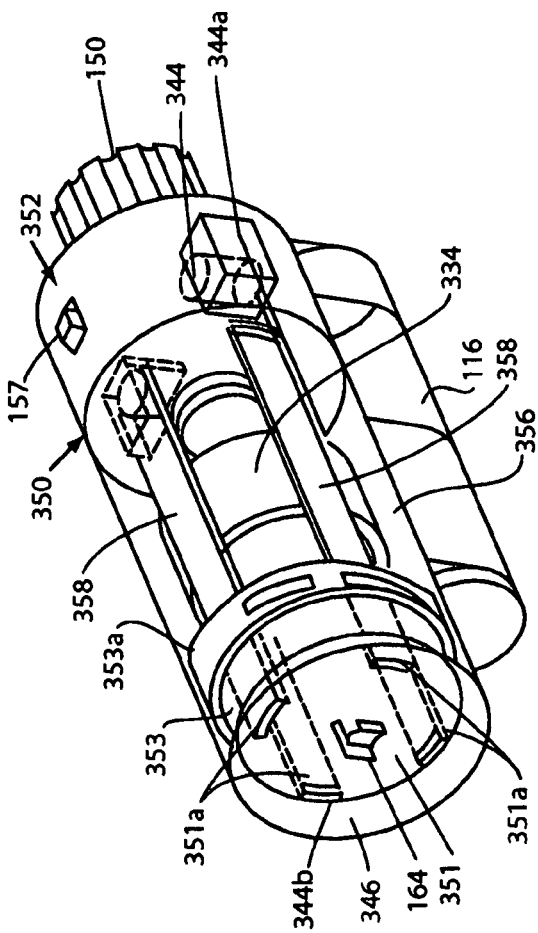
FIG. 61 is a generally perspective view, partly broken away to show internal construction, of yet another alternate form of the fluid dispensing device of the present invention for dispensing medicaments to a patient.
Figure 62:
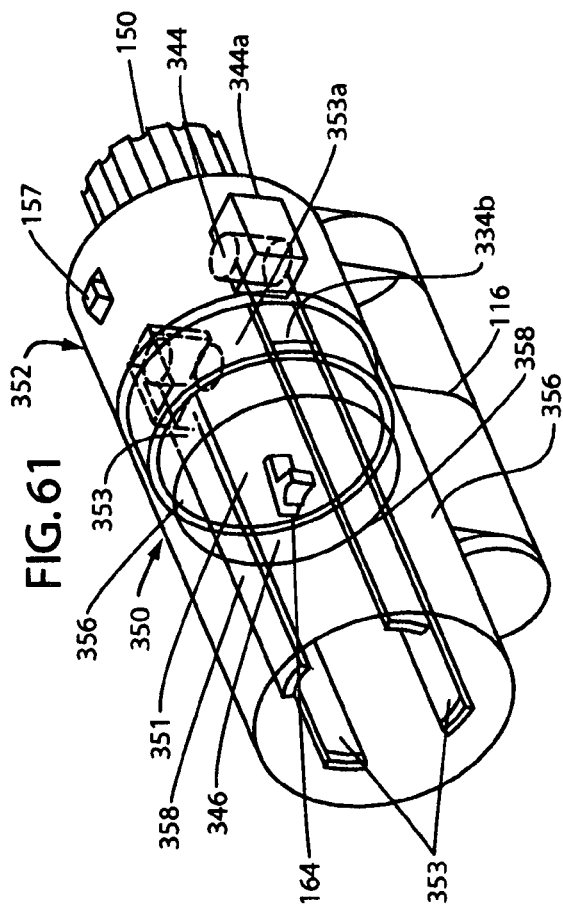
FIG. 62 is a generally perspective view, similar to FIG. 61, illustrating the appearance of the fluid dispensing device following the fluid delivery step.

In this latest form of the invention, the dispensing device housing 350 is similar in many respects to the earlier described housing 72, but is slightly differently configured so as to support the spool housings 344*a* of the circumferentially spaced constant force springs 344. As illustrated in FIGS. 61, 62 and 65, housing 350 includes a control portion 352 and a generally cylindrically shaped reservoir housing 356 that is interconnected with the control portion 352 in the manner best seen in FIG. 65 of the drawings. As before, housing 350 can be constructed from metal, plastic or any suitable material. Reservoir housing 356 includes a generally cylindrically shaped wall portion 356*a* and a base portion 356*b*. As illustrated in FIGS. 61, 62 and 65, the spool portions 361 about which the constant force springs 344 are coiled, are housed within control portion 352 of the housing and are constructed and arranged so that springs 344 can extend downwardly within housing portion 356*a* so that the free ends 344*b* thereof can be interconnected with the carriage 346.

Disposed within wall portion 356*a* is the previously identified carriage assembly 346, which carries container 334 and is movable between a first position shown in FIGS. 61 and 64 and a second position shown in FIGS. 62 and 66. As best seen by referring to FIGS. 61 and 64, carriage 346 has a carriage base 351 that is each provided with a plurality of circumferentially spaced openings 351*a* and a generally cylindrically shaped sidewall 353 which terminates in a radially outwardly extending flange 353*a*. As indicated in the drawings, the free ends 344*b* of the constant force springs are interconnected with flange 353*a*. Carriage assembly 346 is releasably locked in its first position by a novel locking means of similar nature to that previously described.

An important feature of this latest form of the invention resides in the provision of novel guide means for guiding travel of carriage assembly 346 between its first and second positions. The guide means here comprises a plurality of circumferentially spaced guide members 358, which are connected to and extend outwardly from body 352*a* of control portion 352 (FIGS. 61 and 65). As indicated in the drawings, guide members 358 are slidably received within openings 351*a* provided in carriage base 351 (FIGS. 64 and 65) so that as the carriage assembly travels from its first position toward its second position, guide members 358 precisely guide its travel. Also forming a part of the guide means of the apparatus of the present invention are a plurality of circumferentially spaced guide grooves 359 that are formed on the inner wall of outer housing 356 (FIGS. 64 and 65).

Following the accomplishment of the medicament adding step in the manner previously described, the operating means of the invention is used to control the fluid flow from the collapsible reservoir 337 toward the rate control means and then onward toward the administration set. In this latest form of the invention, the operating means, as well as the rate control means and the administration set, are identical to those previously described. More particularly, after the medicament adding step has been completed, the fluid contained within the field reservoir can be dispensed to the patient by once again pivoting the indexing button 157 inwardly to move the locking tab 157*a* out of engagement with the notch within which it resides. This done, the control knob 150 can be further rotated to the "DISP." position thereby causing the penetrating member 93 to controllably move to the fluid delivery position. In this position fluid passageway 170 aligns with dispensing passageway 172 formed in control body portion 352*a* so that fluid can flow from reservoir 337 toward the administration set 162 via the flow rate control means of the invention.

To cause the fluid to flow from reservoir 337 toward the flow rate control means, the locking means of the invention must be manipulated in the manner previously described to release the carriage assembly from base wall 356*b* of reservoir housing 356. Release of the carriage will permit the stored energy means, or constant force springs 344, to move the carriage from a position shown in FIG. 64 into the position shown in FIG. 66. As the collapsible sidewall of the container 334 collapses due to the urging force of the springs, the medicinal fluid contained within the container will be controllably expelled therefrom and will flow toward the fluid passageway of penetrating member 93 which has now moved into the position shown in FIG. 66 of the drawings. From the fluid passageway of penetrating member 93 fluid will flow into a stub passageway 170 formed in needle housing 156. As illustrated in FIG. 64, stub passageway 170 is now aligned with a passageway 172 which forms the inlet to the fluid rate control means of the invention.

From the flow rate control means of the flow control means the fluid will flow into elongated passageway 194 formed in body 352*a* of control portion 352 and from there will flow onward to the administration set 162 and then to the patient. As before, by varying the geometry, including the length, width and depth of the flow rate control channel of the flow rate control means, the rate of fluid flow to the patient can be readily varied.

Referring to FIGS. 67 through 72, still another form of the dispensing device of the present invention for dispensing medicaments to a patient is there shown and generally designated by the numeral 362. This alternate form of dispensing device is similar in many respects to that shown in FIGS. 61 through 66 and like numerals are used in FIGS. 67 through 72 to identify like components. The major differences between this latest embodiment of the invention and that shown in FIGS. 58 through 60 resides in the differently configured collapsible container 294 which is substantially identical to the container shown in FIG. 52 of the drawings.

As shown in FIGS. 71 and 72, container 294, rather than being in the nature of a collapsible, bottle-like container here comprises a collapsible container having a bellows-like sidewall. More particularly, container 294 has a collapsible sidewall that is movable from the expanded, starting configuration shown in FIG. 71 to the collapsed configuration shown in FIG. 72. As before, collapsible container 294 defines a fluid reservoir 295 that is accessible in the manner previously described.

As in the last described embodiment of the invention, the device here comprises a housing 350 that includes a control portion 352 and a generally cylindrically shaped reservoir housing 356 that is interconnected with the control portion 352 in the manner best seen in FIG. 70.

As best seen in FIGS. 70 through 72, the stored energy means, the reservoir adding means for adding medicaments to the fluid contained within the reservoir of the filling the container and the operating means are substantially identical in construction and operation to those previously described. However, the stored energy means, rather than being in the nature of a coil spring, here comprises a plurality of cooperating, circumferentially spaced, constant force springs 344 that are carried within the control portion of the outer housing shown in FIGS. 70 and 72 of the drawings.

Disposed within wall portion 356a is a carriage assembly 346, which is identical in construction and operation to that previously described, here carries container 294. Also identical in construction and operation to the previously described embodiment of the invention are the guide means which function to guide the travel of carriage assembly 346 between its first and second positions.

Following the accomplishment of the medicament adding step in the manner previously described, the operating means of the invention is used to control the fluid flow from the collapsible reservoir 295 toward the rate control means and then onward toward the administration set. In this latest form of the invention the rate control means and the administration set are identical to those previously described. More particularly, after the medicament adding step has been completed, the fluid contained within the field reservoir can be dispensed to the patient by once again pivoting the indexing button 157 inwardly to move the locking tab 157a out of engagement with the notch within which it resides. This done, the control knob 150 can be further rotated to the "DISP." position thereby causing the penetrating member 93 to controllably move to the fluid delivery position. In this position fluid passageway 170 aligns with dispensing passageway 172 formed in control body portion 352a so that fluid can flow from reservoir 295 toward the administration set 162 via the flow rate control means of the invention.

To cause the fluid to flow from reservoir 295 toward the flow rate control means, the locking means of the invention must be manipulated in the manner previously described to release the carriage assembly from base wall 356b of reservoir housing 356. Release of the carriage will permit the stored energy means, or constant force springs 344, to move the carriage from a position shown in FIG. 71 into the position shown in FIG. 72. As the bellows-like, collapsible sidewall of the container 294 collapses in a uniformly controlled manner due to the urging of the constant force springs, the medicinal fluid contained within the container will be controllably expelled therefrom and will flow toward the fluid passageway of penetrating member 93. From the fluid passageway of penetrating member 93, fluid will flow into stub passageway 170 formed in penetrating member 93 and then into passageway 172 which forms the inlet to the fluid rate control means of the invention.

Figure 75:
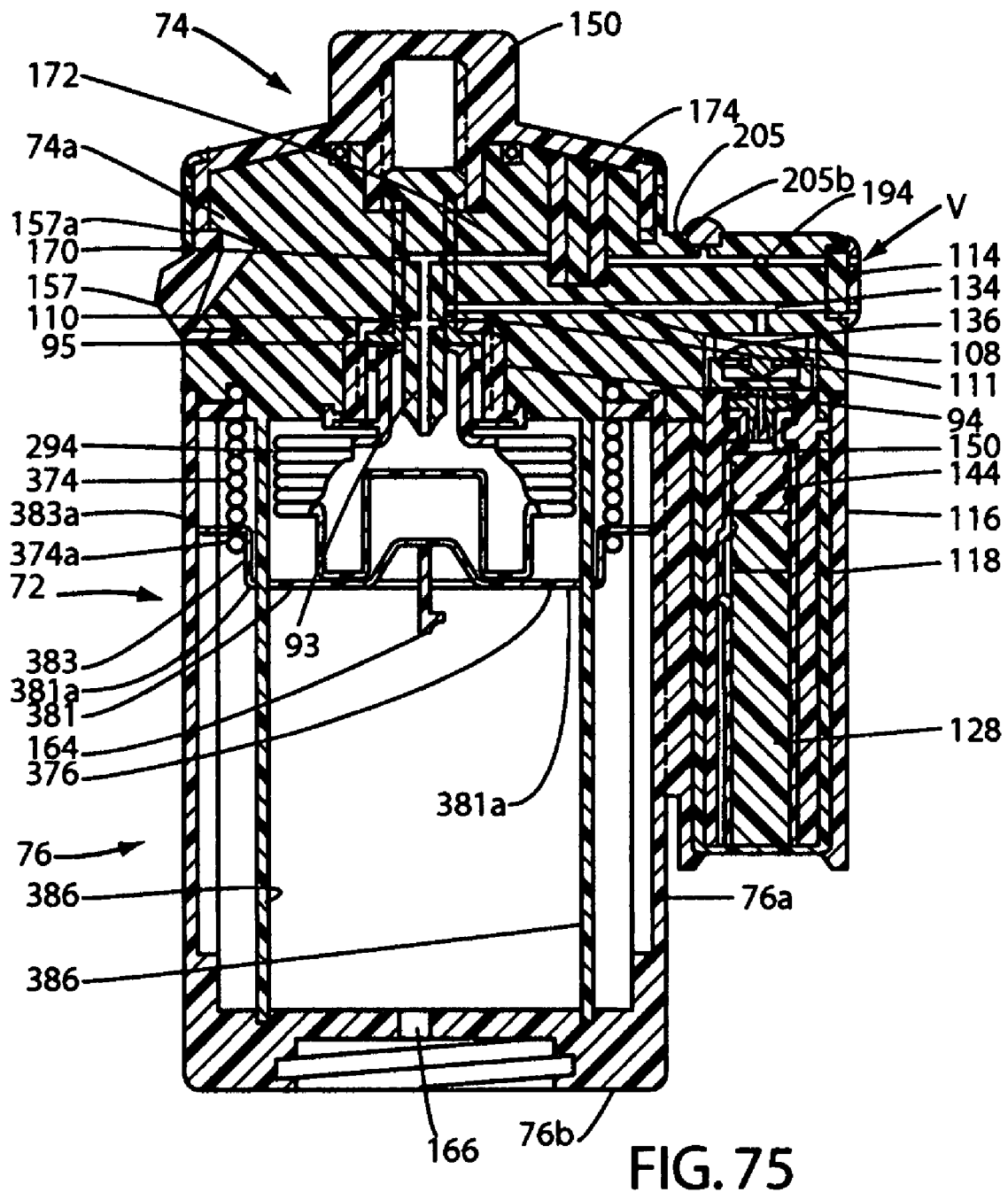
FIG. 75 is a cross-sectional view similar to FIG. 74 illustrating the appearance of the fluid dispensing device following the fluid delivery step.

Referring to FIGS. 73 through 75, still another form of the dispensing device of the present invention for dispensing medicaments to a patient is there shown and generally designated by the numeral 372. This alternate form of dispensing device is similar in many respects to that shown in FIGS. 70 through 72 and like numerals are used in FIGS. 73 through 75 to identify like components. The major differences between this latest embodiment of the invention and that shown in FIGS. 70 through 72 resides in still another type of stored energy means. As best seen in FIGS. 74 and 75, the collapsible container 294, the reservoir adding means and the operating means are substantially identical in construction and operation to those previously described. However, the stored energy means, rather than being in the nature of a coil spring in compression when the reservoir is in any filled condition, here uniquely comprises a coil spring 374 that is in tension when the reservoir is in a filled configuration (FIG. 74). With this construction, upon release of the carriage assembly 376 in the manner previously described, the coil spring 374 will retract and in the manner shown in FIG. 75 will urge the carriage to move into the fluid delivery position shown in FIG. 75. This movement of the carriage will cause the semi-rigid collapsible container 294 to move from the expanded configuration shown in FIG. 74 to the collapsed position shown in FIG. 75. As the container 294 collapses, the fluid contained within the fluid reservoir 295 will flow outwardly through an inlet formed in penetrating member 93 and then onward toward the flow rate control means of the invention at a substantially constant rate.

In this latest form of the invention, the dispensing device housing 72 is similar in most respects to the earlier described housing 72 and includes a control portion 74 and a generally cylindrically shaped reservoir housing 76 that is interconnected with the control portion 74 in the manner best seen in FIG. 74 of the drawings. As before, reservoir housing 76 includes a generally cylindrically shaped wall portion 76a and a base portion 76b.

Disposed within wall portion 76a is the previously identified carriage assembly 376, which carries container 294 and is movable between a first position shown in FIG. 74 and a second position shown in FIG. 75. As best seen by referring to FIGS. 74 and 75, carriage assembly 376 has a carriage base 381 that is provided with a plurality of circumferentially spaced openings 381a and a generally cylindrically shaped sidewall 383 which terminates in a radially outwardly extending flange 383a. As indicated in the drawings, end 374a of spring 374 is interconnected with flange 383a. Carriage assembly 376 is releasably locked in its first position by a novel locking means of similar nature to that previously described.

As in the earlier described embodiments of the invention guide means are provided for guiding travel of carriage assembly between its first and second positions. The guide means here comprises a plurality of circumferentially spaced guide members 386, which are connected to and extend outwardly from body 74a of control portion 74 (FIGS. 74 and 75). As indicated in the drawings, guide members 386 are slidably received within openings 381a provided in carriage base 381 so that, as the carriage assembly travels from its first position toward its second position, the guide members precisely guide its travel.

Following the accomplishment of the medicament adding step in the manner previously described, the operating means of the invention is used to control the fluid flow from the collapsible reservoir 295 toward the rate control means and then onward toward the administration set. In this latest form of the invention, the operating means, as well as the rate control means and the administration set, are identical to those previously described. More particularly, after the medicament adding step has been completed, the fluid contained within the field reservoir can be dispensed to the patient by once again pivoting the indexing button 157 inwardly to move the locking tab 157*a* out of engagement with the notch within which it resides. This done, the control knob 150 can be further rotated to the "DISP." position thereby causing the penetrating member 93 to controllably move to the fluid delivery position. In this position fluid passageway 170 aligns with dispensing passageway 172 formed in control body portion 74*a* so that fluid can flow from reservoir 295 toward the administration set 162 via the flow rate control means of the invention.

To cause the fluid to flow from reservoir 295 toward the flow rate control means, the locking means of the invention must be manipulated in the manner previously described to release the carriage assembly from base wall 76*b* of reservoir housing 76. Release of the carriage will permit the stored energy means, or spring 374, to retract in a manner to move the carriage from a position shown in FIG. 74 into the position shown in FIG. 75. As the collapsible sidewall of the container 294 collapses due to the urging of the spring, the medicinal fluid contained within the container will be controllably expelled therefrom and will flow toward the fluid passageway of penetrating member 93, which has now moved into the position shown in FIG. 75 of the drawings. From the fluid passageway of penetrating member 93, fluid will flow into a stub passageway 170 formed in portion 156. As illustrated in FIG. 75, stub passageway 170 is now aligned with a passageway 172 which forms the inlet to the fluid rate control means of the invention.

From the flow rate control means of the flow control means, the fluid will flow into elongated passageway 194 formed in body 74*a* of control portion 74 and from there will flow onward to the administration set 162 and then to the patient. As before, by varying the geometry, including the length of the flow control channel of the flow rate control means, the rate of fluid flow to the patient can be readily varied.

Figure 76:
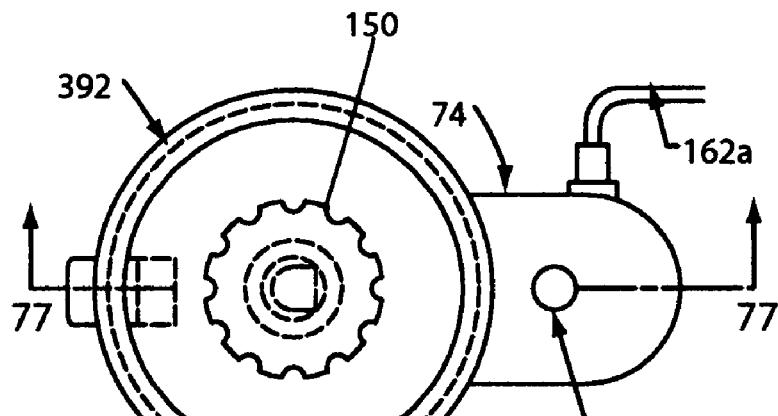
FIG. 76 is a front view of yet another form of the fluid dispensing device of the invention.
Figure 77:
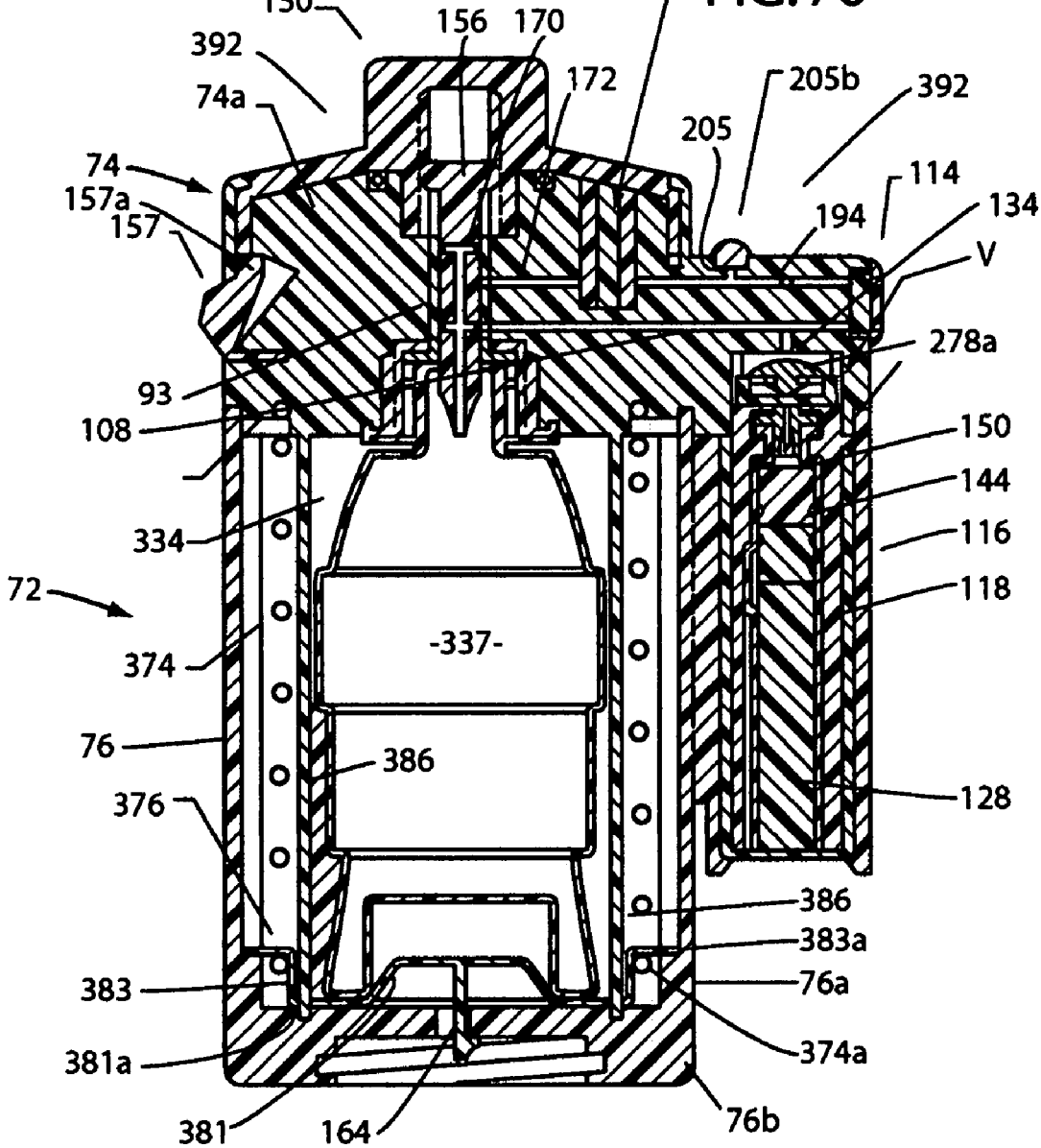
FIG. 77 is a cross-sectional view taken along lines 77-77 of FIG. 76.
Figure 78:
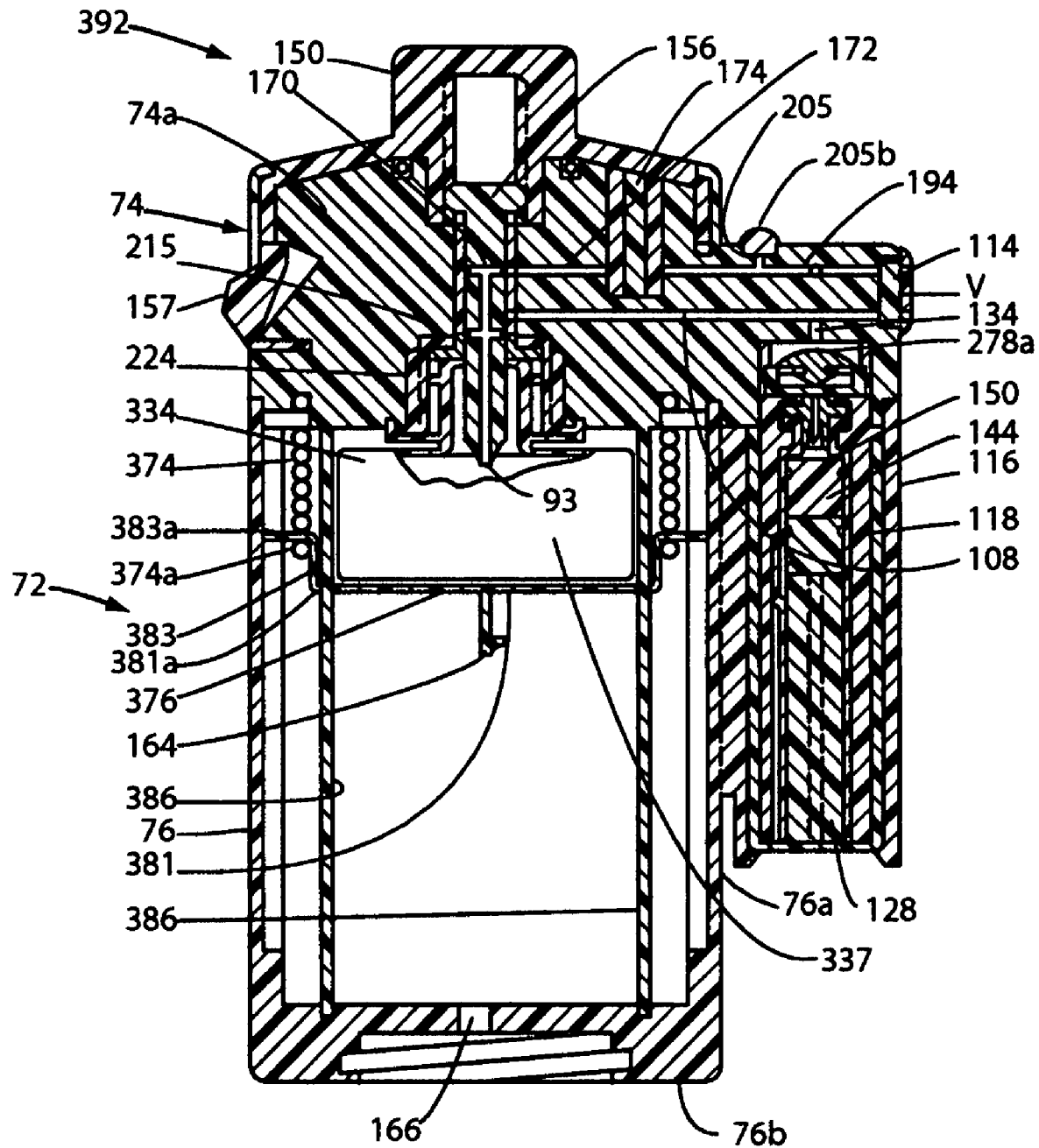
FIG. 78 is a cross-sectional view similar to FIG. 77 illustrating the appearance of the fluid dispensing device following the fluid delivery step.

Referring to FIGS. 76 through 78, yet another form of the dispensing device of the present invention for dispensing medicaments to a patient is there shown and generally designated by the numeral 392. This alternate form of dispensing device is similar in many respects to that shown in FIGS. 73 through 75 and like numerals are used in FIGS. 76 through 78 to identify like components. The major differences between this latest embodiment of the invention and that shown in FIGS. 73 through 75 resides in the differently configured collapsible container 334 which is substantially identical to the container shown in FIG. 59 of the drawings.

As shown in FIGS. 77 and 78, container 334, rather than being in the nature a collapsible container having a bellows-like sidewall, here comprises a semi-rigid collapsible, bottle-like container of the character shown in FIG. 59 of the drawings. More particularly, container 334 has a collapsible sidewall that is movable from the starting configuration shown in FIG. 77 to the collapsed configuration shown in FIG. 78. As indicated in FIG. 77, collapsible container 334 defines a fluid reservoir 337 that is accessible in the manner previously described.

As in the last described embodiment of the invention, the device here comprises a stored energy means, a carriage, a reservoir adding means and an operating means that are all substantially identical in construction and operation to those described in connection with the embodiment of FIGS. 73 through 75. More particularly, the stored energy means uniquely comprises a coil spring 374 that is in tension when the reservoir is in a filled configuration (FIG. 77). Upon release of carriage assembly 376, in the manner previously described, the coil spring 374 will retract and, in the manner shown in FIG. 78, will urge the carriage to move into the fluid delivery position shown in FIG. 78. This movement of the carriage will cause the collapsible container 334 to move from the expanded configuration shown in FIG. 77 to the collapsed position shown in FIG. 78. As the container 334 collapses, the fluid contained within the fluid reservoir 337 will flow outwardly through an outlet formed in penetrating member 93 and then onwardly toward the flow rate control means of the invention at a substantially constant rate.

In this latest form of the invention, the dispensing device housing 72 is also similar in most respects to the earlier described housing 72 and includes a control portion 74 and a generally cylindrically shaped reservoir housing 76 that is interconnected with the control portion 74 in the manner best seen in FIG. 77 of the drawings. As before, reservoir housing 76 includes a generally cylindrically shaped wall portion 76*a* and a base portion 76*b*.

Disposed within wall portion 76*a* is the previously identified carriage assembly 376 which carries container 334 and is movable between a first position shown in FIG. 77 and a second position shown in FIG. 78. As before, carriage assembly 376 has a carriage base 381 that is provided with a plurality of circumferentially spaced openings 381*a* and a generally cylindrically shaped sidewall 383 which terminates in a radially outwardly extending flange 383*a* to which end 374*a* of spring 374 is interconnected. Carriage assembly 376 is releasably locked in its first position by a novel locking means of similar nature to that previously described.

As in the earlier described embodiments of the invention guide means are provided for guiding travel of carriage assembly between its first and second positions. The guide means are identical in construction and operation to those previously described in connection with the embodiment of FIGS. 73 through 75.

Following the accomplishment of the medicament adding step in the manner previously described, the operating means of the invention is used to control the fluid flow from the collapsible reservoir 337 toward the rate control means and then onward toward the administration set. In this latest form of the invention, the operating means, as well as the rate control means and the administration set, are identical in construction and operation to those previously described.

To cause the fluid to flow from reservoir 337 toward the flow rate control means, the locking means of the invention must be manipulated in the manner previously described to release the carriage assembly from base wall 76*b* of reservoir housing 76. Release of the carriage will permit the stored energy means, or spring 374, to retract in a manner to move the carriage from a position shown in FIG. 77 into the position shown in FIG. 78. As the collapsible sidewall of the, container 334 collapses due to the urging of the spring, the medicinal fluid contained within the container will be controllably expelled therefrom and will flow toward the fluid passageway of penetrating member 93, which has now moved into the position shown in FIG. 78 of the drawings. From the fluid passageway of penetrating member 93, fluid will flow into a stub passageway 170 formed in body 74*a* of the control portion 74 with.

From the flow rate control means of the flow control means, the fluid will flow into elongated passageway 194 formed in body 74*a* of control portion 74 and from there will flow onward to the administration set 162 and then to the patient. As before, by varying the geometry, including the length, width and depth of the flow rate control micro-channel of the flow rate control means, the rate of fluid flow to the patient can be readily varied.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A dispensing device for dispensing medicaments to a patient comprising:
   (a) a supporting structure comprising a base assembly and an outer housing interconnected with said base assembly;
   (b) a carriage assembly interconnected with said supporting structure for movement between a first position and a second position, said carriage assembly comprising a carriage having a carriage base provided with a plurality of circumferentially spaced openings and a generally cylindrically shaped sidewall terminating in a radially outwardly extending flange;
   (c) locking means carried by said supporting structure for locking said carriage assembly in said first position;
   (d) a reservoir defining assembly formed in accordance with an aseptic blow-fill-seal manufacturing technique and including a pre-filled, collapsible reservoir carried by said carriage assembly, said collapsible reservoir containing medicaments to be dispensed to the patient and having an outlet port, said reservoir defining assembly comprising a collapsible container having an integrally formed top, bottom and collapsible side wall, said top wall having an integrally formed neck portion sealably closed by a closure wall;
   (e) guide means connected to said supporting structure for guiding travel of said carriage assembly between said first position and said second position, said guide means comprising a plurality of circumferentially spaced guide members connected to said base assembly and a guide rib connected to said housing of said supporting structure, said spaced-apart guide members being slidably received within said openings provided in said carriage base;
   (f) a stored energy means operably associated with said carriage assembly for moving said carriage assembly between said first and second positions, said stored energy means comprising a coil spring having a first end in engagement with said supporting structure and a second end in engagement with said radially outwardly extending flange of said carriage;
   (g) an administration set, including an administration line interconnected with said outlet port of said collapsible reservoir;
   (h) fluid flow control means carried by said base assembly of said supporting structure for controlling fluid flow from said collapsible reservoir toward said administration set, said flow control means comprising:
   (i) rate control means carried by said supporting structure for controlling the rate of fluid flow from said collapsible reservoir toward said administration set, said rate control means comprising a rate control plate having a plurality of fluid flow channels interconnected with said outlet of said collapsible reservoir; and
   (ii) operating means carried by said supporting structure for controlling fluid flow between said collapsible reservoir and said rate control means; and
   (j) adding means carried by said supporting structure for adding a medicament to said fluid contained within said fluid reservoir.

2. The dispensing device as defined in claim 1 in which said reservoir defining assembly further comprises a pierceable septum positioned over said closure wall and in which said operating means comprises a septum penetrating member movable between first and second positions.

3. The dispensing device as defined in claim 2, in which said adding means comprises a vial and in which said supporting structure housing includes a chamber for telescopically receiving said vial.

4. The dispensing device as defined in claim 2 in which said vial has an outer wall and includes:
   (a) a first open end sealed by a plunger;
   (b) a second end sealed by a pierceable septum;
   (c) a fluid reservoir disposed between said plunger and said second end;
   (d) a raised outer wall portion formed in said outer wall intermediate said first and second ends;
   (e) a barrier stopper disposed within said fluid reservoir for movement between first and second positions; and
   (f) a medicament containing chamber for containing a medicament disposed between said barrier stopper and said pierceable septum.

5. The apparatus as defined in claim 4 in which said medicament comprises a lypholized drug.

6. The dispensing device as defined in claim 2 in which said collapsible reservoir comprises a semi-rigid bellows structure.

7. The dispensing device as defined in claim 2 in which said collapsible reservoir comprises a collapsible container.

8. The dispensing device as defined in claim 2 in which said operating means further includes a control knob rotatably carried by said supporting structure for moving said penetrating member between said first position and second positions.

9. A dispensing device for dispensing medicaments to a patient comprising:
   (a) a supporting structure comprising a base assembly and a housing interconnected with said base assembly;
   (b) a carriage assembly interconnected with said supporting structure for movement between a first position and a second position;
   (c) a reservoir defining assembly including a semi-rigid collapsible fluid reservoir carried by said carriage assembly, said collapsible reservoir containing medicaments to be dispensed to the patient and having an outlet port, said reservoir defining assembly comprising a top wall, a bottom wall, a collapsible side wall interconnecting said top and bottom walls; a neck portion connected to said top wall, said neck portion having a closure wall; and a pierceable membrane positioned over said closure wall;
   (d) guide means connected to said supporting structure for guiding travel of said carriage assembly between said first position and said second position, said guide means comprising a guide member connected to said base assembly and a guide rib connected to said housing of said supporting structure;

(e) a stored energy means operably associated with said carriage assembly for moving said carriage assembly between said first and second positions, said stored energy means comprising a spring;

(f) an administration set, including an administration line interconnected with said outlet port of said collapsible reservoir;

(g) fluid flow control means carried by said base assembly of said supporting structure for controlling fluid flow from said collapsible reservoir toward said administration set, said flow control means comprising:
  (i) rate control means carried by said supporting structure for controlling the rate of fluid flow from said collapsible reservoir toward said administration set; and
  (ii) operating means carried by said supporting structure for controlling fluid flow between said collapsible reservoir and said rate control means, said operating means including a control knob carried by said supporting structure for moving said septum-penetrating member from said first position to said second position; and (h) adding means carried by said supporting structure for adding an injectable medicament to said fluid contained within said fluid reservoir.

10. The dispensing device as defined in claim 9 in which said control knob is rotatably carried by said supporting structure and in which said operating means further include indexing means for preventing rotation of said control knob.

11. The dispensing device as defined in claim 10 in which said rate control means further includes a rate control plate having a plurality of fluid flow channels interconnected with said outlet of said collapsible reservoir.

* * * * *